US011795160B2

(12) United States Patent
Aliper et al.

(10) Patent No.: US 11,795,160 B2
(45) Date of Patent: *Oct. 24, 2023

(54) KINASE INHIBITORS

(71) Applicant: INSILICO MEDICINE IP LIMITED, Hong Kong (HK)

(72) Inventors: Aleksandr Aliper, Moscow (RU); Vladimir Aladinskiy, Moscow (RU); Aleksandrs Zavoronkovs, Pak Shek Kok (HK)

(73) Assignee: Insilico Medicine IP Limited, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 16/796,864

(22) Filed: Feb. 20, 2020

(65) Prior Publication Data

US 2020/0270234 A1 Aug. 27, 2020

Related U.S. Application Data

(60) Provisional application No. 62/809,413, filed on Feb. 22, 2019.

(51) Int. Cl.

| | |
|---|---|
| ***C07D 405/04*** | (2006.01) |
| ***C07D 405/14*** | (2006.01) |
| ***C07D 409/04*** | (2006.01) |
| ***C07D 403/04*** | (2006.01) |
| ***C07D 413/04*** | (2006.01) |
| ***C07D 401/14*** | (2006.01) |
| ***C07D 401/04*** | (2006.01) |
| ***C07D 471/04*** | (2006.01) |
| ***C07D 491/048*** | (2006.01) |
| ***C07D 403/14*** | (2006.01) |
| ***C07D 417/04*** | (2006.01) |
| ***A61K 31/4439*** | (2006.01) |
| ***A61K 31/506*** | (2006.01) |
| ***A61K 31/4164*** | (2006.01) |

(52) U.S. Cl.

CPC ........ *C07D 405/04* (2013.01); *A61K 31/4164* (2013.01); *A61K 31/4439* (2013.01); *A61K 31/506* (2013.01); *C07D 401/04* (2013.01); *C07D 401/14* (2013.01); *C07D 403/04* (2013.01); *C07D 403/14* (2013.01); *C07D 405/14* (2013.01); *C07D 409/04* (2013.01); *C07D 413/04* (2013.01); *C07D 417/04* (2013.01); *C07D 471/04* (2013.01); *C07D 491/048* (2013.01)

(58) Field of Classification Search

CPC .. C07D 413/04; C07D 417/04; C07D 409/04; C07D 403/14; C07D 403/04; C07D 401/14; C07D 401/04; C07D 491/048; C07D 471/04; C07D 405/14; C07D 405/04

See application file for complete search history.

(56) References Cited

U.S. PATENT DOCUMENTS

| | | | | |
|---|---|---|---|---|
| 3,773,919 | A | 11/1973 | Boswell et al. | |
| 4,485,045 | A | 11/1984 | Regen | |
| 4,544,545 | A | 10/1985 | Ryan et al. | |
| 5,013,556 | A | 5/1991 | Woodle et al. | |
| 7,314,885 | B2 | 1/2008 | Aronov et al. | |
| 9,556,179 | B2 | 1/2017 | Velaparthi et al. | |
| 2007/0105900 | A1 * | 5/2007 | Berdini | A61P 43/00 548/215 |
| 2009/0227588 | A1 * | 9/2009 | Fleck | A61P 9/10 514/236.5 |
| 2020/0270231 | A1 | 8/2020 | Aliper et al. | |
| 2022/0274959 | A1 | 9/2022 | Zavoronkovs et al. | |
| 2022/0289723 | A1 | 9/2022 | Zavoronkovs et al. | |

FOREIGN PATENT DOCUMENTS

| | | |
|---|---|---|
| CN | 1505625 A | 6/2004 |
| CN | 1505628 A | 6/2004 |

(Continued)

OTHER PUBLICATIONS

Clark et al. J. Chem. Soc. (C), 1966, 1354-1356.*

(Continued)

*Primary Examiner* — Rebecca L Anderson

(74) *Attorney, Agent, or Firm* — Wilson Sonsini Goodrich & Rosati

(57) ABSTRACT

A TNIK and/or MAP4K4 kinase inhibitor can include: Formula A, derivative, prodrug, salt, stereoisomer, tautomer polymorph, or solvate thereof, or having chirality at any chiral center, Formula A

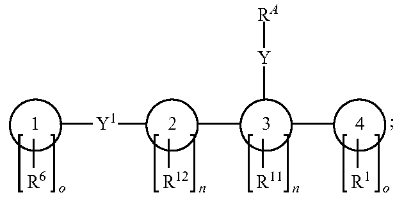

wherein: ring 1 is an aromatic ring with or without hetero atoms; ring 2 is a hetero aromatic ring; ring 3 includes at least one hetero aromatic ring and optionally at least one cycloaliphatic ring fused with the at least one hetero aromatic ring; ring 4 is an aromatic ring with or without hetero atoms; Y is a bond or a linker; $Y^1$ is a linker; each n is independently 0, 1, or 2; each o is independently 0, 1, 2, 3, 4, or 5; each $R^1$, $R^6$, $R^{11}$, and $R^{12}$ is independently a substituent; and $R^A$ is a ring structure, straight aliphatics, or branched aliphatics, which can be substituted or unsubstituted, any with or without hetero atoms.

9 Claims, No Drawings

(56) References Cited

FOREIGN PATENT DOCUMENTS

| | | | |
|---|---|---|---|
| WO | WO-9847894 | A1 | 10/1998 |
| WO | WO-0157022 | A2 | 8/2001 |
| WO | WO-0240468 | A1 | 5/2002 |
| WO | WO-02088097 | A1 | 11/2002 |
| WO | WO-2006028958 | A2 | 3/2006 |
| WO | WO-2010090716 | A1 | 8/2010 |
| WO | WO-2011025706 | A2 | 3/2011 |
| WO | WO-2016038583 | A1 | 3/2016 |
| WO | WO-2019097515 | A1 | 5/2019 |
| WO | WO-2020051207 | A2 | 3/2020 |
| WO | WO-2020078362 | A1 | 4/2020 |
| WO | WO-2020170202 | A1 | 8/2020 |
| WO | WO-2020170203 | A1 | 8/2020 |
| WO | WO-2020219792 | A1 | 10/2020 |
| WO | WO-2020230134 | A1 | 11/2020 |
| WO | WO-2020230136 | A1 | 11/2020 |

OTHER PUBLICATIONS

Registry No. 1357751-66-6, File Registry on STN, entered STN: Feb. 28, 2012.*

Registry No. 214408-80-7, file CAPLUS on STN, entered STN on Nov. 18, 1998.*

Registry No. 667400-79-9, FIle Registry on STN, entered Mar. 25, 2004.*

Carlson, et al. Systematically Mitigating the p38α Activity of Triazole-based BET Inhibitors. ACS Med Chem Lett. Aug. 2, 2019;10(9):1296-1301. doi: 10.1021/acsmedchemlett.9b00227. eCollection Sep. 12, 2019.

Eppstein et al.: Biological activity of liposome-encapsulated murine interferon gamma is mediated by a cell membrane receptor. Proc. Natl. Acad. Sci. USA 82: 3688-3692 (1985).

Hwang et al.: Hepatic uptake and degradation of unilamellar sphingomyelin/cholesterol liposomes: a kinetic study. Proc. Natl. Acad. Sci. USA 77: 4030-4034 (1980).

International search report with written opinion dated Jun. 4, 2020 for PCT/IB2020/051451.

International search report with written opinion dated Jun. 4, 2020 for PCT/IB2020/051452.

Registry No. 1349069-58-4, File Registry on STN, entered STN: Dec. 5, 2011.

Registry No. 1359379-48-8, File Registry on STN, entered STN: Mar. 2, 2012.

STN search results, RN 1359379-48-8 . . . , RN951603-22-8, etc., entered STN: Mar. 2, 2012-Oct. 26, 2007 Structure formula. (46 pages).

Co-pending U.S. Appl. No. 17/817,853, inventors Zavoronkovs; Aleksandrs et al., filed Aug. 5, 2022.

Co-pending U.S. Appl. No. 17/817,865, inventors Zavoronkovs; Aleksandrs et al., filed Aug. 5, 2022.

Registry No. 254964-43-7, File Registry on STN, entered STN: Feb. 6, 2000.

* cited by examiner

KINASE INHIBITORS

CROSS-REFERENCE

This patent application claims priority to U.S. Provisional Application No. 62/809,413 filed Feb. 22, 2019, which provisional is incorporated herein by specific reference in its entirety.

BACKGROUND

A biologically active enzyme known as TRAF2 and NCK-interacting protein kinase is an enzyme commonly known as the TNIK kinase in humans, and which is encoded by the TNIK gene. The TNIK kinase is involved in various biological processes common for serine/threonine kinases, such as acting as an activator of the Wnt signaling pathway. TNIK kinase is recruited to promoters of Wnt target genes, and may be required to activate their expression. The TNIK kinase may act by phosphorylating TCF4/TCF7L2. The TNIK kinase appears to act upstream of the JUN N-terminal pathway. The TNIK kinase may play a role in the response to environmental stress. It is also part of a signaling complex composed of NEDD4, RAP2A and TNIK, which regulates neuronal dendrite extension and arborization during development. More generally, TNIK may play a role in cytoskeletal rearrangements and regulate cell spreading. The TNIK kinase also phosphorylates SMAD1 on Thr-322.

The TNIK kinase is also considered to be a germinal center kinase (GCK), which can be characterized by an N-terminal kinase domain and a C-terminal GCK domain that serves a regulatory function.

TNIK kinase activation of Wnt signaling plays important roles in carcinogenesis and embryonic development. Mutations in this gene are associated with an autosomal recessive form of cognitive disability.

Additionally, TNIK kinase is linked to colorectal cancer, and possibly other cancers. As such, TNIK kinase has been identified as an attractive candidate for drug targeting in colorectal cancer.

The current data imply TNIK kinase is a potential target for the generation of small molecule inhibitors to specifically block the Wnt pathway in disease states such as colorectal cancer or the autosomal recessive form of cognitive disability.

Also, it is known that TGF-β-activated EMT can be inhibited through the attenuation of Smad and non-Smad signaling pathways, including the Wnt, NF-κB, FAK-Src-paxillin-related focal adhesion, and MAP kinases (ERK and JNK) signaling pathways. As such, therapeutic targets associated with EMT, such as TNIK being a target for inhibition, can be used for therapies for treating and/or preventing EMT-based disorders, such as cancer metastasis and fibrosis.

Accordingly, it would be advantageous to have a TNIK inhibitor that can inhibit TNIK activity. It would also be advantageous to have a specific TNIK inhibitor that selectively inhibits TNIK.

SUMMARY

In some embodiments, a method of inhibiting TNIK kinase and/or MAP4K4 kinase can include: contacting the TNIK kinase with compound having a structure of Formula A, or derivative thereof, prodrug thereof, salt thereof, stereoisomer thereof, tautomer thereof, polymorph thereof, or solvate thereof, or having any chirality at any chiral center.

Formula A

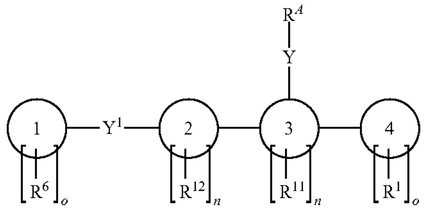

In some aspects: ring 1 is an aromatic ring with or without hetero atoms; ring 2 is a hetero aromatic ring; ring 3 includes at least one hetero aromatic ring and optionally at least one cycloaliphatic ring fused with the at least one hetero aromatic ring; ring 4 is an aromatic ring with or without hetero atoms; Y is a bond or a linker; $Y^1$ is a linker; each n is independently 0, 1, or 2; each o is independently 0, 1, 2, 3, 4, or 5; each $R^1$, $R^6$, $R^{11}$, and $R^{12}$ is independently a substituent; and $R^A$ is a ring structure, straight aliphatic chain, or branched aliphatic chain, which can be substituted or unsubstituted, any with or without hetero atoms. In one aspect, $R^{11}$ and $R^{12}$ are nothing or hydrogen. In some aspects, at least one o of ring 1 or ring 4 is at least 1.

In some embodiments, ring 1 is a phenyl group or pyridyl group; ring 2 is a 5-membered or 6 membered hetero aromatic ring, or combinations thereof, ring 3 includes a 5-membered hetero aromatic ring or a 5-membered hetero aromatic ring fused with a 6-membered hetero aromatic ring that is fused with a 5-membered cycloaliphatic ring, where the bond to Y is through the 5-membered hetero aromatic ring, or combinations thereof; ring 4 is a phenyl group, pyridyl group, pyrimidyl group, or triazinyl group, or combinations thereof; Y is a bond or an aliphatic linker; $Y^1$ is an amide linker; and $R^A$ is a cycloaliphatic ring, hetero cycloaliphatic ring, straight aliphatic, or branched aliphatic, which can be substituted or unsubstituted, any with or without hetero atoms, or combinations thereof.

In some embodiments, ring 1 is a phenyl group or pyridyl group, when ring 1 is pyridyl the nitrogen is located at the para, meta, or ortho position in the ring; ring 2 is a furanyl group, thiophenyl group, pyrrolyl group, oxazolyl group, thiazolyl group, imidazolyl group, triazolyl group, or pyridyl group; ring 3 is a imidzaolyl group, triazolyl group, or cyclopenta-pyrrolo-pyridinyl fused ring group; or cyclopenta-furo-pyridinyl group; ring 4 is a phenyl group, pyridyl group, pyrimidyl group, or triazinyl group, when ring 4 is pyridyl the nitrogen is located at the para, meta, or ortho positions in the ring; when ring 4 is pyrimidyl group, the nitrogens are at the meta or ortho positions in the ring; Y is a bond or 1-membered to 6-membered aliphatic chain; $Y^1$ is an amide, sulfonimidamide, ketone, carboxamide linker, or combination thereof, substituted or unsubstituted; and $R^A$ is a 3-membered to 6-membered cycloaliphatic ring, 5-membered to 6-membered hetero cycloaliphatic ring; 1-membered to 12-membered straight aliphatic chain, or 1-membered to 12-membered branched aliphatic chain, any of which can be substituted or unsubstituted, any aliphatic chain can be with or without hetero atoms.

In some embodiments, each $R^1$, $R^6$, $R^{11}$, and $R^{12}$ is independently hydrogen, F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., $CH3C{=}O$), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl. In some aspects, $R^{11}$ and $R^{12}$ are hydrogen or nothing.

In some embodiments, a method of inhibiting TNIK kinase and/or MAP4K4 kinase can include: contacting the TNIK kinase and/or MAP4K4 kinase with compound having a structure of Formula A1 or Formula A2, derivative thereof, prodrug thereof, salt thereof, stereoisomer thereof, tautomer thereof, polymorph thereof, or solvate thereof, or having any chirality at any chiral center.

Formula A1

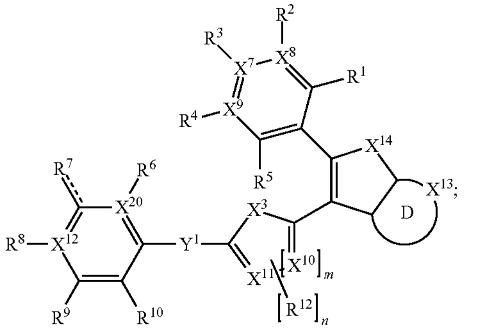

Formula A2

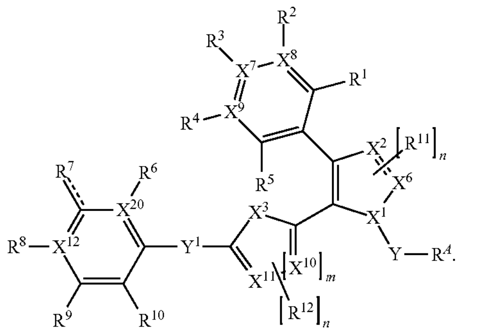

In some aspects: $R^A$ is a ring structure, straight aliphatic, or branched aliphatic, any of which can be substituted or unsubstituted, any with or without hetero atoms; ring D is a ring structure having one or more rings linked together; the $X^1$, $X^2$, $X^3$, $X^6$, $X^7$, $X^8$, $X^9$, $X^{10}$, $X^{11}$, $X^{12}$, $X^{13}$, and $X^{14}$ are each independently a carbon or a hetero atom with or without a substituent; each $R^1$, $R^2$, $R^3$, $R^4$, $R^5$, $R^6$, $R^7$, $R^8$, $R^9$, $R^{10}$, $R^{11}$, and $R^{12}$ is independently a substituent; Y is a bond or a linker; $Y^1$ is a linker; m is 1, 2, or 3; and n is 0, 1, or 2. In some aspects, when an X group is N in an aromatic ring, the R group bonded thereto is nothing. In some aspects, n is 0 and $R^{11}$ and/or $R^{12}$ are each nothing. If present, $R^{11}$ and/or $R^{12}$ may be on any appropriate ring atom. When n is 0, then the bond and $R^{11}$ and/or $R^{12}$ is absent. In some aspects, the $R^A$ ring is linked directly to $X^1$, such as through a covalent bond (i.e., Y). When $R^A$ is a ring it can be any cycloaliphatic or hetero cycloaliphatic, or combination thereof.

In some embodiments, the method can include administering a compound of structure of Formulae 1A, 2A, 3A, 4A, or 5A, or derivative thereof, prodrug thereof, salt thereof, stereoisomer thereof, tautomer thereof, polymorph thereof, or solvate thereof, or having any chirality at any chiral center.

Formula 1A

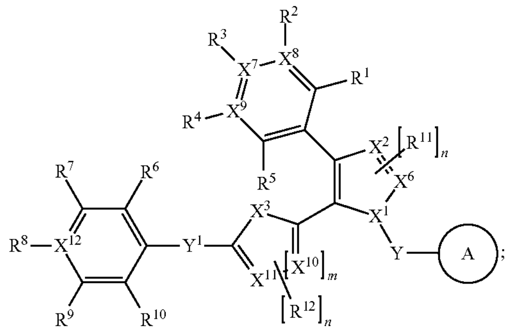

Formula 2A

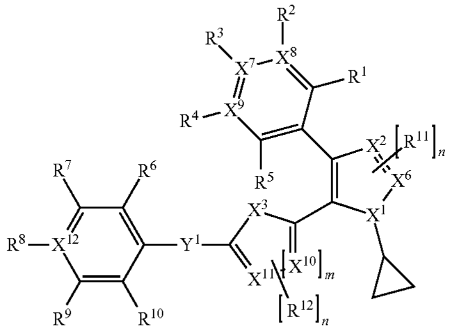

Formula 3A

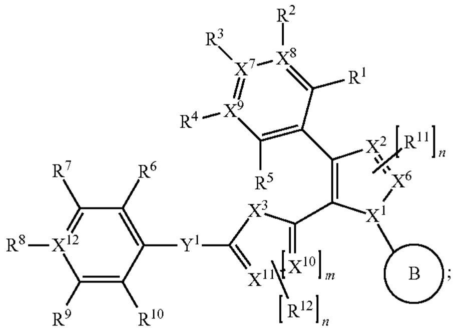

Formula 4A

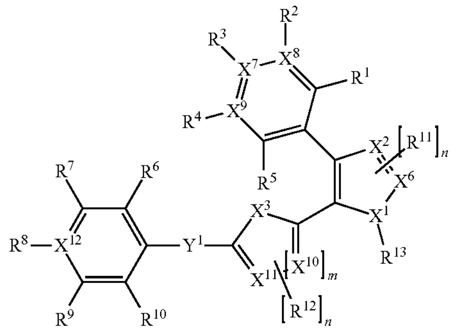

-continued

Formula 5A

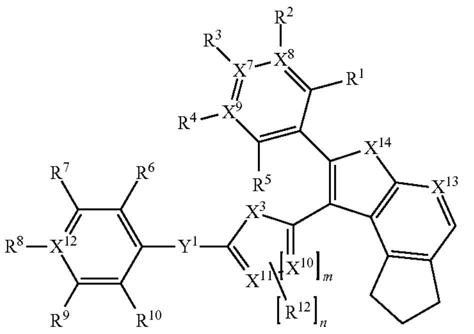

In some aspects: in Formula 1A, A is a ring structure with or without hetero atoms, which may be substituted or unsubstituted; in Formula 3A, B is a ring structure with at least one hetero atom, any substituted or unsubstituted; and in Formula 4A, $R^{13}$ is a straight aliphatic, or branched aliphatic, which can be substituted or unsubstituted, any with or without hetero atoms.

In some embodiments, ring A is a cycloaliphatic or hetero cycloaliphatic, or combination thereof, which can be substituted or unsubstituted with an R group. In some aspects, ring B can only be a hetero cycloaliphatic. In some aspects, $R^{13}$ is independently a substituent, such as those described for $R^{11}$. $X^1$ and/or $X^2$ is CH, or N. $X^3$ is $CH_2$, NH, O or S. $X^6$, $X^7$, $X^8$, $X^9$, $X^{10}$, $X^{11}$, X' $^{12}$ and/or $X^{13}$ are CH or N. $X^{14}$ is O or NH. $R^1$, $R^2$, $R^3$, $R^4$, $R^5$, $R^6$, $R^7$, $R^8$, $R^9$, $R^{10}$, $R^{11}$, and $R^{12}$ are each independently hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, derivatives thereof, any substituted or unsubstituted, or combinations thereof.

In some embodiments: ring A is a cycloaliphatic with 3-12 ring atoms, hetero cycloaliphatic with 3-12 ring atoms, or combinations thereof, which can be substituted or unsubstituted; ring B is a hetero cycloaliphatic with 3-12 ring atoms, which can be substituted or unsubstituted; ring D is a polycycle having at least an aromatic ring fused to cyclic aliphatic; $X^1$ and/or $X^2$ is CH or N; $X^3$ is $CH_2$, NH, O, or S; $X^6$, $X^7$, $X^8$, $X^9$, $X^{10}$, $X^{11}$, $X^{11}$, $X^{12}$, and/or $X^{13}$ is CH or N; $X^6$, $X^7$, $X^8$, $X^9$, $X^{10}$, $X^{11}$, $X^{11}$, $X^{12}$, and/or $X^{13}$ is CH or N or O; and the $R^1$, $R^2$, $R^3$, $R^4$, $R^5$, $R^6$, $R^7$, $R^8$, $R^9$, $R^{10}$, $R^{11}$, and $R^{12}$ are each independently hydrogen, alkyl, alkenyl, alkynyl, aryl, alkaryl, aralkyl, halo, hydroxyl, sulthydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, derivatives thereof, any substituted or unsubstituted, and combinations thereof. In some aspects, $R^{13}$ is a C1-C24 straight aliphatic or branched aliphatic, which can be substituted or unsubstituted, any with or without hetero atoms.

In some embodiments: ring A is a cycloaliphatic with 3-6 ring atoms, hetero cycloaliphatic with 3-6 ring atoms, or combinations thereof, which can be substituted or unsubstituted; ring B is a hetero cycloaliphatic with 3-6 ring atoms, which can be substituted or unsubstituted; ring D is a cyclopentapyridine; $X^1$ and $X^2$ are N; $X^3$ is O or NH; $X^4$ is NH; $X^5$ is O; $X^6$, $X^7$, $X^8$, $X^9$, $X^{10}$, $X^{11}$, and/or $X^{12}$ is CH or N; $X^{13}$ is N; $X^{14}$ is O or NH; and the $R^1$, $R^2$, $R^3$, $R^4$, $R^5$, $R^6$, $R^7$, $R^8$, $R^9$, $R^{10}$, $R^{11}$, and $R^{12}$ are each independently any one or more of the substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulflrydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, isocyano, cyanato, isocyanato, thiocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonate, $C_1$-$C_{24}$ alkylsulfanyl, $C_5$-$C_{20}$ arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, any with or without hetero atoms, any substituted or unsubstituted, derivatives thereof, and combinations thereof; and $R^{13}$ is a $C_1$-$C_{12}$ straight aliphatic or branched aliphatic, which can be substituted or unsubstituted, any with or without hetero atoms.

In some embodiments, $R^1$, $R^2$, $R^3$, $R^4$, $R^5$, $R^6$, $R^7$, $R^8$, $R^9$, $R^{10}$, $R^{11}$, and $R^{12}$ are each independently H, F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., acetyl, CH3C═O), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl.

In some embodiments, inhibiting the TNIK can inhibit certain TNIK related biological pathways. In some aspects, the inhibiting of TNIK inhibits the Wnt pathway. In some aspects, the inhibiting of TNIK inhibits cytoskeletal rearrangements. In some aspects, the inhibiting of TNIK inhibits carcinogenesis. In some aspects, the inhibiting of TNIK inhibits embryonic development. In some aspects, the inhibiting of TNIK inhibits colorectal cancer. In some aspects, the inhibiting of TNIK inhibits TGF-betasignaling. In some aspects, the inhibiting of inhibiting TNIK inhibits glycosaminoglycan formation. In some aspects, the inhibiting of TNIK inhibits collagen formation. In some aspects, the inhibiting of TNIK inhibits fibrosis.

In some embodiments, inhibiting the MAP4K4 kinase can inhibit certain MAP4K4 pathways. MAP4K4 is involved in a wide array of physiological processes including cell migration, proliferation and adhesion, and thereby inhibition of MAP4K4 can inhibit these processes. As such, the compounds that function as a MAP4K4 inhibitor can have activity in inhibiting systemic inflammation, metabolic disorders, cardiovascular disease, and cancer.

In some embodiments, a TNIK kinase and/or MAP4K4 kinase compound can include: a structure of Formula A, or derivative thereof, prodrug thereof, salt thereof, stereoisomer thereof, tautomer thereof, polymorph thereof, or solvate thereof, or having any chirality at any chiral center.

In some aspects: ring 1 is an aromatic ring with or without hetero atoms; ring 2 is a hetero aromatic ring; ring 3 includes at least one hetero aromatic ring and optionally at least one cycloaliphatic ring fused with the at least one hetero aromatic ring; ring 4 is an aromatic ring with or without hetero atoms; Y is a bond or a linker; $Y^1$ is a linker; each n is independently 0, 1, or 2; each o is independently 0, 1, 2, 3, 4, or 5; each $R^1$, $R^6$, $R^{11}$, and $R^{12}$ is independently a substituent. In some aspects, the compound includes at least one of the following provisions: $Y^1$ is an amide having the nitrogen bonded to ring 1 and the carbon bonded to ring 2; the compound includes at least one of the following for Y: when Y is a bond, $R^A$ is a $C_3$ cycloaliphatic ring, 5-membered hetero cycloaliphatic ring, 6-membered hetero cycloaliphatic ring, straight aliphatic chain, or branched aliphatic chain, any of which can be substituted or unsubstituted; or when Y is a chemical moiety, $R^A$ is a $C_3$ cycloaliphatic ring, 5-membered cycloaliphatic ring, 5-membered hetero cycloaliphatic ring, 6-membered cycloaliphatic ring, 6-membered hetero cycloaliphatic ring, straight aliphatic chain, or branched aliphatic chain, which can be substituted or unsubstituted and with or without hetero atoms; or the compound includes at least one of the following: when ring 1 is a phenyl group, at least one of: ring 2 is not a furanyl group; ring 3 is not an imidazolyl group; or ring 4 is not phenyl group; when ring 2 is a furanyl group, at least one of: ring 1 is not a phenyl group; ring 3 is not an imidazolyl group, or ring 4 is not a phenyl group; when ring 3 is an imidazolyl group, at least one of: ring 1 is not a phenyl group; ring 2 is not a furanyl group; or ring 4 is not a phenyl group; or when ring 4 is a phenyl group, at least one of: ring 1 is not a phenyl group; ring 2 is not a furanyl group; or ring 3 is not an imidazolyl group.

In some aspects, ring 1 is a phenyl group or pyridyl group; ring 2 is a 5-membered or 6 membered hetero aromatic ring; ring 3 includes a 5-membered hetero aromatic ring or a 5-membered hetero aromatic ring fused with a 6-membered hetero aromatic ring that is fused with a 5-membered cycloaliphatic ring, where the bond to Y is through the 5-membered hetero aromatic ring; ring 4 is a phenyl group, pyridyl group, pyrimidyl group, or triazinyl group; Y is a bond or an aliphatic linker; $Y^1$ is an amide linker; and $R^A$ is a cycloaliphatic ring, hetero cycloaliphatic ring; straight aliphatic, or branched aliphatic, which can be substituted or unsubstituted, any with or without hetero atoms, wherein when Y is a bond $R^A$ is not a 5-membered cycloaliphatic ring.

In some embodiments, ring 1 is a phenyl group or pyridyl group, when ring 1 is pyridyl the nitrogen is located at the para, meta, or ortho position in the ring; ring 2 is a furanyl group, thiophenyl group, pyrrolyl group, oxazolyl group, thiazolyl group; imidazolyl group, triazolyl group, or pyridyl group; ring 3 is a imidazolyl group, triazolyl group, or cyclopenta-pyrrolo-pyridinyl fused ring group; or cyclopenta-furo-pyridinyl group; ring 4 is a phenyl group, pyridyl group, pyrimidyl group, or triazinyl group, when ring 4 is pyridyl the nitrogen is located at the para, meta, or ortho positions in the ring; when ring 4 is pyrimidyl group, the nitrogens are at the meta or ortho positions in the ring; Y is a bond or 1-membered to 6-membered aliphatic; $Y^1$ is an amide linker; and when Y is a 1-membered to 6-membered (e.g., $C_1$-$C_6$) aliphatic linker, $R^A$ is a 3-membered to 6-membered (e.g., $C_3$-$C_6$) cycloaliphatic ring, 5-membered to 6-membered (e.g., $C_5$-$C_6$) hetero cycloaliphatic ring; 1-membered to 12-membered (e.g., $C_1$-$C_{12}$) straight aliphatic, or $C_1$-$C_{12}$ branched aliphatic, which can be substituted or unsubstituted, any with or without hetero atoms, or when Y is a bond, $R^A$ is a not a 5-membered to 6-membered (e.g., not $C_6$-$C_6$) cycloaliphatic ring.

In some embodiments, each of $R^1$, $R^6$, $R^{11}$, and $R^{12}$ is independently F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., $CH_3C{=}O$), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl. In some aspects, $R^{11}$ and $R^{12}$ are hydrogen or nothing.

In some embodiments, a TNIK kinase and/or MAP4K4 kinase can be a compound, comprising: a structure of Formula A1 or Formula A2, or derivative thereof, prodrug thereof, salt thereof, stereoisomer thereof, tautomer thereof, polymorph thereof, or solvate thereof, or having any chirality at any chiral center.

Formula A1

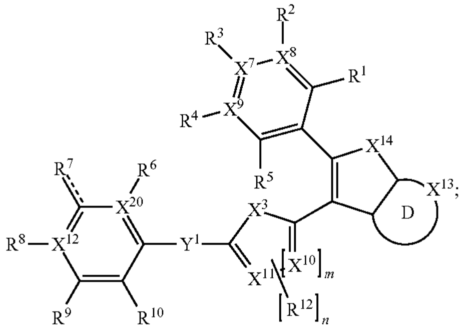
;

-continued

Formula A2

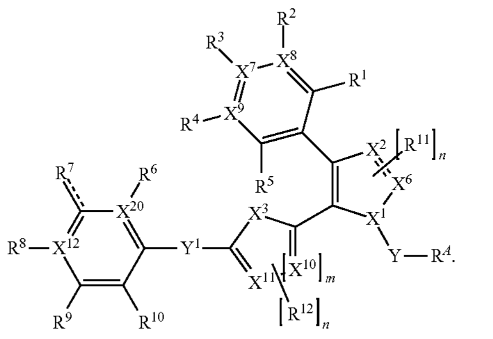

In some aspects: $R^A$ is a $C_3$ cycloaliphatic, 4-membered to 12-membered (e.g., $C_4$-$C_{12}$) hetero cycloaliphatic, straight aliphatic chain, or branched aliphatic chain, any substituted or unsubstituted, wherein the $C_3$ cycloaliphatic, straight aliphatic chain, or branched aliphatic chain are with or without hetero atoms; ring D is a ring structure having one or more rings fused together; each $R^1$, $R^2$, $R^3$, $R^5$, $R^6$, $R^7$, $R^8$, $R^9$, $R^{10}$, $R^{11}$, and $R^{12}$ is independently a substituent; the $X^1$, $X^2$, $X^3$, $X^6$, $X^7$, $X^8$, $X^9$, $X^{10}$, $X^{11}$, $X^{12}$, $X^{13}$, and $X^{14}$ are each independently a carbon or a hetero atom with or without a substituent; Y is a bond or a linker; $Y^1$ is a linker; m is 1, 2, or 3; and n is 0, 1, or 2. In some aspects, when an X group is N in an aromatic ring, the R group bonded thereto is nothing.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the chemical structures, can be arranged, substituted, combined, separated, and designed in a wide variety of different configurations, all of which are explicitly contemplated herein.

Generally, the present invention relates to at least one molecule that functions as a kinase inhibitor, such as a TNIK kinase and/or MAP4K4 kinase. As such, the molecules described herein can be used in methods related to inhibiting TNIK, so as to inhibit the biological activity of TNIK and thereby inhibit the biological pathways associated with TNIK activation. As a result, the molecules can be used in therapeutic methods where inhibiting TNIK can provide a therapy to a subject that is administered the molecule. Thus, the molecules described herein can each be referred to as a TNIK kinase inhibitor, where some may be broad spectrum inhibitors of many kinases, and some are specific inhibitors that inhibit a specific kinase, such as TNIK kinase and/or MAP4K4 kinase.

Methods

Accordingly, the TNIK kinase inhibitors can be used to inhibit a biological pathway downstream from inhibiting TNIK. In some aspects, the TNIK inhibitor can inhibit fibrillar collagen, and thereby can inhibit biological activity related to regulation of the extracellular matrix, and regulation of remodeling the extracellular matrix. The TNIK inhibitor can inhibit regulation of cell growth, differentiation, cell migration, proliferation, and metabolism.

In some embodiments, inhibiting the TNIK can inhibit certain TNIK related biological pathways. In some aspects, the inhibiting of TNIK inhibits the Wnt pathway.

In some embodiments, the inhibiting of TNIK inhibits cytoskeletal rearrangements. The inhibition of TNIK can inhibit the c-Jun N-terminal kinase pathway. The inhibition of TNIK can inhibit the phosphorylation of Gelsolin. The inhibition of TNIK can inhibit the regulation of the cytoskeleton, such as cytoskeletal rearrangements.

In some embodiments, the inhibiting of TNIK inhibits carcinogenesis. In some aspect, the administering of the TNIK inhibitor includes a therapeutically effective amount of the compound sufficient to treat cancer by: inhibiting cancer cell growth; inhibiting cancer cell migration; or inhibiting cancer cell proliferation. In some aspects, the cancer is colorectal cancer.

In some embodiments, the inhibiting of TNIK inhibits embryonic development. As such, the TNIK inhibitor can inhibit pregnancy progression and thereby be used for terminating a pregnancy.

In some embodiments, the inhibiting of TNIK inhibits TGF-betasignaling. The TGF-betasignaling pathway is involved in a various processes, and thereby inhibiting the TGF-betasignaling pathway can inhibit these processes, some of which are described herein. This can include inhibiting development of an embryo as described herein for inhibiting progression of pregnancy. This can include inhibiting cell growth, cell differentiation, which may be used to inhibit pregnancy progression as well as inhibiting cancer.

In some embodiments, inhibiting the TG-betasignaling can be used for inhibiting formation of extracellular matrix or overformation of extracellular matrix and the problems associated therewith (e.g., fibrosis). In some aspects, the inhibiting of TGF-beta signaling by inhibiting TNIK inhibits glycosaminoglycan formation. In some aspects, the inhibiting of TGF-betaby inhibiting TNIK inhibits collagen formation. In some aspects, the inhibiting of TNIK inhibits fibrosis. In some aspects, the inhibited fibrosis is selected from pulmonary fibrosis (e.g., idiopathic or radiation induced), cystic fibrosis, liver fibrosis (e.g., cirrhosis), myocardial fibrosis (e.g., atrial fibrosis, endomyocardial fibrosis, old myocardial infarction), kidney fibrosis, brain fibrosis (e.g., glial scar), arterial fibrosis, arthrofibrosis (e.g., knee, shoulder, other joints), intestinal fibrosis (e.g., Crohn's disease), Dupytren's contracture fibrosis (e.g., hands, fingers), keloid fibrosis (e.g., skin), mediastinal fibrosis (e.g., soft tissue of the mediastinum), myelofibrosis (e.g., bone marrow), peyronie's disease fibrosis (e.g., penis), progressive massive fibrosis (e.g., lungs, complication of coal worker's pneumoconiosis), retroperitoneal fibrosis (e.g., soft tissue of the retroperitoneum), scleroderma sclerosis fibrosis (e.g., skin, lungs), adhesive capsulitis fibrosis (e.g., shoulder), or combinations thereof.

In some embodiments, the TNIK inhibitor can be used to inhibit the epithelial to mesenchymal transition of cancer cells and/or development of fibrosis. In some aspects, this can include inhibiting the Smad signaling pathways. In some aspects, this can include inhibiting the non-Smad signaling pathways. In some aspects, this can include inhibiting Wnt, NF-KB, FAC-Src-paxillin-related focal adhesion, and MAP kinases (e.g., ERK and JNK) signaling pathways.

The therapeutic treatments provided herein can be used for prophylactic to inhibit the onset, development, or progression of the disease state. As such, the TNIK inhibitor can be used for a prophylactic or treatment of the recited disease states.

In some embodiments, the TNIK inhibitor has a structure of any formula provided herein, or derivative thereof, prodrug thereof, salt thereof, or stereoisomer thereof, or having any chirality at any chiral center, or tautomer, polymorph, solvate, or combination thereof, as presented herein. In some instances, the compounds can be pharmaceutically acceptable salts. As in these formulae, the R substituent groups can be any substituents. For example, the R substituent groups can be one or more of the substituents recited herein or combinations thereof.

Similarly, inhibiting MAP4K4 kinase can inhibit its related biological functions.

In some embodiments, a method of inhibiting a kinase (e.g., TNIK kinase and/or MAP4K4 kinase) can include: contacting the kinase with compound having a structure of Formula A, or derivative thereof, prodrug thereof, salt thereof, stereoisomer thereof, tautomer thereof, polymorph thereof, or solvate thereof, or having any chirality at any chiral center.

Formula A

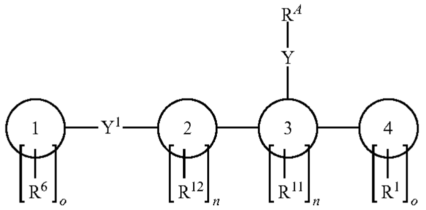

In some aspects: ring 1 is an aromatic ring with or without hetero atoms; ring 2 is a hetero aromatic ring; ring 3 includes at least one hetero aromatic ring and optionally at least one cycloaliphatic ring fused with the at least one hetero aromatic ring; ring 4 is an aromatic ring with or without hetero atoms; Y is a bond or a linker; $Y^1$ is a linker; each n is independently 0, 1, or 2; each o is independently 0, 1, 2, 3, 4, or 5; each $R^1$, $R^6$, $R^{11}$, and $R^{12}$ is independently a substituent; and $R^A$ is a ring structure, straight aliphatic chain, or branched aliphatic chain, which can be substituted or unsubstituted, any with or without hetero atoms.

In some embodiments, ring 1 is a phenyl group, pyridyl group, or pyrimidinyl group; ring 2 is a 5-membered or 6 membered hetero aromatic ring; ring 3 includes a 5-membered hetero aromatic ring or a 5-membered hetero aromatic ring fused with a 6-membered hetero aromatic ring that is fused with a 5-membered cycloaliphatic ring, where the bond to Y is through the 5-membered hetero aromatic ring; ring 4 is a phenyl group, pyridyl group, pyrimidyl group, or triazinyl group; Y is a bond or an aliphatic linker; $Y^1$ is an amide linker; and $R^A$ is an aromatic ring, hetero aromatic ring, cycloaliphatic ring, hetero cycloaliphatic ring; straight aliphatic, or branched aliphatic, which can be substituted or unsubstituted, any with or without hetero atoms.

In some embodiments ring 1 is a phenyl group, pyridyl group, or pyrimidinyl group, when ring 1 is pyridyl or pyrimidinyl the nitrogens are located at the para, meta, or ortho position in the ring; ring 2 is a furanyl group, thiophenyl group, pyrrolyl group, oxazolyl group, thiazolyl group, imidazolyl group, triazolyl group, or pyridyl group; ring 3 is a imidzaolyl group, triazolyl group, or cyclopenta-pyrrolo-pyridinyl fused ring group; or cyclopenta-furo-pyridinyl group; ring 4 is a phenyl group, pyridyl group, pyrimidyl group, or triazinyl group, when ring 4 is pyridyl the nitrogen is located at the para, meta, or ortho positions in the ring; when ring 4 is pyrimidyl group, the nitrogens are at the meta or ortho positions in the ring; Y is a bond or 1-membered to 6-membered (e.g., $C_1$-$C_6$) aliphatic; $Y^1$ is an amide linker; and $R^A$ is an aromatic ring, hetero aromatic ring, a 1-membered to 6-membered (e.g., $C_3$-$C_6$) cycloaliphatic ring, 5 membered to 6-membered hetero cycloaliphatic ring; 1-membered to 12-membered (e.g., $C_1$-$C_{12}$) straight aliphatic chain, or 1-membered to 12-membered (e.g., $C_1$-$C_{11}$) branched aliphatic, which can be substituted or unsubstituted, any with or without hetero atoms.

In some embodiments, each $R^1$, $R^6$, $R^{11}$, and $R^{12}$ is independently F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., CH3C═O), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl. In some aspects, $R^{11}$ and $R^{12}$ are hydrogen or nothing.

In some embodiments, when Y is a $C_1$-$C_6$ aliphatic linker, $R^A$ is a $C_3$-$C_6$ cycloaliphatic ring, $C_5$-$C_6$ hetero cycloaliphatic ring, aromatic ring, $C_1$-$C_{11}$ straight aliphatic, or $C_1$-$C_{11}$ branched aliphatic, which can be substituted or unsubstituted, any with or without hetero atoms, or when Y is a bond, $R^A$ is a not a $C_6$-$C_6$ cycloaliphatic ring.

In some embodiments, each $R^1$, $R^6$, $R^{11}$, and $R^{12}$ is independently hydrogen, F, Br, Cl, I, methyl, ethyl, propyl, butyl, pentyl, hexyl, heptyl, octyl, isopropyl, tert-butyl, trifluoromethyl, oxygen, oxide, hydroxy, methoxy, ethoxy, propoxy, butoxy, pentoxy, hexoxy, heptoxy, octoxy, trifluromethyloxy, methylthio, ethylthio, propylthio, butylthio, pentylthio, hexylthio, heptylthio, octylthio, methylalcohol, ethylalcohol, propylalcohol, butylalcohol, pentylalcohol, hexylalcohol, heptylalcohol, octylalcohol, acetyl, carboxylic acid, alkyl carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethylsulfanyl, propylsulfanyl, butylsulfanyl, pentylsulfanyl, hexylsulfanyl, heptylsulfanyl, octylsulfanyl, sulfamoyl, methylpiperazinium, piperazinyl, hydroxyethylpiperazinyl, bis(2-hydroxyethyl)amino, morpholino, or combinations thereof.

In some embodiments, $R^{11}$ and $R^{12}$ are hydrogen or nothing, and each $R^1$ or $R^6$ is independently hydrogen, F, Br, Cl, I, methyl, ethyl, propyl, butyl, pentyl, hexyl, heptyl, octyl, isopropyl, tert-butyl, trifluoromethyl, oxygen, oxide, hydroxy, methoxy, ethoxy, propoxy, butoxy, pentoxy, hexoxy, heptoxy, octoxy, trifluromethyloxy, methylthio, ethylthio, propylthio, butylthio, pentylthio, hexylthio, heptylthio, octylthio, methylalcohol, ethylalcohol, propylalcohol, butylalcohol, pentylalcohol, hexylalcohol, heptylalcohol, octylalcohol, acetyl, carboxylic acid, alkyl carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethylsulfanyl, propylsulfanyl, butylsulfanyl, pentylsulfanyl, hexylsulfanyl, heptylsulfanyl, octylsulfanyl, sulfamoyl, methylpiperazinium, piperazinyl, hydroxyethylpiperazinyl, bis(2-hydroxyethyl)amino, morpholino, or combinations thereof.

In some embodiments, each $R^1$ is independently hydrogen, F, Br, Cl, I, methyl, ethyl, propyl, butyl, pentyl, hexyl, heptyl, octyl, isopropyl, tert-butyl, trifluoromethyl, hydroxy, methoxy, ethoxy, propoxy, butoxy, pentoxy, hexoxy, heptoxy, octoxy, trifluromethyloxy, or combinations thereof.

In some embodiments, $R^{11}$ and $R^{12}$ are hydrogen or nothing, and each $R^6$ is independently hydrogen, F, Br, Cl, I, methyl, ethyl, propyl, butyl, pentyl, hexyl, heptyl, octyl, isopropyl, tert-butyl, trifluoromethyl, oxygen, oxide, hydroxy, methoxy, ethoxy, propoxy, butoxy, pentoxy, hexoxy, heptoxy, octoxy, trifluromethyloxy, methylthio, ethylthio, propylthio, butylthio, pentylthio, hexylthio, heptylthio, octylthio, methylalcohol, ethylalcohol, propylalcohol, butylalcohol, pentylalcohol, hexylalcohol, heptylalcohol, octylalcohol, acetyl, carboxylic acid, alkyl carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethylsulfanyl, propylsulfanyl, butylsulfanyl, pentylsulfanyl, hexylsulfanyl, heptylsulfanyl, octylsulfanyl, sulfamoyl, methylpiperazinium, piperazinyl, hydroxyethylpiperazinyl, bis(2-hydroxyethyl)amino, morpholino, or combinations thereof.

In some embodiments, $Y^1$ is an amide, hydrazide, carbohydrazide, hydroxy-substituted amide, alkyl-substituted amide, carboximidamide, or sulfonimidamide.

In some embodiments, $R^A$ is from hydrogen, cyclopentyl, tetrahydrofuranyl, pyrrolidinyl, piperidinyl, pyridinyl, pyrimidinyl, bicycloheptanyl, bicyclooctanyl, bicyclo[3.1.1]heptan-3yl, bicyclo [2.2.2 octan-2yl, bicyclo[3.2.1]octan-3-yl, fluorotetrahydrofuranyl, difluorotetrahydrofuranyl, oxetanyl, hydroxycyclopentyl, methylcyclopentyl, cyclopropyl, cyclobutyl, cyclopentyl, cyclohexyl, methyl, ethyl, propyl, butyl, pentyl, hexyl, heptyl, octyl, isopropyl, tert-butyl, hydroxypropanyl, trifluoromethyl, methoxy, ethoxy, propoxy, butoxy, pentoxy, hexoxy, heptoxy, octoxy, phenyl, or combinations thereof.

In some embodiments, a method of inhibiting a kinase (e.g., TNIK kinase and/or MAP4K4 kinase) can include: contacting the kinase with compound having a structure of one of Formula A1 or Formula A2, derivative thereof, prodrug thereof, salt thereof, stereoisomer thereof, tautomer thereof, polymorph thereof, or solvate thereof, or having any chirality at any chiral center, Formula A1

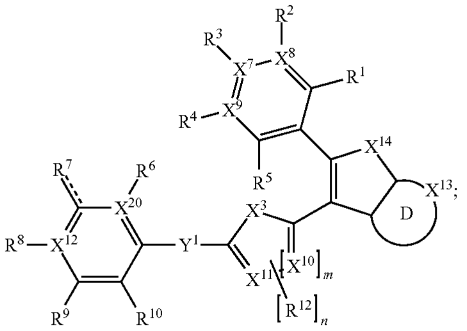

Formula A2

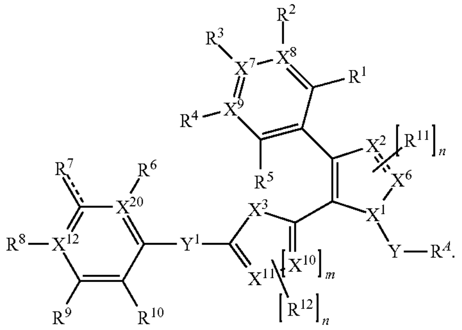

wherein: $R^A$ is a ring structure, straight aliphatic, or branched aliphatic, which can be substituted or unsubstituted, any with or without hetero atoms; ring D is a ring structure having one or more rings linked together; the $X^1$, $X^2$, $X^3$, $X^6$, $X^7$, $X^8$, $X^9$, $X^{10}$, $X^{11}$, $X^{12}$, $X^{13}$, and $X^{14}$ are each independently a carbon or a hetero atom with or without a substituent; each $R^1$, $R^2$, $R^3$, $R^4$, $R^5$, $R^6$, $R^7$, $R^8$, $R^9$, $R^{10}$, $R^{11}$, and $R^{12}$ is independently a substituent; Y is a bond or a linker; $Y^1$ is a linker; m is 1, 2, or 3; and n is 0, 1, or 2. In some aspects, when an X group is N in an aromatic ring, the R group bonded thereto is nothing. In some aspects, n is 0 and $R^{11}$ and/or $R^{12}$ are each nothing. If present, $R^{11}$ and/or $R^{12}$ may be on any appropriate ring atom. When n is 0, then the bond and $R^{11}$ and/or $R^{12}$ is absent. In some aspects, the $R^A$ ring is linked directly to $X^1$, such as through a covalent bond (i.e., Y). When $R^A$ is a ring it can be any cycloaliphatic or hetero cycloaliphatic, or combination thereof.

In some embodiments, $Y^1$ can be:

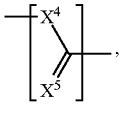

which can be

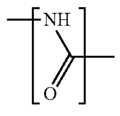

or

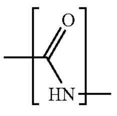

or other linker such as for Y, or $X^4$ and/or $X^5$ can be as defined herein. In some aspects, $X^4$ is C (e.g., CH, $CH_2$) or N (e.g., N, NH, $NR^1$, $NOR^1$), any with or without a substituent (e.g., $R^1$); and $X^5$ is a O or N (e.g., NH, $NR^1$, $NOR^1$). Here, $R^1$ is as defined herein, where H, OH, methyl, ethyl, trifluoromethyl are examples. The $X^4$ can be C, NH or NOH, or $NOR^1$. $X^5$ is a O or $NR^1$, or $NOR^1$.

In some embodiments, the method can include administering a compound of structure of one of Formulae 4A-4K or 5A-5K, or derivative thereof, prodrug thereof, salt thereof, stereoisomer thereof, tautomer thereof, polymorph thereof, or solvate thereof, or having any chirality at any chiral center.

Formula 4A

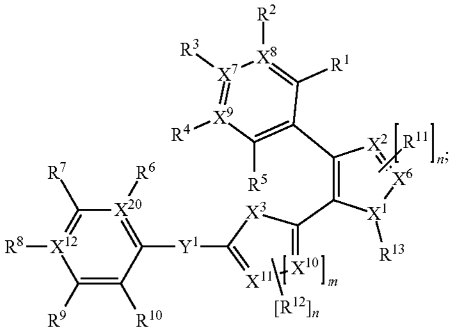

Formula 5A

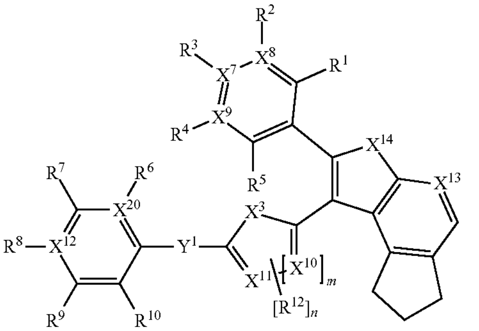

Wherein, $R^{13}$ is selected from: hydrogen, straight aliphatic, branched aliphatic, Y-Ring A

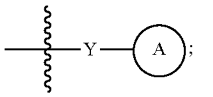

Ring B

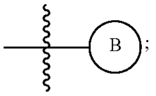

Ring C

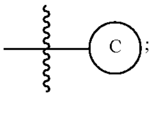

-continued

Fused Ring D

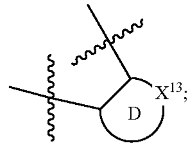

Fused Ring E

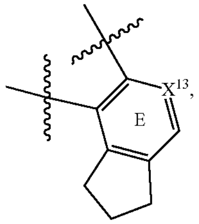

Fused Ring E, or —Y—$R^A$ any of which can be substituted or unsubstituted, any with or without hetero atoms.

In some aspects: in Formula 1A, A is a ring structure with or without hetero atoms, any substituted or unsubstituted; in Formula 3A, B is a ring structure with at least one hetero atom, any substituted or unsubstituted; and in Formula 4A, $R^{13}$ is a straight aliphatic, branched aliphatic, cycloaliphatic, cyclopropane, aryl, polyaryl, —Y—$R^A$, $R^B$, fused ring D (e.g., fused with $X^1$ and $X^6$), fused ring E (e.g., example of fused ring D) combination thereof, any of which can be substituted or unsubstituted, any with or without hetero atoms.

In some embodiments, ring A is a cycloaliphatic or hetero cycloaliphatic, or combination thereof, which can be substituted or unsubstituted with an R group. In some aspects, Ring B can only be a hetero cycloaliphatic. In some aspects, $R^{13}$ is independently a substituent, such as those described for $R^{11}$. $X^1$ and/or $X^2$ is CH, or N. $X^3$ is $CH_2$, NH, O or S. $X^6$, $X^7$, $X^8$, $X^9$, $X^{10}$, $X^{11}$, $X^{12}$, and/or $X^{13}$ are CH or N. $X^{14}$ is O or NH. $R^1$, $R^2$, $R^3$, $R^4$, $R^5$, $R^6$, $R^7$, $R^8$, $R^9$, $R^{10}$, $R^{11}$, and $R^{12}$ are each independently hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, derivatives thereof, any substituted or unsubstituted, or combinations thereof.

In some embodiments: ring A is a cycloaliphatic with 3-12 ring atoms, hetero cycloaliphatic with 3-12 ring atoms, or combinations thereof, which can be substituted or unsubstituted; ring B is a hetero cycloaliphatic with 3-12 ring atoms, which can be substituted or unsubstituted; ring D is a polycycle having at least an aromatic ring fused to cyclic aliphatic; $X^1$ and/or $X^2$ is CH or N; $X^3$ is $CH_2$, NH, O, or S; $X^6$, $X^7$, $X^8$, $X^9$, $X^{10}$, $X^{11}$, $X^{11}$, $X^{12}$, and/or $X^{13}$ is CH or N; $X^6$, $X^7$, $X^8$, $X^9$, $X^{10}$, $X^{11}$, $X^{11}$, $X^{12}$, and/or $X^{13}$ is CH or N or O; and the $R^1$, $R^2$, $R^3$, $R^4$, $R^5$, $R^6$, $R^7$, $R^8$, $R^9$, $R^{10}$, $R^{11}$, and $R^{12}$ are each independently hydrogen, alkyl, alkenyl, alkynyl, aryl, alkaryl, aralkyl, halo, hydroxyl, sulthydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, derivatives thereof, any substituted or unsubstituted, and combinations thereof; and $R^{13}$ is a 1-membered to 24-membered (e.g., $C_1$-$C_{24}$) straight aliphatic or branched aliphatic, which can be substituted or unsubstituted, any with or without hetero atoms.

In some embodiments: ring A is a cycloaliphatic with 3-6 ring atoms, hetero cycloaliphatic with 3-6 ring atoms, or combinations thereof, which can be substituted or unsubstituted; ring B is a hetero cycloaliphatic with 3-6 ring atoms, which can be substituted or unsubstituted; ring D is a cyclopentapyridine; $X^1$ and $X^2$ are N; $X^3$ is O or NH; $X^4$ is NH, $CH_2$, O, or S; $X^5$ is O or S; $X^6$, $X^7$, $X^8$, $X^9$, $X^{10}$, $X^{11}$, and/or $X^{12}$ is CH or N; $X^{13}$ is N; $X^{14}$ is O or NH; and the $R^1$, $R^2$, $R^3$, $R^4$, $R^5$, $R^6$, $R^7$, $R^8$, $R^9$, $R^{10}$, $R^{11}$, and $R^{12}$ are each independently any one or more of the substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulthydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, isocyano, cyanato, isocyanato, thiocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonate, $C_1$-$C_{24}$ alkylsulfanyl, $C_5$-$C_{20}$ arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, any with or without hetero atoms, any substituted or unsubstituted, derivatives thereof, and combinations thereof; and $R^{13}$ is a 1-membered to 12-membered (e.g., $C_1$-$C_{12}$) straight aliphatic or branched aliphatic, which can be substituted or unsubstituted, any with or without hetero atoms.

In some embodiments, $R^1$, $R^2$, $R^3$, $R^4$, $R^5$, $R^6$, $R^7$, $R^8$, $R^9$, $R^{10}$, $R^{11}$, and $R^{12}$ are each independently H, F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., acetyl, $CH_3C{=}O$), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl.

In some embodiments, $R^{13}$ is methyl, ethyl, propyl, butyl, pentyl, hexyl, heptyl, octyl, isopropyl, tert-butyl, or $-C(R^{14})_2$, wherein each $R^{14}$ is independently a methyl, ethyl, propyl, butyl, pentyl, hexyl, heptyl, octyl, nonanyl, decanyl, undecanyl, or dodecanyl.

In these formulae and others provided herein, $X^4$ is a carbon or a hetero atom with or without a substituent; and $X^5$ is a hetero atom. In some aspects, $X^4$ is C (e.g., CH, $CH_2$) or N (e.g., N, NH, $NR^1$, $NOR^1$), any with or without a substituent (e.g., $R^1$); and $X^5$ is a O or N (e.g., NH, $NR^1$, $NOR^1$). Here, $R^1$ is as defined herein, where H, OH, methyl, ethyl, trifluoromethyl are examples. The $X^4$ can be C, NH or NOH, or $NOR^1$. $X^5$ is a O or $NR^1$, or $NOR^1$.

In some embodiments, the kinase inhibitor (e.g., TNIK kinase and/or MAP4K4 kinase) can include a structure of one of Formulae 4B-4K or 5B-5K, or derivative thereof, prodrug thereof, salt thereof, stereoisomer thereof, tautomer thereof, polymorph thereof, or solvate thereof, or having any chirality at any chiral center.

Formula 4B

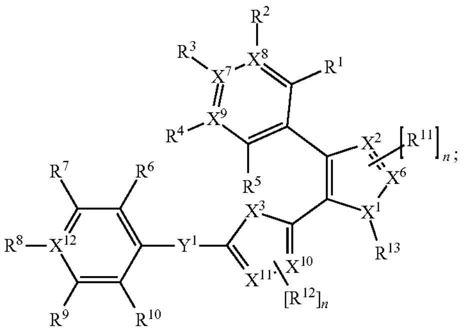

Formula 5B

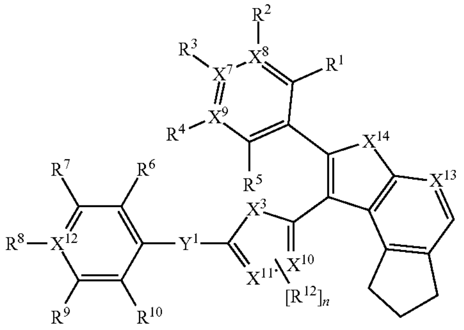

Formula 4C

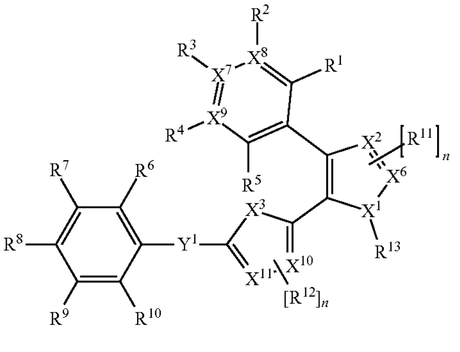

-continued
Formula 5C
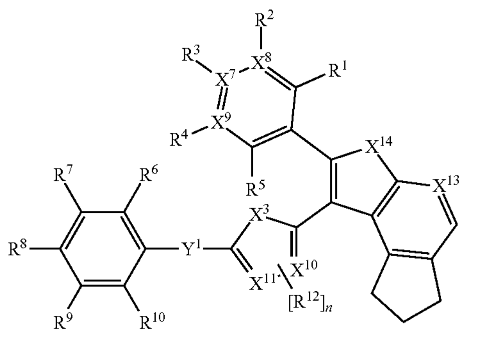
Formula 4D
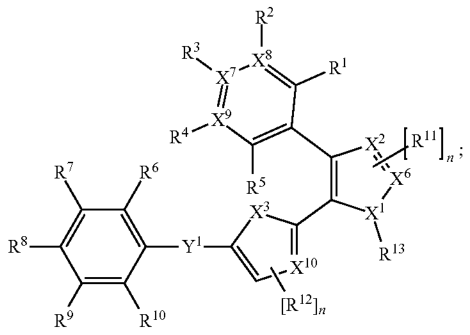
Formula 5D
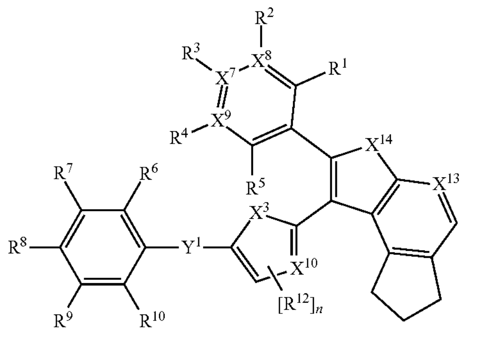
Formula 4E
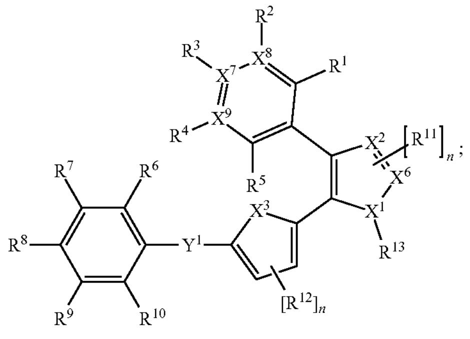
-continued
Formula 5E
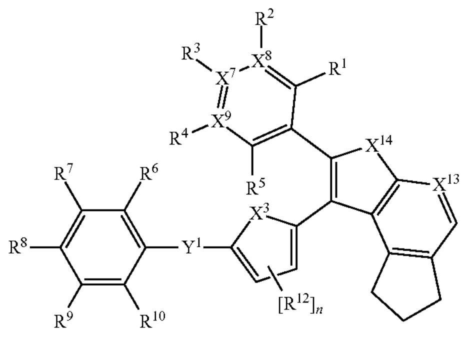
Formula 4F
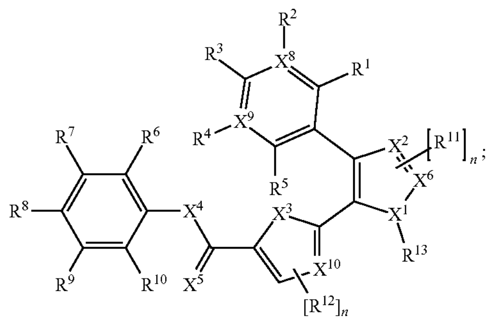
Formula 5F
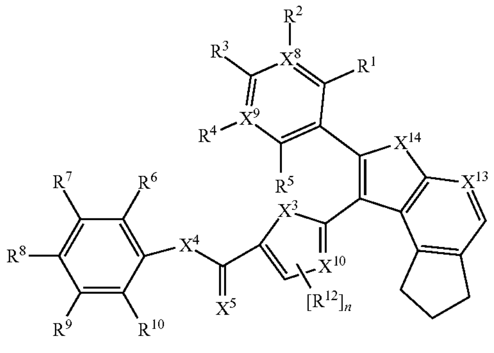
Formula 4G
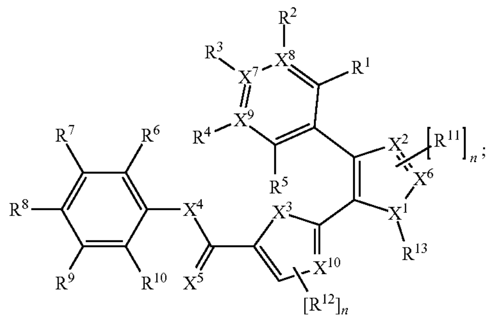

Formula 5G
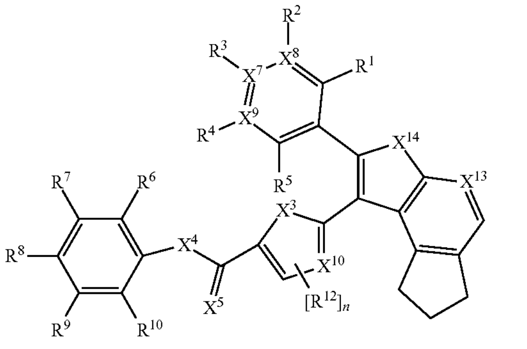
Formula 4H
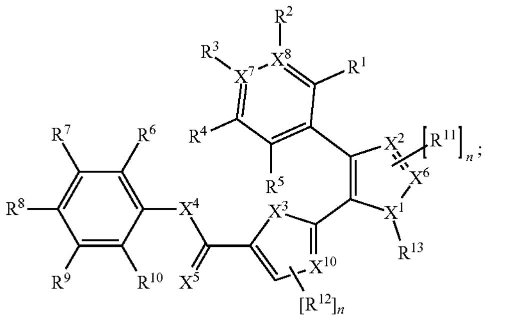
Formula 5H
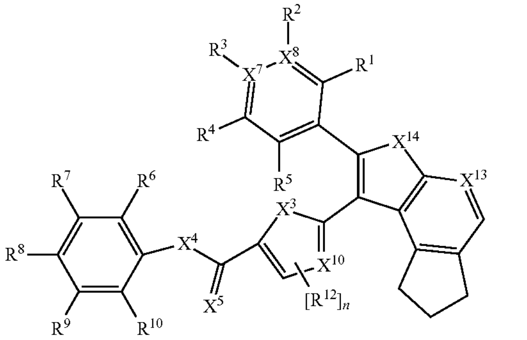
Formula 4I
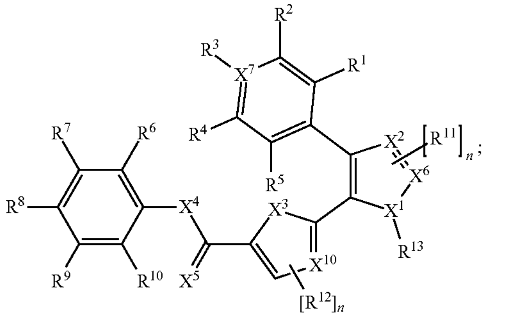
Formula 5I
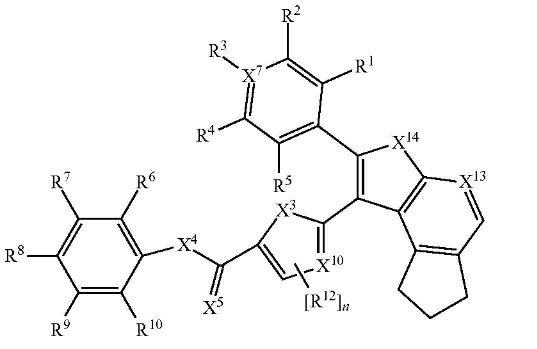
Formula 4J
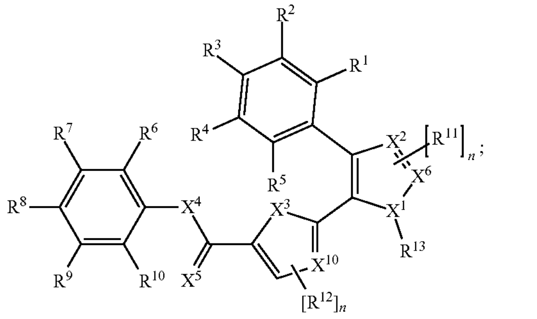
Formula 5J
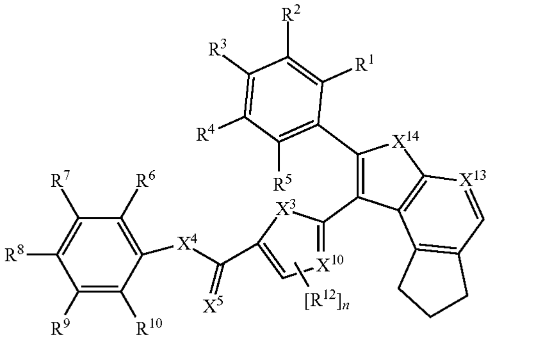
Formula 4K
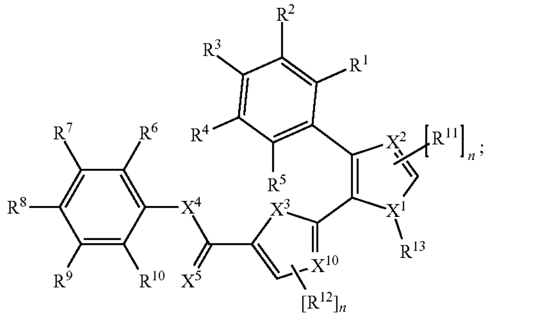

-continued

Formula 5K

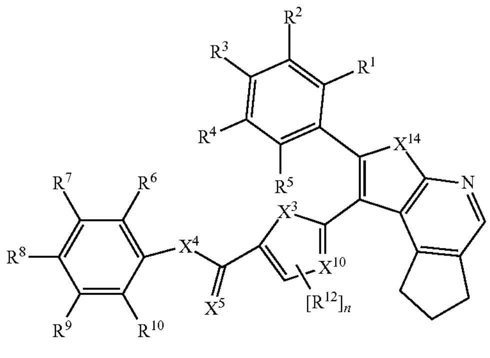

In some embodiments, ring A can be any ring structure with a single ring or two or more fused rings, which can be cycloaliphatic, hetero cycloaliphatic, aryl, hetero aryl, polyaryl, poly hetero aryl, or combinations thereof with 4, 5, 6, 7, 8, 9, 10, 11, or 12 atoms. When including hetero atoms, they can be C, N, or S and depend on the number of bonds therewith, and any ring A can include 1, 2, 3, 4, 5, 6 or more hetero atoms. Ring A can be substituted with one or more R groups, which can be the same as defined for any other R group. The number of R group substituents for ring A can be determined by the number of atoms in the ring when single rings being n−1 where n is the number of ring atoms. Each R group substituent on a ring can be different from the others.

In some embodiments, ring A represents a 5- or 6-membered cycloaliphatic or hetero cycloaliphatic, or combinations thereof, which may be substituted or unsubstituted. This can include a cyclopentyl or cyclohexyl, which may be substituted or unsubstituted.

In some embodiments, the X ring atoms can be carbon (C) or a hetero atom, such as 0, N, or S, or other. As noted, when carbon, the X ring atom may or may not have a substituent, such as shown by as $R^{11}$ and $R^{12}$, which can be on any atom of the respective ring, such as on the X ring atom, if present, such as in $X^1$, $X^2$, $X^3$, $X^6$, $X^{10}$ and $X^{11}$. As such, $X^1$ can be a C (e.g., CH) or N, with the appropriate hydrogen atoms. The $X^2$ can be a C (e.g., CH) or N, with the appropriate hydrogen atoms. The $X^3$ can be a C (e.g., $CH_2$) or NH, O or S. The $X^4$ can be a C (e.g., $CH_2$) or NH, O or S. The $X^5$ can be O or S. In some aspects, $Y^1$ can be linker Y. In some aspects, $X^4$ is C (e.g., CH, $CH_2$) or N (e.g., N, NH, $NR^1$, $NOR^1$), any with or without a substituent (e.g., $R^1$); and $X^5$ is a 0 or N (e.g., NH, $NR^1$, $NOR^1$). Here, $R^1$ is as defined herein, where H, OH, methyl, ethyl, trifluoromethyl are examples. The $X^4$ can be C, NH or NOH, or $NOR^1$. $X^5$ is a O or $NR^1$, or $NOR^1$.

In some embodiments, $Y^1$ can be linker Y when it is a chemical moiety more than just a bond, and the Y can be any linker, such as a chemical moiety or a bond. In some instances, Y is a bond, but most often is a chemical moiety. When Y is one chain atom or more than one chain atom, there may be at least one $R^{13}$ on one or more of the chain atoms, with $R^{13}$ can be any R group as defined herein. The linker can be O, S, $CH_2$, NH, or a hydrocarbon chain with or without hetero atoms, such as those recited herein for the X ring atoms. The linker may include O, S, $CH_2$, NH, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, derivatives thereof, substituted or unsubstituted, or combinations. In some aspects, the liker can include $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, any substituted or unsubstituted, derivatives thereof, and combinations thereof. In some instances, Y is the linker substituted with at least one $R^{13}$, which can be a substituent as described herein.

In some embodiments, each $R^1$, $R^2$, $R^3$, $R^4$, $R^5$, $R^6$, $R^7$, $R^8$, $R^9$, $R^{10}$, $R^{11}$, and $R^{12}$ are independently any one or more of the substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulthydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato ($—COO^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), di-substituted arylcarbamoyl (—(CO)—NH-aryl)$_2$, thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-substituted arylthiocarbamoyl (—(CS)—NH-aryl), di-substituted arylthiocarbamoyl (—(CS)—NH-aryl)$_2$, carbamido (—NH—(CO)—$NH_2$), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)$_2$), mono-substituted aryl carbamido (—NH—(CO)—NH-aryl), di-substituted aryl carbamido (—NH—(CO)—N-(aryl)$_2$) cyano (—C≡N), isocyano ($—N+=C^-$), cyanato (—O—CN), isocyanato ($—O—N^+≡C^-$), thiocyanato (—S—C≡N) isothiocyanato ($—S—N^+≡C^-$), azido ($—N=N^+=N^-$), formyl (—(CO)—H), thioformyl (—(CS)—H), amino (—$NH_2$), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, $C_1$-$C_{24}$ alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfonic acid (—$SO_2$—OH), sulfonato ($—SO_2—O^-$)$^-$ $C_1$-$C_{24}$ alkylsulfanyl (—S-alkyl; also termed "alkylthio"), $C_5$-$C_{20}$ arylsulfanyl (—S-aryl; also termed "arylthio"), $C_1$-$C_{24}$ alkylsulfinyl (—(SO)-alkyl), $C_5$-$C_{50}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato ($—P(O)(O^-)_2$), phosphinato (—P(O)(O—)), phospho (—$PO_2$), phosphino (—$PH_2$), any with or without hetero atoms (e.g., N, O, S, or other) where the hetero atoms can be substituted (e.g., hetero atom substituted for carbon in chain or ring) for the carbons or in addition thereto (e.g., hetero atom added to carbon chain or ring) swapped, any including straight chains, any including branches, and any including rings, any being substituted or unsubstituted, derivatives thereof, and combinations thereof.

In some embodiments, the method uses a compound under Formula B or Formula B1, which ring C as defined herein, such as a $C_5$-$C_6$ ring structure (e.g., cycloaliphatic) with or without hetero atoms.

Formula B

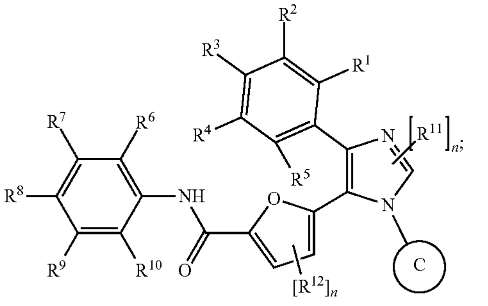

Formula B1

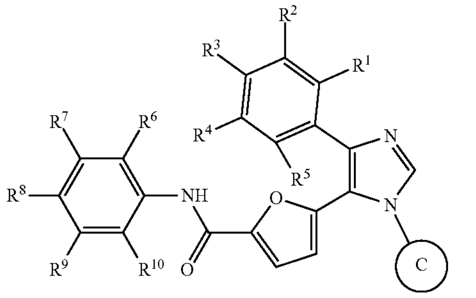

In some aspects: ring C is a $C_5$-$C_6$ aliphatic ring structure without hetero atoms; each $R^1$, $R^2$, $R^3$, $R^5$, $R^6$, $R^7$, $R^8$, $R^9$, $R^{10}$, $R^{11}$, and $R^{12}$ is independently a substituent; and n is 0, 1, or 2. In some aspects, ring C is a $C_5$-$C_6$ aliphatic ring structure without hetero atoms; and each $R^1$, $R^2$, $R^3$, $R^5$, $R^6$, $R^7$, $R^8$, $R^9$, and $R^{10}$ is independently a substituent with $R^{11}$, and $R^{12}$ is nothing or hydrogen.

In some embodiments, the compound has the structure of Formulae 7, 8, 9, 10, 11, 12, 13, or 14, derivative thereof, prodrug thereof, salt thereof, stereoisomer thereof, tautomer thereof, polymorph thereof, or solvate thereof, or having any chirality at any chiral center, Formula 7

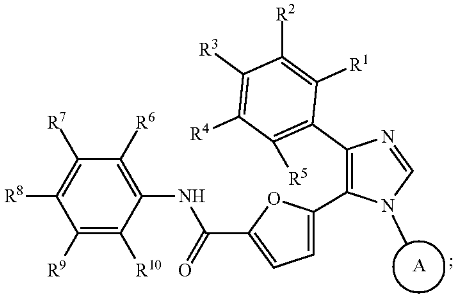

-continued

Formula 8

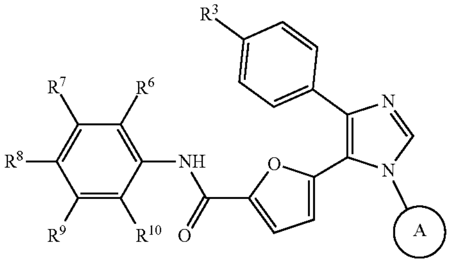

Formula 9

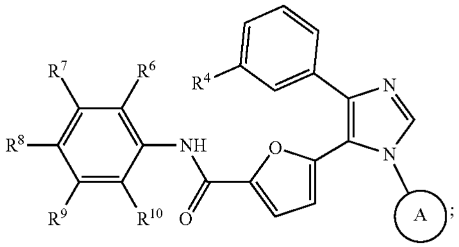

Formula 10

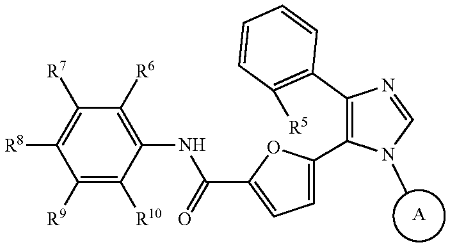

Formula 11

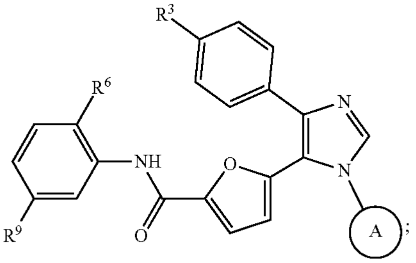

Formula 12

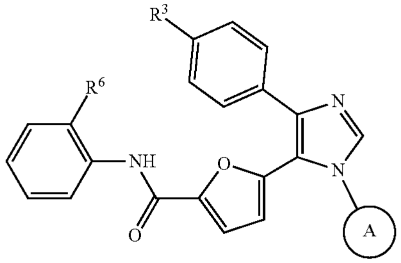

Formula 13

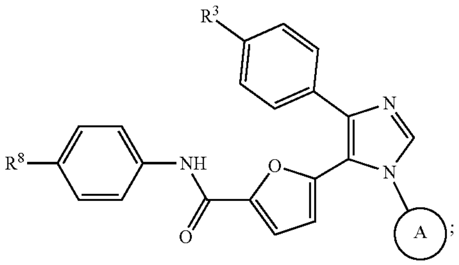

-continued

Formula 14

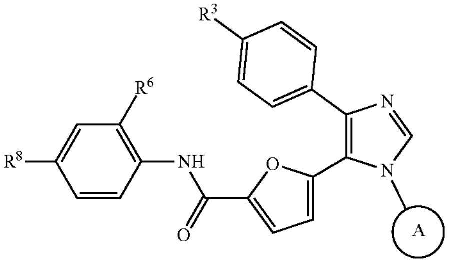

In some embodiments, in any of the formulae, the $R^1$, $R^2$, $R^3$, $R^4$, $R^5$, $R^6$, $R^7$, $R^8$, $R^9$, $R^{10}$, $R^{11}$, and $R^{12}$ substituents, can each be independently H, F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., acetyl, $CH_3C{=}O$), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl.

In some embodiments, the $R^1$, $R^2$, $R^3$, $R^4$, $R^5$, $R^6$, $R^7$, $R^8$, $R^9$, $R^{10}$, $R^{11}$, and $R^{12}$ are each independently halogen, alkyl, branched alkyl, alkoxy, alkyl ester, alkylsuflanyl (i.e., thioalkyl), acetyl, (trifluoroalkyl)oxy, trifluoroalkyl, or acetamide (i.e., acetylamino).

In some embodiments, the compound includes at least one of the following: $R^3$ being a substituent; $R^6$ being a substituent; $R^7$ being a substituent; $R^8$ being a substituent; $R^9$ being a substituent; and/or $R^{10}$ being a substituent. The rest of the R groups can be hydrogen or nothing. This can apply to all formula recited herein.

In some embodiments, the compound includes at least one of the following: $R^3$ being F; $R^6$ being F, Br, Cl, methoxy, or methyl ester; $R^7$ being F or methoxy; $R^8$ being F methoxy, or methyl; $R^9$ being F or methoxy; and/or $R^{10}$ being F, Br, Cl, methoxy, or methyl ester. The rest of the R groups can be hydrogen or nothing. This can apply to all formula recited herein.

In some embodiments, the compound includes the following: $R^3$ being F; and $R^1$, $R^2$, $R^4$, and $R^5$ being H. The rest of the R groups can be hydrogen or nothing. This can apply to all formula recited herein.

In some embodiments, the compound includes one of the following: $R^6$ and $R^9$ having the substituent, and $R^7$, $R^8$, and $R^{10}$ being H; $R^7$ and $R^{10}$ having the substituent, and $R^6$, $R^8$, and $R^9$ being H; $R^6$ having the substituent, and $R^7$, $R^8$, $R^9$, and $R^{10}$ being H; $R^8$ having the substituent, and $R^6$, $R^7$, $R^9$, and $R^{10}$ being H; $R^{10}$ having the substituent, and $R^6$, $R^7$, $R^8$, and $R^9$ being H; $R^6$ and $R^8$ having the substituent, and $R^7$, $R^9$, and $R^{10}$ being H; or $R^8$ and $R^{10}$ having the substituent, and $R^6$, $R^7$, and $R^9$ being H. The rest of the R groups can be hydrogen or nothing. This can apply to all formula recited herein.

In some embodiments, the compound includes the following: $R^3$ being F; $R^1$, $R^2$, $R^4$, and $R^5$ being H; $R^6$ being F, Br, Cl, methoxy, or methyl ester; $R^9$ being F or methoxy; and $R^7$, $R^8$, and $R^{10}$ being H. The rest of the R groups can be hydrogen or nothing. This can apply to all formula recited herein.

In some embodiments, the compound includes the following: $R^3$ being F; $R^1$, $R^2$, $R^4$, and $R^5$ being H; $R^6$ being F, Br, Cl, methoxy, or methyl ester; and $R^7$, $R^8$, $R^9$, and $R^{10}$ being H. The rest of the R groups can be hydrogen or nothing. This can apply to all formula recited herein.

In some embodiments, the compound includes the following: $R^3$ being F; $R^1$, $R^2$, $R^4$, and $R^5$ being H; $R^8$ being F methoxy, or methyl; and $R^6$, $R^7$, $R^9$, and $R^{10}$ being H. The rest of the R groups can be hydrogen or nothing. This can apply to all formula recited herein.

In some embodiments, the compound includes the following: $R^3$ being F; $R^1$, $R^2$, $R^4$, and $R^5$ being H; $R^{10}$ being F, Br, Cl, methoxy, or methyl ester, and $R^6$, $R^7$, $R^8$, and $R^9$ being H. The rest of the R groups can be hydrogen or nothing. This can apply to all formula recited herein.

In some embodiments, the compound includes the following: $R^3$ being F; $R^1$, $R^2$, $R^4$, and $R^5$ being H; $R^6$ being F, Br, Cl, methoxy, or methyl ester; $R^8$ being F methoxy, or methyl; and $R^7$, $R^9$, and $R^{10}$ being H. The rest of the R groups can be hydrogen or nothing. This can apply to all formula recited herein.

In some embodiments, the inhibitor compound (e.g., TNIK kinase inhibitor and/or MAP4K4 kinase inhibitor) used in the methods can be one of the following:

Compound 1

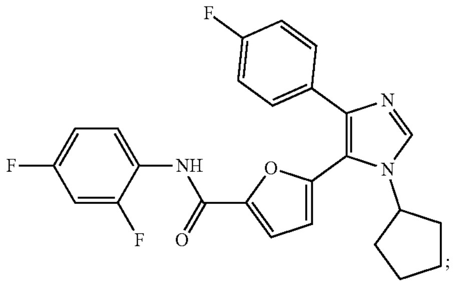

5-(1-cyclopentyl-4-(4-fluorophenyl)-1H-imidazol-5-yl)-N-(2,4-difluorophenyl)furan-2-carboxamide Compound 2

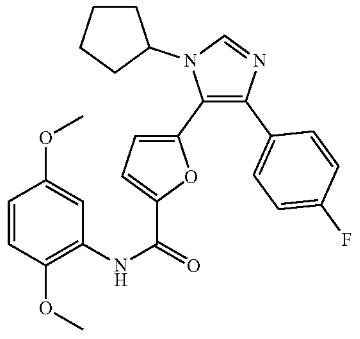

5-(1-cyclopentyl-4-(4-fluorophenyl)-1H-imidazol-5-yl)-N-(2,5-dimethoxyphenyl)furan-2-carboxamide -continued Compound 3

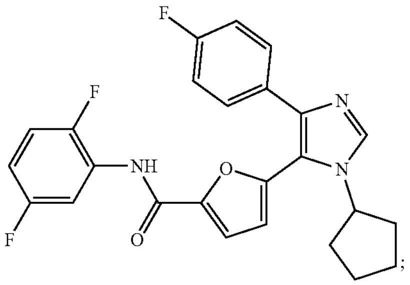

5-(1-cyclopentyl-4-(4-fluorophenyl)-1H-imidazol-5-yl)-N-(2,5-difluorophenyl)furan-2-carboxamide Compound 4

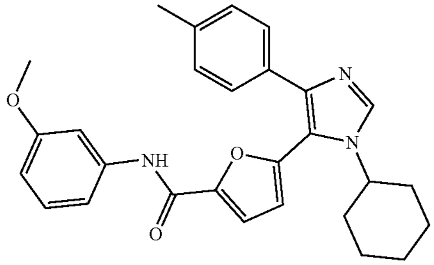

5-(1-cyclohexyl-4-(p-tolyl)-1H-imidazol-5-yl)-N-(3-methoxyphenyl)furan-2-carboxamide Compound 5

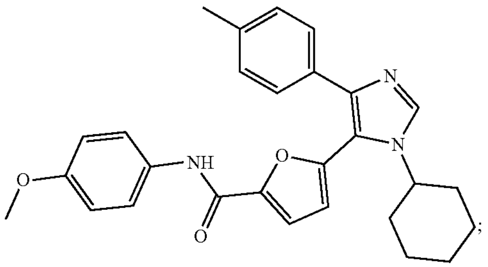

5-(1-cyclohexyl-4-(p-tolyl)-1H-imidazol-5-yl)-N-(4-methoxyphenyl)furan-2-carboxamide Compound 6

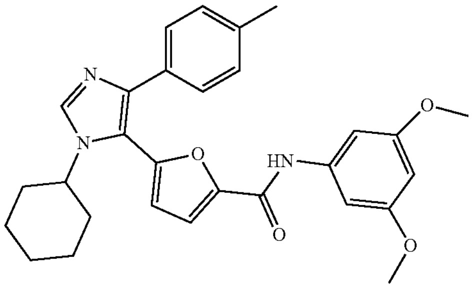

5-(1-cyclohexyl-4-(p-tolyl)-1H-imidazol-5-yl)-N-(3,5-dimethoxyphenyl)furan-2-carboxamide -continued Compound 7

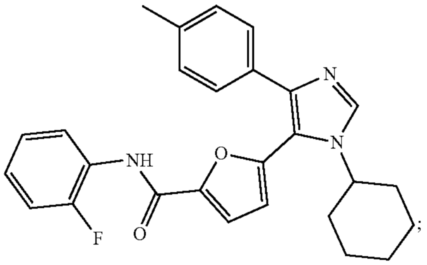

5-(1-cyclohexyl-4-(p-tolyl)-1H-imidazol-5-yl)-N-(2-fluorophenyl)furan-2-carboxamide Compound 8

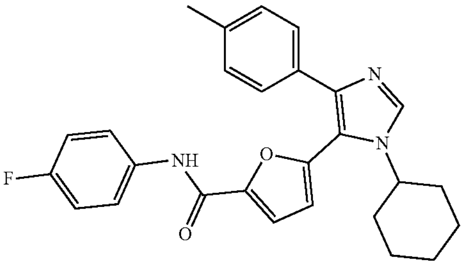

5-(1-cyclohexyl-4-(p-tolyl)-1H-imidazol-5-yl)-N-(4-fluorophenyl)furan-2-carboxamide Compound 9

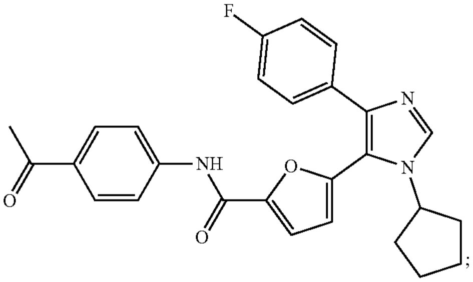

N-(4-acetylphenyl)-5-(1-cyclopentyl-4-(4-fluorophenyl)-1H-imidazol-5-yl)furan-2-carboxamide Compound 10

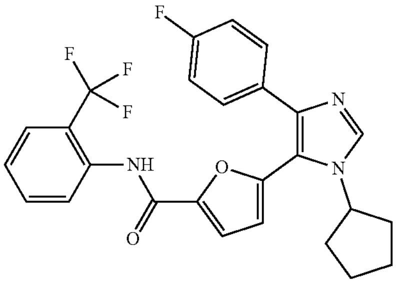

5-(1-cyclopentyl-4-(4-fluorophenyl)-1H-imidazol-5-yl)-N-(2-(trifluoromethyl)phenyl)furan-2-carboxamide -continued Compound 11

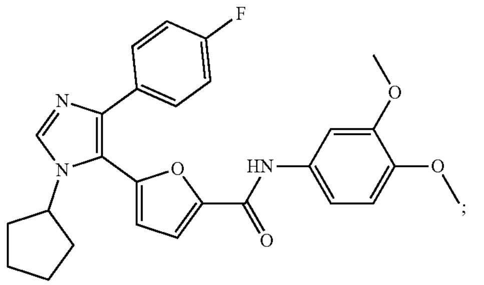

5-(1-cyclopentyl-4-(4-fluorophenyl)-1H-imidazol-5-yl)-N-(3,4-dimethoxyphenyl)furan-2-carboxamide Compound 12

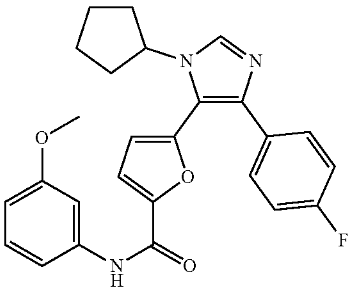

5-(1-cyclopentyl-4-(4-fluorophenyl)-1H-imidazol-5-yl)-N-(3-methoxyphenyl)furan-2-carboxamide Compound 13

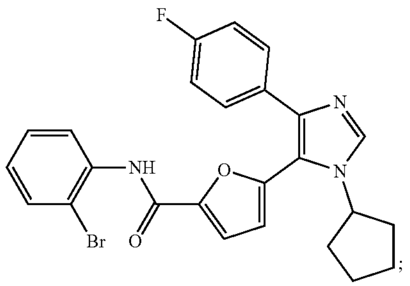

N-(2-bromophenyl)-5-(1-cyclopentyl-4-(4-fluorophenyl)-1H-imidazol-5-yl)furan-2-carboxamide Compound 14

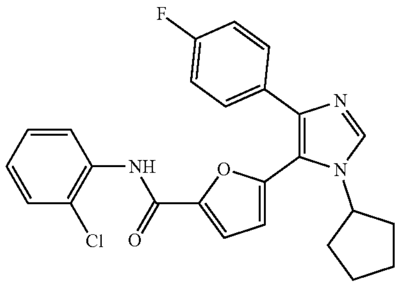

N-(2-chlorophenyl)-5-(1-cyclopentyl-4-(4-fluorophenyl)-1H-imidazol-5-yl)furan-2-carboxamide -continued Compound 15

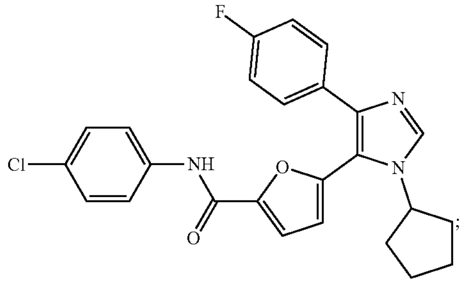

N-(4-chlorophenyl)-5-(1-cyclopentyl-4-(4-fluorophenyl)-1H-imidazol-5-yl)furan-2-carboxamide Compound 16

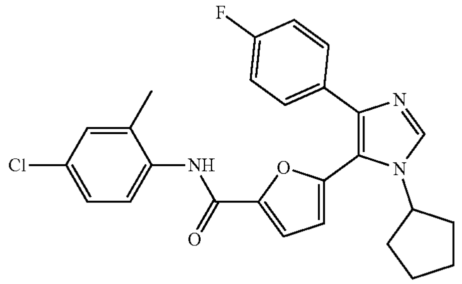

N-(4-chloro-2-methylphenyl)-5-(1-cyclopentyl-4-(4-fluorophenyl)-1H-imidazol-5-yl)furan-2-carboxamide Compound 17

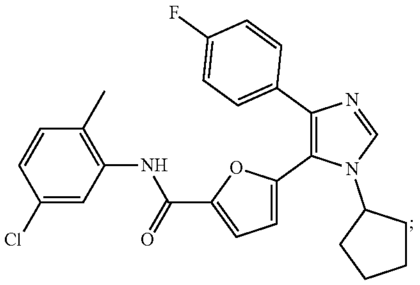

N-(5-chloro-2-methylphenyl)-5-(1-cyclopentyl-4-(4-fluorophenyl)-1H-imidazol-5-yl)furan-2-carboxamide Compound 18

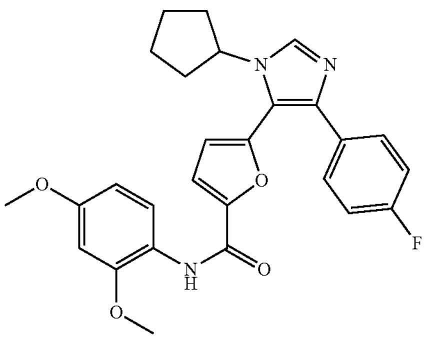

5-(1-cyclopentyl-4-(4-fluorophenyl)-1H-imidazol-5-yl)-N-(2,4-dimethoxyphenyl)furan-2-carboxamide Compound 19

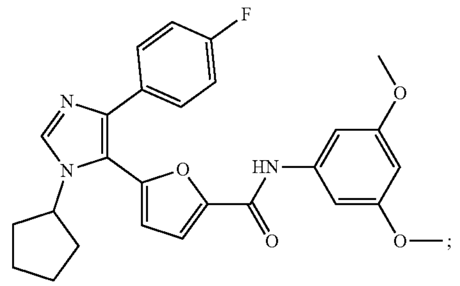

5-(1-cyclopentyl-4-(4-fluorophenyl)-1H-imidazol-5-yl)-N-(3,5-dimethoxyphenyl)furan-2-carboxamide Compound 20

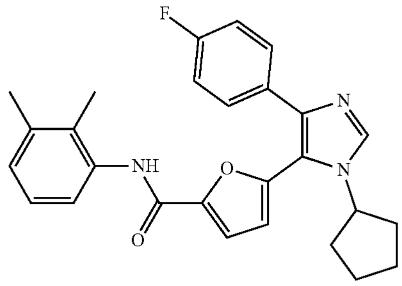

5-(1-cyclopentyl-4-(4-fluorophenyl)-1H-imidazol-5-yl)-N-(2,3-dimethylphenyl)furan-2-carboxamide Compound 21

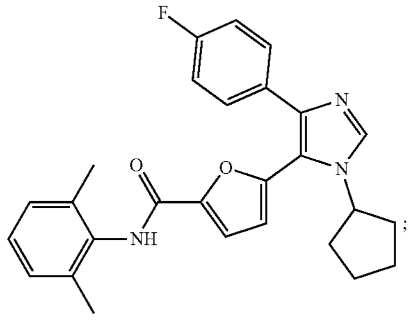

5-(1-cyclopentyl-4-(4-fluorophenyl)-1H-imidazol-5-yl)-N-(2,6-dimethylphenyl)furan-2-carboxamide Compound 22

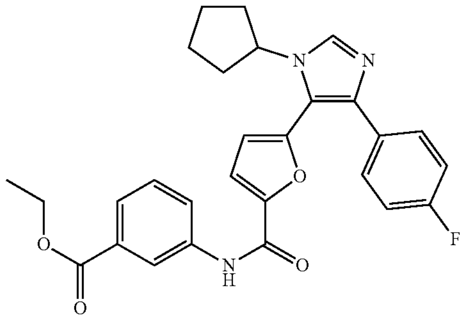

ethyl 3-(5-(1-cyclopentyl-4-(4-fluorophenyl)-1H-imidazol-5-\yl)furan-2-carboxamido)benzoate Compound 23

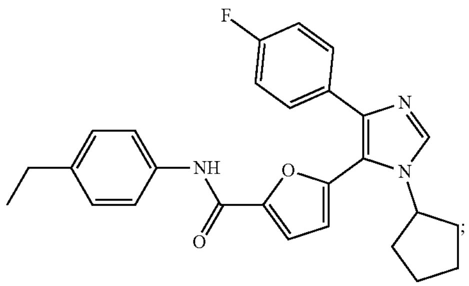

5-(1-cyclopentyl-4-(4-fluorophenyl)-1H-imidazol-5-yl)-N-(4-ethylphenyl)furan-2-carboxamide Compound 24

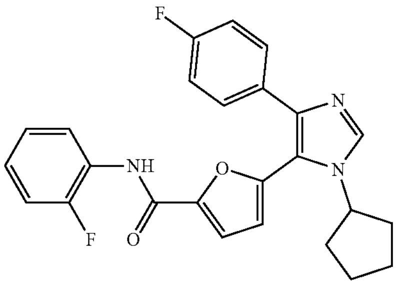

5-(1-cyclopentyl-4-(4-fluorophenyl)-1H-imidazol-5-yl)-N-(2-fluorophenyl)furan-2-carboxamide Compound 25

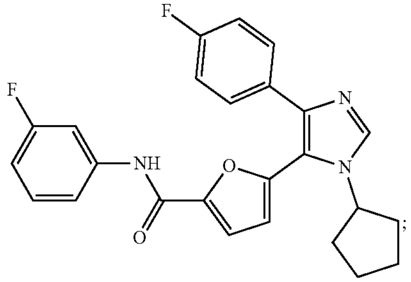

5-(1-cyclopentyl-4-(4-fluorophenyl)-1H-imidazol-5-yl)-N-(3-fluorophenyl)furan-2-carboxamide Compound 26

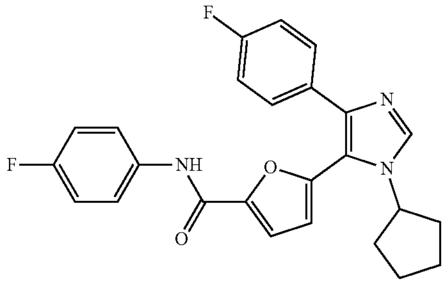

5-(1-cyclopentyl-4-(4-fluorophenyl)-1H-imidazol-5-yl)-N-(4-fluorophenyl)furan-2-carboxamide -continued Compound 27

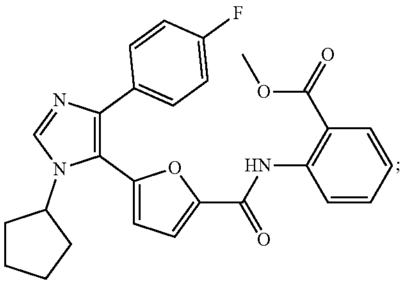

methyl 2-(5-(1-cyclopentyl-4-(4-fluorophenyl)-1H-imidazol-5-yl)furan-2-carboxamido)benzoate Compound 28

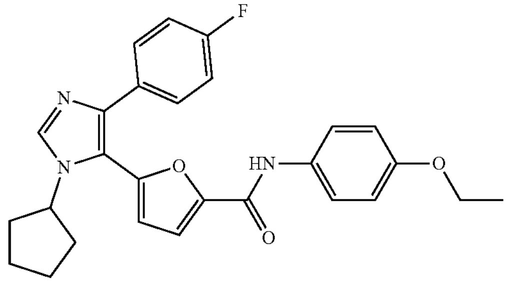

5-(1-cyclopentyl-4-(4-fluorophenyl)-1H-imidazol-5-yl)-N-(4-ethoxyphenyl)furan-2-carboxamide Compound 29

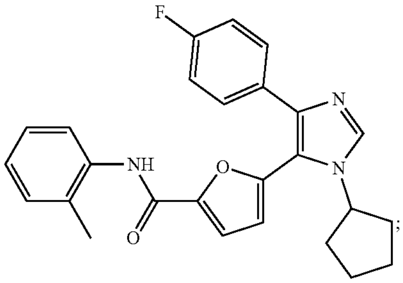

5-(1-cyclopentyl-4-(4-fluorophenyl)-1H-imidazol-5-yl)-N-(o-tolyl)furan-2-carboxamide Compound 30

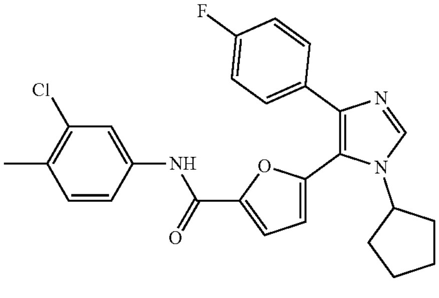

N-(3-chloro-4-methylphenyl)-5-(1-cyclopentyl-4-(4-fluorophenyl)-1H-imidazol-5-yl)furan-2-carboxamide -continued Compound 31

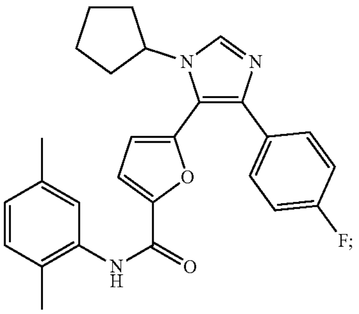

5-(1-cyclopentyl-4-(4-fluorophenyl)-1H-imidazol-5-yl)-N-(2,5-dimethylphenyl)furan-2-carboxamide Compound 32

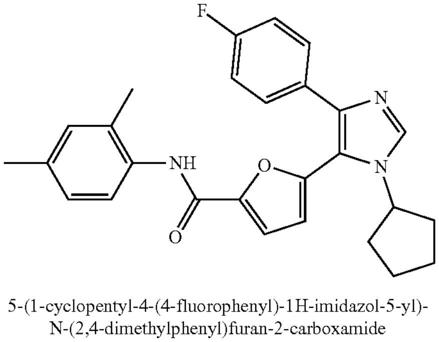

5-(1-cyclopentyl-4-(4-fluorophenyl)-1H-imidazol-5-yl)-N-(2,4-dimethylphenyl)furan-2-carboxamide Compound 33

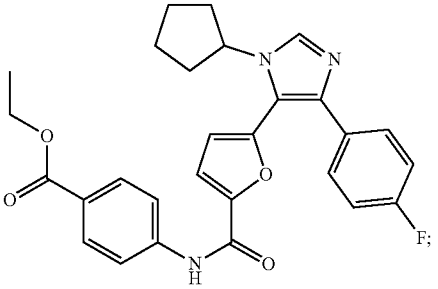

ethyl 4-(5-(1-cyclopentyl-4-(4-fluorophenyl)-1H-imidazol-5-yl)furan-2-carboxamido)benzoate Compound 34

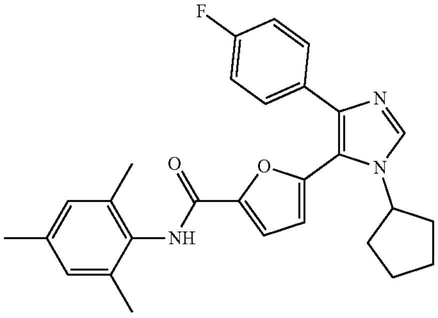

5-(1-cyclopentyl-4-(4-fluorophenyl)-1H-imidazol-5-yl)-N-mesitylfuran-2-carboxamide -continued Compound 35

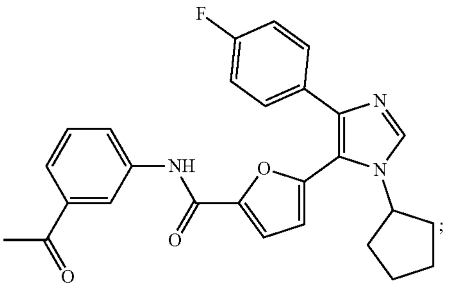

N-(3-acetylphenyl)-5-(1-cyclopentyl-4-(4-fluorophenyl)-1H-imidazol-5-yl)-furan-2-carboxamide Compound 36

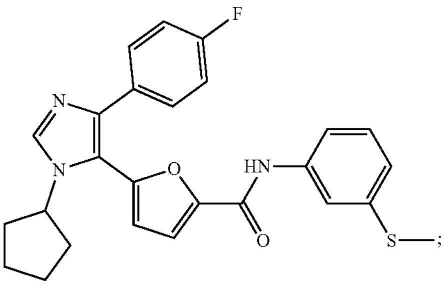

5-(1-cyclopentyl-4-(4-fluorophenyl)-1H-imidazol-5-yl)-N-(3-(methylthio)phenyl)furan-2-carboxamide Compound 37

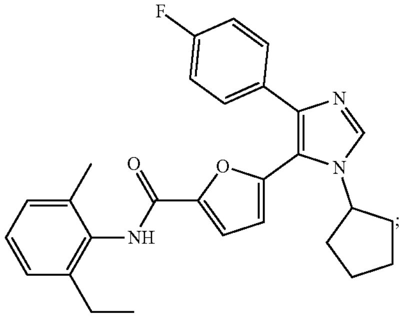

5-(1-cyclopentyl-4-(4-fluorophenyl)-1H-imidazol-5-yl)-N-(2-ethyl-6-methylphenyl)furan-2-carboxamide Compound 38

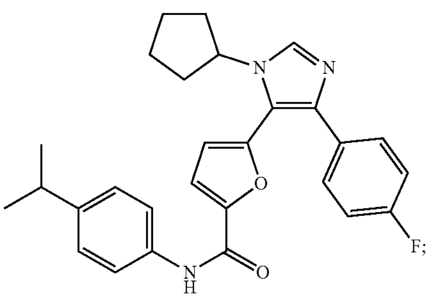

5-(1-cyclopentyl-4-(4-fluorophenyl)-1H-imidazol-5-yl)-N-(4-isopropylphenyl)furan-2-carboxamide -continued Compound 39

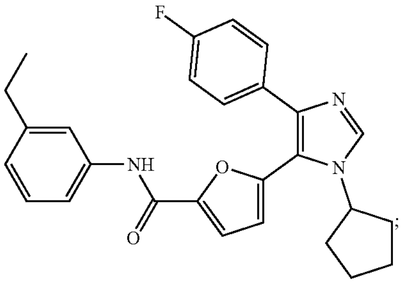

5-(1-cyclopentyl-4-(4-fluorophenyl)-1H-imidazol-5-yl)-N-(3-ethylphenyl)furan-2-carboxamide Compound 40

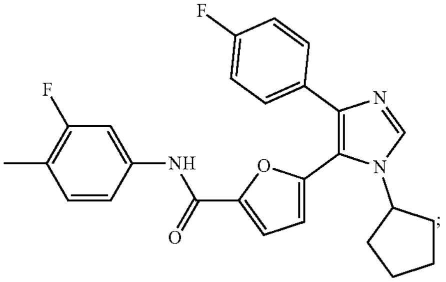

5-(1-cyclopentyl-4-(4-fluorophenyl)-1H-imidazol-5-yl)-N-(3-fluoro-4-methylphenyl)furan-2-carboxamide Compound 41

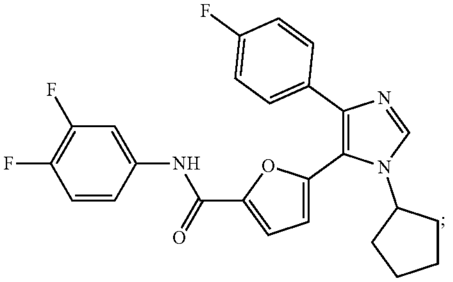

5-(1-cyclopentyl-4-(4-fluorophenyl)-1H-imidazol-5-yl)-N-(3,4-difluorophenyl)furan-2-carboxamide Compound 42

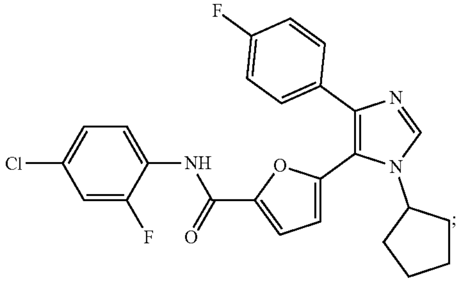

N-(4-chloro-2-fluorophenyl)-5-(1-cyclopentyl-4-(4-fluorophenyl)-1H-imidazol-5-yl)furan-2-carboxamide -continued Compound 43

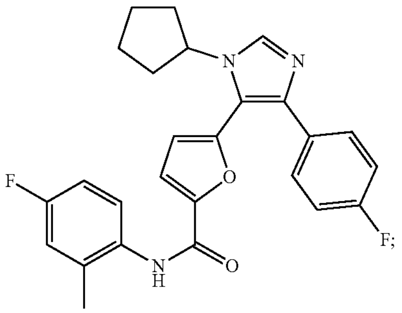

5-(1-cyclopentyl-4-(4-fluorophenyl)-1H-imidazol-5-yl)-N-(4-fluoro-2-methylphenyl)furan-2-carboxamide Compound 44

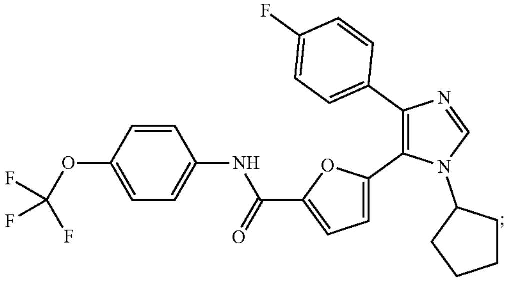

5-(1-cyclopentyl-4-(4-fluorophenyl)-1H-imidazol-5-yl)-N-(4-(trifluoromethoxy)phenyl)furan-2-carboxamide Compound 45

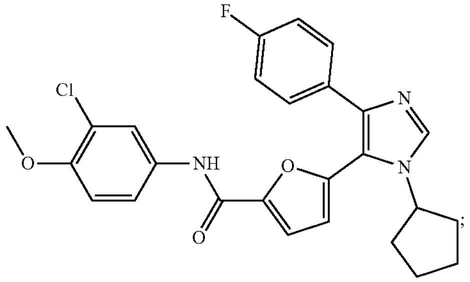

N-(3-chloro-4-methoxyphenyl)-5-(1-cyclopentyl-4-(4-fluorophenyl)-1H-imidazol-5-yl)furan-2-carboxamide Compound 46

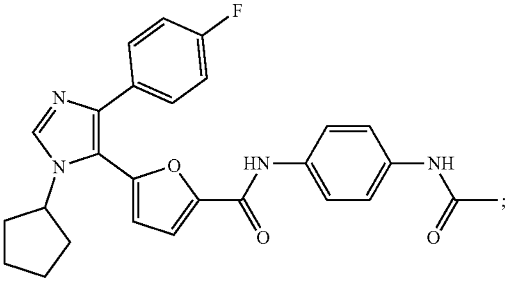

N-(4-acetamidophenyl)-5-(1-cyclopentyl-4-(4-fluorophenyl)-1H-imidazol-5-yl)furan-2-carboxamide -continued Compound 47

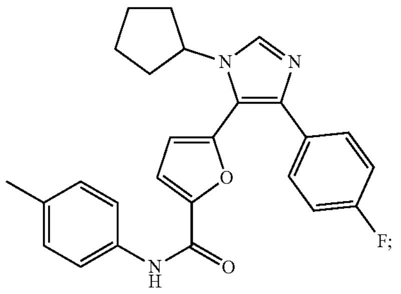

5-(1-cyclopentyl-4-(4-fluorophenyl)-1H-imidazol-5-yl)-N-(p-tolyl)furan-2-carboxamide Compound 48

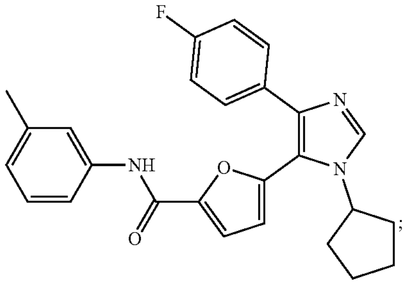

5-(1-cyclopentyl-4-(4-fluorophenyl)-1H-imidazol-5-yl)-N-(m-tolyl)furan-2-carboxamide Compound 49

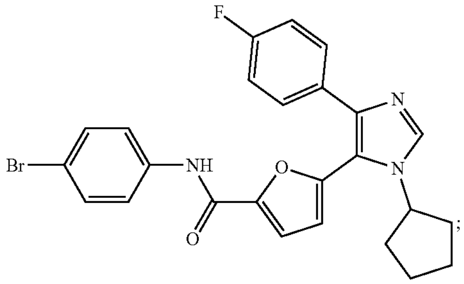

N-(4-bromophenyl)-5-(1-cyclopentyl-4-(4-fluorophenyl)-1H-imidazol-5-yl)furan-2-carboxamide Compound 50

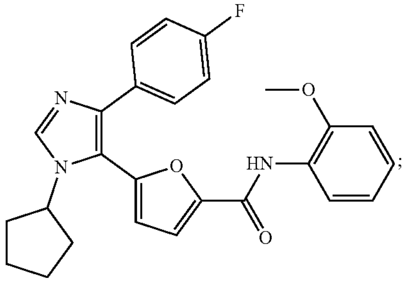

5-(1-cyclopentyl-4-(4-fluorophenyl)-1H-imidazol-5-yl)-N-(2-methoxyphenyl)furan-2-carboxamide -continued Compound 51

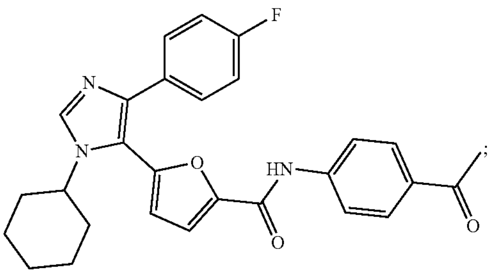

N-(4-acetylphenyl)-5-(1-cyclohexyl-4-(4-fluorophenyl)-1H-imidazol-5-yl)furan-2-carboxamide Compound 52

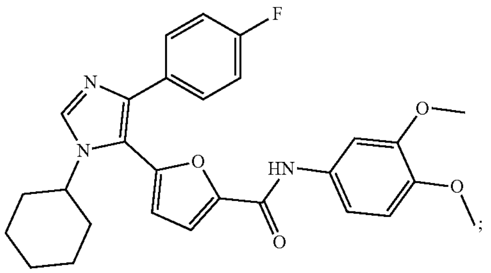

5-(1-cyclohexyl-4-(4-fluorophenyl)-1H-imidazol-5-yl)-N-(3,4-dimethoxyphenyl)furan-2-carboxamide Compound 53

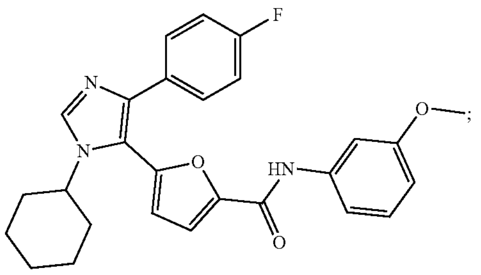

5-(1-cyclohexyl-4-(4-fluorophenyl)-1H-imidazol-5-yl)-N-(3-methoxyphenyl)furan-2-carboxamide Compound 54

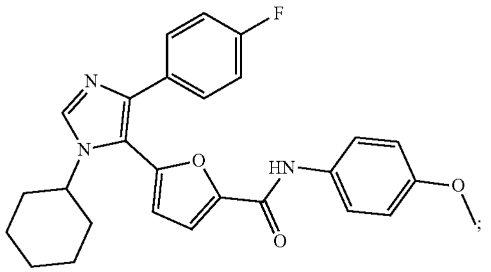

5-(1-cyclohexyl-4-(4-fluorophenyl)-1H-imidazol-5-yl)-N-(4-methoxyphenyl)furan-2-carboxamide -continued Compound 55

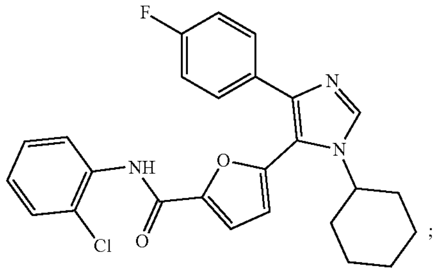

N-(2-chlorophenyl)-5-(1-cyclohexyl-4-(4-fluorophenyl)-1H-imidazol-5-yl)furan-2-carboxamide Compound 56

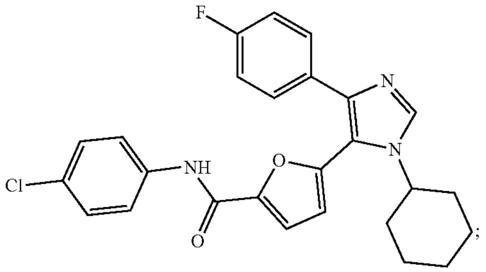

N-(4-chlorophenyl)-5-(1-cyclohexyl-4-(4-fluorophenyl)-1H-imidazol-5-yl)furan-2-carboxamide Compound 57

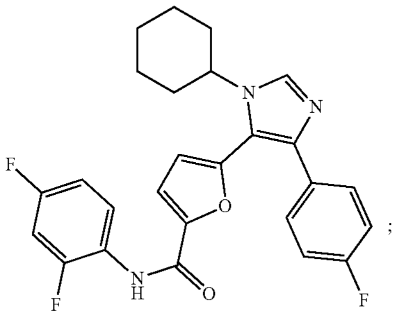

5-(1-cyclohexyl-4-(4-fluorophenyl)-1H-imidazol-5-yl)-N-(2,4-difluorophenyl)furan-2-carboxamide Compound 58

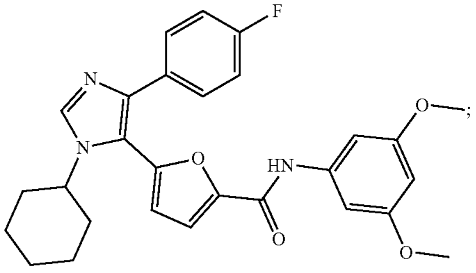

5-(1-cyclohexyl-4-(4-fluorophenyl)-1H-imidazol-5-yl)-N-(3,5-dimethoxyphenyl)furan-2-carboxamide -continued Compound 59

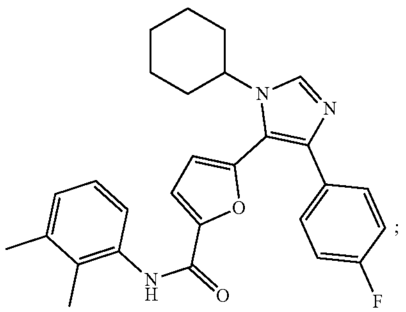

5-(1-cyclohexyl-4-(4-fluorophenyl)-1H-imidazol-5-yl)-N-(2,3-dimethylphenyl)furan-2-carboxamide Compound 60

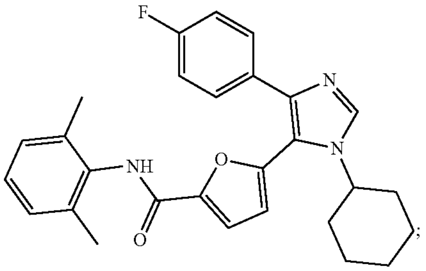

5-(1-cyclohexyl-4-(4-fluorophenyl)-1H-imidazol-5-yl)-N-(2,6-dimethylphenyl)furan-2-carboxamide Compound 61

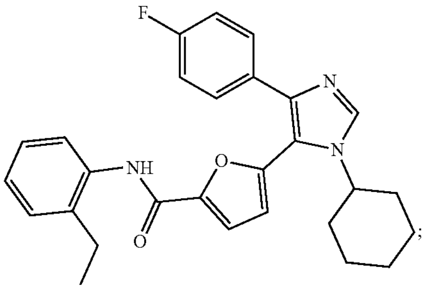

5-(1-cyclohexyl-4-(4-fluorophenyl)-1H-imidazol-5-yl)-N-(2-ethylphenyl)furan-2-carboxamide Compound 62

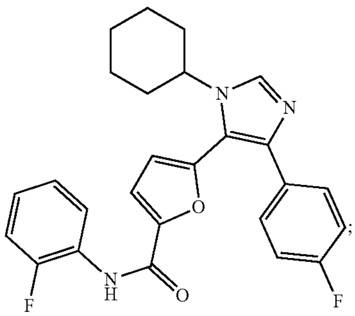

5-(1-cyclohexyl-4-(4-fluorophenyl)-1H-imidazol-5-yl)-N-(2-fluorophenyl)furan-2-carboxamide -continued Compound 63

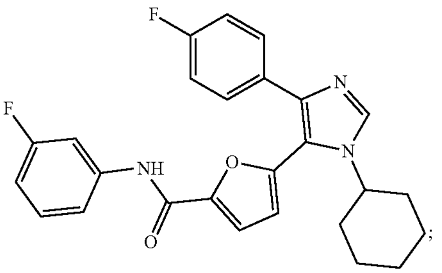

5-(1-cyclohexyl-4-(4-fluorophenyl)-1H-imidazol-5-yl)-N-(3-fluorophenyl)furan-2-carboxamide Compound 64

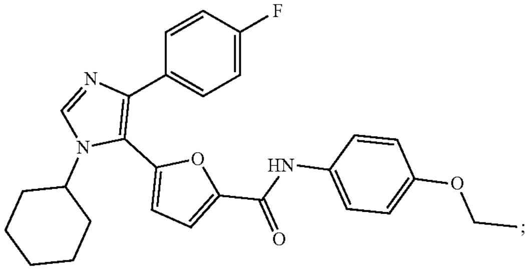

5-(1-cyclohexyl-4-(4-fluorophenyl)-1H-imidazol-5-yl)-N-(4-ethoxyphenyl)furan-2-carboxamide Compound 65

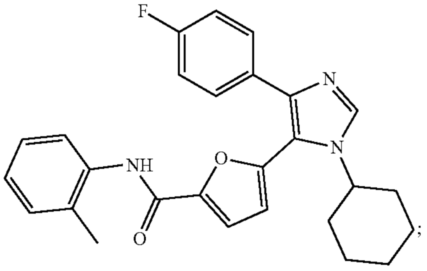

5-(1-cyclohexyl-4-(4-fluorophenyl)-1H-imidazol-5-yl)-N-(o-tolyl)furan-2-carboxamide Compound 66

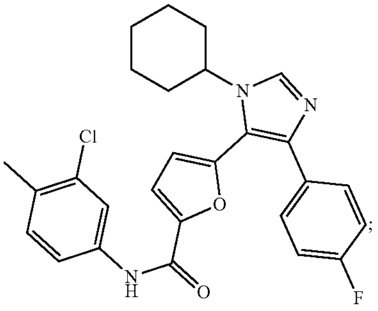

N-(3-chloro-4-methylphenyl)-5-(1-cyclohexyl-4-(4-fluorophenyl)-1H-imidazol-5-yl)furan-2-carboxamide -continued Compound 67

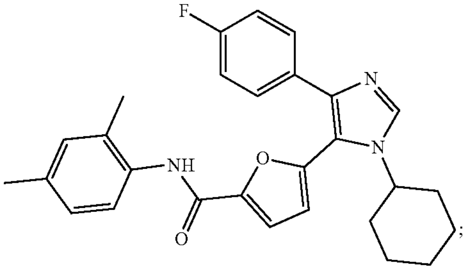

5-(1-cyclohexyl-4-(4-fluorophenyl)-1H-imidazol-5-yl)-N-(2,4-dimethylphenyl)furan-2-carboxamide Compound 68

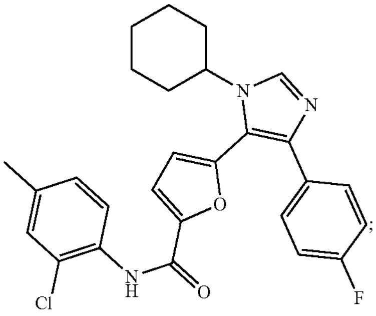

N-(2-chloro-4-methylphenyl)-5-(1-cyclohexyl-4-(4-fluorophenyl)-1H-imidazol-5-yl)furan-2-carboxamide Compound 69

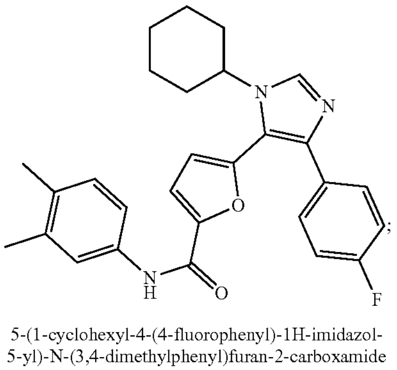

5-(1-cyclohexyl-4-(4-fluorophenyl)-1H-imidazol-5-yl)-N-(3,4-dimethylphenyl)furan-2-carboxamide Compound 70

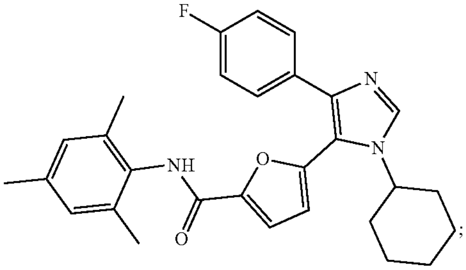

5-(1-cyclohexyl-4-(4-fluorophenyl)-1H-imidazol-5-yl)-N-mesitylfuran-2-carboxamide -continued Compound 71

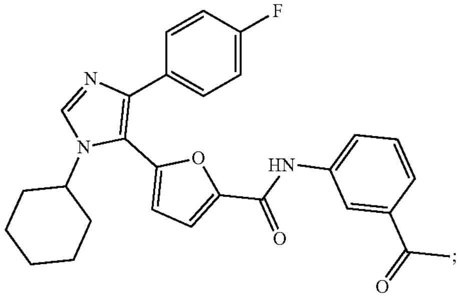

N-(3-acetylphenyl)-5-(1-cyclohexyl-4-(4-fluorophenyl)-1H-imidazol-5-yl)furan-2-carboxamide Compound 72

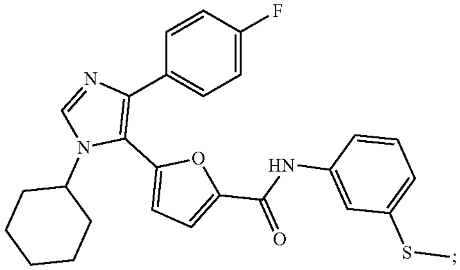

5-(1-cyclohexyl-4-(4-fluorophenyl)-1H-imidazol-5-yl)-N-(3-(methylthio)phenyl)furan-2-carboxamide Compound 73

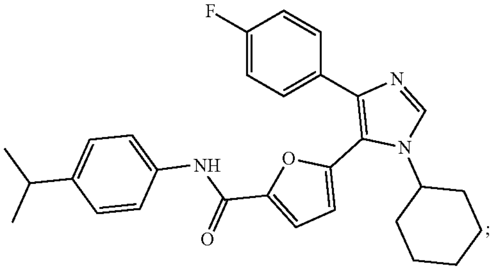

5-(1-cyclohexyl-4-(4-fluorophenyl)-1H-imidazol-5-yl)-N-(4-isopropylphenyl)furan-2-carboxamide Compound 74

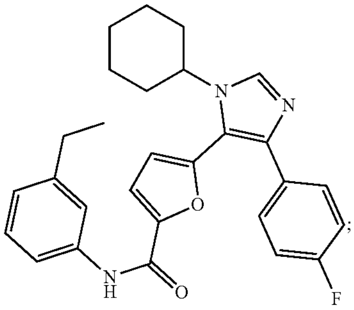

5-(1-cyclohexyl-4-(4-fluorophenyl)-1H-imidazol-5-yl)-N-(3-ethylphenyl)furan-2-carboxamide -continued Compound 75

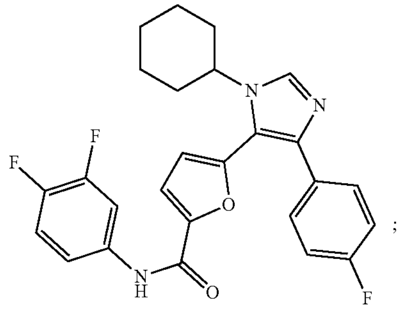

5-(1-cyclohexyl-4-(4-fluorophenyl)-1H-imidazol-5-yl)-N-(3,4-difluorophenyl)furan-2-carboxamide Compound 76

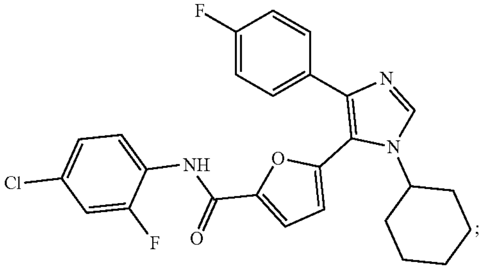

N-(4-chloro-2-fluorophenyl)-5-(1-cyclohexyl-4-(4-fluorophenyl)-1H-imidazol-5-yl)furan-2-carboxamide Compound 77

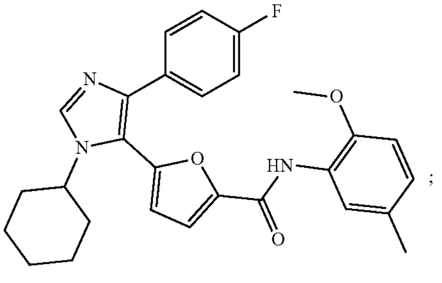

5-(1-cyclohexyl-4-(4-fluorophenyl)-1H-imidazol-5-yl)-N-(2-methoxy-5-methylphenyl)furan-2-carboxamide Compound 78

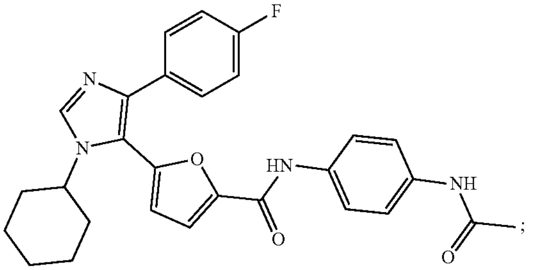

N-(4-acetamidophenyl)-5-(1-cyclohexyl-4-(4-fluorophenyl)-1H-imidazol-5-yl)furan-2-carboxamide -continued Compound 79

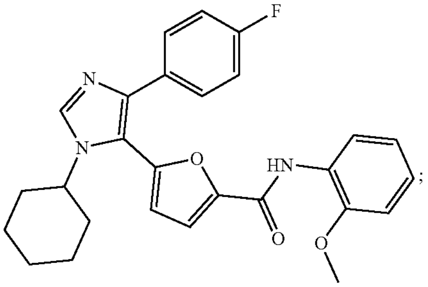

5-(1-cyclohexyl-4-(4-fluorophenyl)-1H-imidazol-5-yl)-N-(2-methoxyphenyl)furan-2-carboxamide In some embodiments, the compound used in the method is one of the following: 5-(1-cyclopentyl-4-(4-fluorophenyl)-1H-imidazol-5-yl)-N-(2,5-dimethoxyphenyl)furan-2-carboxamide; 5-(1-cyclopentyl-4-(4-fluorophenyl)-1H-imidazol-5-yl)-N-(2,5-difluorophenyl)furan-2-carboxamide; N-(2-bromophenyl)-5-(1-cyclopentyl-4-(4-fluorophenyl)-1H-imidazol-5-yl)furan-2-carboxamide; N-(2-chlorophenyl)-5-(1-cyclopentyl-4-(4-fluorophenyl)-1H-imidazol-5-yl)furan-2-carboxamide; 5-(1-cyclopentyl-4-(4-fluorophenyl)-1H-imidazol-5-yl)-N-(2,4-dimethoxyphenyl)furan-2-carboxamide; 5-(1-cyclopentyl-4-(4-fluorophenyl)-1H-imidazol-5-yl)-N-(2-fluorophenyl)furan-2-carboxamide; methyl 2-(5-(1-cyclopentyl-4-(4-fluorophenyl)-1H-imidazol-5-yl)furan-2-carboxamido)benzoate; 5-(1-cyclopentyl-4-(4-fluorophenyl)-1H-imidazol-5-yl)-N-(p-tolyl)furan-2-carboxamide; or 5-(1-cyclopentyl-4-(4-fluorophenyl)-1H-imidazol-5-yl)-N-(2-methoxyphenyl)furan-2-carboxamide.

In some embodiments, the R group substitution patterns and substituents shown in the structures of the Compounds 17-87 group can be applied to any formula provided herein.

In some embodiments, the compound is included in a pharmaceutical composition comprising: the compound; and a pharmaceutically acceptable carrier having the compound.

The kinase inhibitors can be formulated for experiments or therapies. The formulations are prepared for storage and use by combining a purified kinase inhibitor of the present invention with a pharmaceutically acceptable vehicle (e.g., carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g., octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer, intratracheal, intranasal, epidermal and transdermal); oral; or parenteral including intravenous, intraarterial, subcutaneous, intraperitoneal or intramuscular injection or infusion; intratumoral, or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc. of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

In some embodiments, pharmaceutical formulations can include kinase inhibitors of the present invention complexed with liposomes (Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The kinase inhibitor can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semi-permeable matrices of solid hydrophobic polymers containing the kinase inhibitor, which matrices are in the form of shaped articles (e.g. films or microcapsules). Examples of sustained-release matrices include polyesters, hydrogels such as poly(2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In some embodiments, the treatment involves the combined administration of a TNIK inhibitor agent of the present invention and a chemotherapeutic agent or cocktail of multiple different chemotherapeutic agents. Combination therapy often uses agents that work by different mechanisms of action. Combination therapy using agents with different mechanisms of action often results in additive or synergetic effects. Combination therapy may allow for lower doses of each agent than is used in monotherapy thereby reducing toxic side effects. Combination therapy may decrease the likelihood that resistant cancer cells will develop. In some embodiments, the combination therapy comprises a kinase inhibitor that binds to kinase (e.g., TNIK kinase inhibitor and/or MAP4K4 kinase inhibitor) and a chemotherapeutic agent.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (e.g., Tween °), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions described herein can be administered for example, by parenteral, intravenous, subcutaneous, intramuscular, intracranial, intraorbital, ophthalmic, intraventricular, intracapsular, intraspinal, intracisternal, intraperitoneal, intranasal, aerosol or oral administration. Common carriers or excipients can be used for preparing pharmaceutical compositions designed for such routes of administration.

For the treatment of the disease, the appropriate dosage of a kinase inhibitor of the present invention depends on the type of disease to be treated, the severity and course of the disease, the responsiveness of the disease, whether the kinase inhibitor is administered for therapeutic or preventative purposes, previous therapy, patient's clinical history, and so on, all at the discretion of the treating physician. The kinase inhibitor can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual kinase inhibitor. The administering physician can easily determine optimum dosages, dosing methodologies and repetition rates. In general, dosage is from 0.01 μg to 100 mg per kg of body weight, and can be given once or more daily, weekly, monthly or yearly. The treating physician can estimate repetition rates for dosing based on measured residence times and concentrations of the drug in bodily fluids or tissues.

The present invention provides kits comprising the kinase inhibitors described herein and that can be used to perform the methods described herein. In certain embodiments, a kit comprises at least one purified kinase inhibitor in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed kinase inhibitors of the present invention can be readily incorporated into one of the established kit formats which are well known in the art.

In some embodiments, the compounds can have an inhibitory activity against a wild type or mutant (especially a clinically relevant mutant) kinase, with an IC50 value of 1 μM or less (as determined using any scientifically acceptable kinase inhibition assay), preferably with an IC50 of 500 nM or less, preferably with an IC50 value of 250 nM or less, preferably with an IC50 value of 100 nM or less, preferably with an IC50 value of 50 nM or less, preferably with an IC50 value of 25 nM or less, preferably with an IC50 value of 10 nM or less.

In some embodiments, the compounds can have an IC50 value measured in TNIK enzymatic assay as provided in Table 1 below, and can be used for inhibiting TNIK, such as for the therapeutic benefits described herein.

TABLE 1

| Compound ID# | IC50, nM |
|---|---|
| Compound 6 | 9726 |
| Compound 33 | 27 |
| Compound 77 | 27 |
| Compound 36 | 110 |
| Compound 37 | 900 |
| Compound 5 | 2408 |
| Compound 13 | <10 |
| Compound 76 | 42 |
| Compound 2 | <10 |
| Compound 72 | 238 |
| Compound 22 | 483 |
| Compound 4 | 9322 |
| Compound 17 | 46 |
| Compound 51 | 57 |
| Compound 27 | <10 |
| Compound 70 | 936 |
| Compound 44 | 523 |
| Compound 71 | 151 |
| Compound 42 | 19 |
| Compound 68 | 19 |
| Compound 18 | <10 |
| Compound 61 | 164 |
| Compound 45 | 165 |
| Compound 10 | 10 |
| Compound 64 | 62 |
| Compound 35 | 151 |
| Compound 58 | 275 |
| Compound 16 | 38 |

TABLE 1-continued

| Compound ID# | IC50, nM |
|---|---|
| Compound 73 | 48 |
| Compound 49 | 152 |
| Compound 74 | 326 |
| Compound 34 | 319 |
| Compound 66 | 531 |
| Compound 19 | 231 |
| Compound 7 | 1506 |
| Compound 9 | 11 |
| Compound 79 | 16 |
| Compound 28 | 37 |
| Compound 55 | 24 |
| Compound 31 | 135 |
| Compound 52 | 60 |
| Compound 39 | 480 |
| Compound 67 | 77 |
| Compound 3 | <10 |
| Compound 30 | 95 |
| Compound 53 | 138 |
| Compound 14 | <10 |
| Compound 59 | 562 |
| Compound 50 | <10 |
| Compound 57 | 38 |
| Compound 38 | 46 |
| Compound 60 | 874 |
| Compound 11 | 42 |
| Compound 56 | 99 |
| Compound 23 | 55 |
| Compound 78 | 15 |
| Compound 32 | 12 |
| Compound 54 | 60 |
| Compound 40 | 102 |
| Compound 12 | 101 |
| Compound 20 | 136 |
| Compound 75 | 191 |
| Compound 21 | 214 |
| Compound 15 | 101 |
| Compound 69 | 90 |
| Compound 62 | 25 |
| Compound 1 | 30 |
| Compound 43 | 172 |
| Compound 65 | 152 |
| Compound 46 | 24 |
| Compound 63 | 108 |
| Compound 41 | 180 |
| Compound 8 | 4449 |
| Compound 24 | <10 |
| Compound 29 | 62 |
| Compound 48 | 40 |
| Compound 25 | 59 |
| Compound 47 | <10 |
| Compound 26 | 55 |
| Compound 80 | 26 |
| Compound 81 | 37 |
| Compound 82 | 158 |
| Compound 84 | 11 |
| Compound 85 | 251 |
| Compound 86 | 25 |
| Compound 87 | 76 |
| Compound 88 | 8452 |
| Compound 89 | 95 |
| Compound 93 | 36 |
| Compound 98 | 1733 |
| Compound 101 | 4 |
| Compound 103 | 2 |
| Compound 104 | 4 |

Compounds of this invention are also useful as standards and reagents for characterizing various kinases, especially but not limited to TNIK kinase and/or MAP4K4 kinase, as well as for studying the role of such kinases in biological and pathological phenomena; for studying intracellular signal transduction pathways mediated by such kinases, for the comparative evaluation of new kinase inhibitors; and for studying various cancers in cell lines and animal models.

EXAMPLES

TNIK Inhibition

The compounds were studied for function as TNIK inhibitors to generate the data of Table 1. The compound was incubated with 8 mM MOPS at pH 7.0, 0.2 mM EDTA, 250 μM TNIK control peptide, 10 mM Magnesium acetate, and [γ-$^{33}$P-ATP] (specific activity and concentration as required). The reaction is initiated by the addition of the Mg/ATP mix. After incubation for 40 minutes at room temperature, the reaction is stopped by the addition of phosphoric acid to a concentration of 0.5%. 10 μl of the reaction is then spotted onto a P30 filtermat and washed four time for 4 minutes in 0.425% phosphoric acid and once in methanol prior to drying and scintillation counting. Additional information can be found in Eurofins Kinase Profiler Service Assay Protocols v85.2, which is incorporated herein by specific reference in its entirety.

Fibrosis Assay

Cell Culture

HDF/TERT166 working lot cells can be thawed from liquid nitrogen and expanded using standard conditions (Medium: DMEM/Ham's F12 basal medium supplemented with 1× GlutaMax-I and 10% FBS without antibiotics; 37° C. 5% $CO_2$). For performing the treatment, cells can be seeded at a cell density of 7500 cells/cm$^2$ in 12-well plates the day before the first treatment. Cells can be seeded in starvation medium (DMEM/Ham's F12 basal medium supplemented with 1× GlutaMax-I and 0.5% FBS without antibiotics). Approximately 24 hours after seeding the substances can be dissolved in DMSO (stocks: 10 mM) and diluted in starvation medium to a final concentration of 10 μM. Half of this working dilution can be supplemented with 100 pg/mL TGF-beta. For each substance, two wells can be treated with a 10 μM concentration of the substance and a 10 μM concentration supplemented with 100 pg/mL TGF-beta. In parallel, cells can be treated with 100 pg/mL TGF-beta alone. Cells in starvation medium can serve as a control. For all cells treatment can be done by performing a medium exchange. Twenty-four hours after the first treatment (48 hrs after seeding) treatment can be repeated with fresh dilutions. Twenty-four hours after the second treatment (72 hrs after seeding) medium can be removed, cells can be washed once with PBS and cells can be directly lysed using 1 mL Tri-reagents (Sigma Aldrich) per well. Lysates can be collected in 1.5 mL tubes and stored at −80° C. until RNA isolation.

qPCR Analysis

RNA Isolation

RNA extraction can be performed with 200 μL Chloroform, and phase separation can be achieved by centrifugation for 15 min at 12,000 g at 4° C. 500 μL of the upper aqueous phase can be extracted, which can be further precipitated and purified on a QIAcube liquid-handling robot using the miRNeasy Mini Kit (Qiagen). To the 500 μL, 150 μL nuclease free water and 7 μL glycogen can be added and precipitated with 750 μL 100% ethanol. Columns can be washed with RWT and RPE buffer and circulating RNA can be eluted in a single round in 300_, nuclease free water and stored at −80° C. RNA concentration can be determined spectrophotometrically with a Nanodrop instrument.

mRNA gPCR Quantification

From isolated total RNA, cDNA can be synthesized using the GrandScript cDNA Synthesis Kit. Reverse transcription reactions can be performed in 20 μL reactions with 200 ng of total RNA (if possible, for low concentrated samples 10 μL RNA can be used). For each sample, qPCR reactions can be performed in 10 μL reactions in duplicates with 2 μL 1:2 diluted cDNA and 8 μL qPCR Mix with consists of 5 μL SYBR Grandmaster Mix, 0.8 μL forward and reverse primer (10 μM) and 2.2 μL nuclease free water. qPCR can be performed on a Roche LightCycler 480 II instrument. Following thermocycling conditions can be used: 30 sec at 95° C., 45 cycles of 5 sec at 95° C., 15 sec at 63° C., 10 sec at 72° C., followed by melting curve analysis. Cq values can be computed using the second derivative maximum method provided with the LC480 II software.

TNIK Link to Fibrosis and Cancer Metastasis

A collagen production assay was performed for a known TNIK inhibitor (5-(4 acetamidobenzamido)-2-(phenylamino)-1,3-thiazole-4-carboxamide). The data shows that this TNIK inhibitor decreased collagen type 1 alpha 1 (COL1A1) mRNA expression. Also, this TNIK inhibitor inhibited the effect of TGF-beta treatment on the COL1A1 mRNA expression. COL1A1 expression has been linked to fibrosis, where upregulation of COL1A1 can increase fibrosis in a subject. Accordingly, reducing COL1A1 mRNA expression, especially when initially over expressed, can be used to treat or inhibit fibrosis in a subject. It is known that elevated TGF-β expression in affected organs, and subsequent deregulation of TGF-β functions, correlates with the abnormal connective tissue deposition observed during the onset of fibrotic diseases. By inhibiting the effect of TGF-beta treatment on COL1A1 mRNA expression, fibrosis can be treated and reduced. Since it is known that TGF-β-activated EMT can be inhibited through the attenuation of Smad and non-Smad signaling pathways, including the Wnt, NF-κ3, FAK-Src-paxillin-related focal adhesion, and MAP kinases (ERK and JNK) signaling pathways, there is evidence that the TNIK inhibitors can be used for inhibiting TGF-β-activated EMT. As such, TNIK is a target for inhibition for therapies for treating and/or preventing EMT-based disorders, such as cancer metastasis and fibrosis. As such, the evidence indicates that the TNIK inhibitors described herein can be used in methods of treating EMT-based disorders, such as cancer metastasis and fibrosis.

TNIK Link to Lung Cancer

Additionally, TGF-beta is known to mediate epithelial to mesenchymal transition in cancer cell, such as lung cancer. At is known that inhibiting TNIK can inhibit the TGF-beta activity, and thereby inhibit the development or progression of cancers, such as lung cancer. Thus, inhibiting TNIK with the TNIK inhibitors described herein can be used in methods of treating cancer, such as lung cancer.

Additionally, the TNIK inhibitors can be administered to a person susceptible to or suspected to be susceptible to the disease or conditions described herein, such as before, during or after onset of the disease or condition. Specifically, the TNIK inhibitors can be used to inhibit or prevent or delay onset or devilment of the disease or conditions, such as cancer and fibrosis.

Thus, the TNIK inhibitors described herein can be used in method for inhibiting TNIK in order to inhibit diseases or conditions linked to TNIK activity or increased activity of TNIK or downstream upregulation or increased activity.

Compounds

In some embodiments, the present invention includes novel compounds that are kinase inhibitors (e.g., TNIK kinase inhibitor and/or MAP4K4 kinase inhibitor). For example, the compounds recited in this section can be novel.

In some embodiments, a kinase inhibitor compound (e.g., TNIK kinase inhibitor and/or MAP4K4 kinase inhibitor) can include: a structure of Formula A, or derivative thereof, prodrug thereof, salt thereof, stereoisomer thereof, tautomer thereof, polymorph thereof, or solvate thereof, or having any chirality at any chiral center.

Formula A

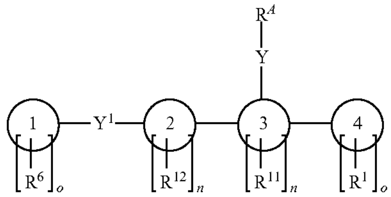

In some aspects: ring 1 is an aromatic ring with or without hetero atoms; ring 2 is a hetero aromatic ring; ring 3 includes at least one hetero aromatic ring and optionally at least one cycloaliphatic ring fused with the at least one hetero aromatic ring; ring 4 is an aromatic ring with or without hetero atoms; Y is a bond or a linker; $Y^1$ is a linker; each n is independently 0, 1, or 2; each o is independently 0, 1, 2, 3, 4, or 5; each $R^1$, $R^6$, $R^{11}$, and $R^{12}$ is independently a chemical moiety (e.g., hydrogen or other substituent). In some aspects, the compound includes at least one of the following provisions: when Y is a bond, $R^A$ is an aromatic $C_3$ cycloaliphatic ring, 5-membered hetero cycloaliphatic ring, 6-membered hetero cycloaliphatic ring, straight aliphatic chain, or branched aliphatic chain, any of which can be substituted or unsubstituted; or when Y is a chemical moiety, $R^A$ is a $C_3$ cycloaliphatic ring, 5-membered cycloaliphatic ring, 5-membered hetero cycloaliphatic ring, 6-membered cycloaliphatic ring, 6-membered hetero cycloaliphatic ring, straight aliphatic chain, or branched aliphatic chain, which can be substituted or unsubstituted and with or without hetero atoms; or the compound includes at least one of the following: when ring 1 is a phenyl group, at least one of: ring 2 is not a furanyl group; ring 3 is not an imidazolyl group; or ring 4 is not phenyl group; when ring 2 is a furanyl group, at least one of: ring 1 is not a phenyl group; ring 3 is not an imidazolyl group, or ring 4 is not a phenyl group; when ring 3 is an imidazolyl group, at least one of: ring 1 is not a phenyl group; ring 2 is not a furanyl group; or ring 4 is not a phenyl group; or when ring 4 is a phenyl group, at least one of: ring 1 is not a phenyl group; ring 2 is not a furanyl group; or ring 3 is not an imidazolyl group. In some aspects, one of ring 1 or ring 4 has o as a positive integer. In some aspects, the o is only 0 when on a hetero aromatic ring (e.g., when ring 1 or ring 4 is a hetero aromatic ring).

In some aspects, $Y^1$ includes an amide having the nitrogen bonded to ring 1 and the carbon bonded to ring 2.

In some embodiments, the compound comprises at least one of: $Y^1$ includes an amide having the nitrogen bonded to ring 1 and the carbon bonded to ring 2; when Y is a bond, $R^A$ is a $C_3$ cycloaliphatic ring, 5-membered hetero cycloaliphatic ring, 6-membered hetero cycloaliphatic ring, straight aliphatic chain, or branched aliphatic chain, any of which can be substituted or unsubstituted; when Y is a chemical moiety, $R^A$ is a $C_3$ cycloaliphatic ring, 5-membered cycloaliphatic ring, 5-membered hetero cycloaliphatic ring, 6-membered cycloaliphatic ring, 6-membered hetero cycloaliphatic ring, straight aliphatic chain, or branched aliphatic chain, which can be substituted or unsubstituted and with or without hetero atoms; or the compound includes at least one of the following: when ring 1 is a phenyl group, at least one of: ring 2 is not a furanyl group; ring 3 is not an imidazolyl group; or ring 4 is not phenyl group; when ring 2 is a furanyl group, at least one of: ring 1 is not a phenyl group; ring 3 is not an imidazolyl group, or ring 4 is not a phenyl group; when ring 3 is an imidazolyl group, at least one of: ring 1 is not a phenyl group; ring 2 is not a furanyl group; or ring 4 is not a phenyl group; or when ring 4 is a phenyl group, at least one of: ring 1 is not a phenyl group; ring 2 is not a furanyl group; or ring 3 is not an imidazolyl group.

In some embodiments, the compound includes: ring 1 is a phenyl group, pyridyl group, or pyrimidinyl group; ring 2 is a 5-membered or 6 membered hetero aromatic ring; ring 3 includes a 5-membered hetero aromatic ring or a 5-membered hetero aromatic ring fused with a 6-membered hetero aromatic ring that is fused with a 5-membered cycloaliphatic ring, where the bond to Y is through the 5-membered hetero aromatic ring; ring 4 is a phenyl group, pyridyl group, pyrimidyl group, or triazinyl group; Y is a bond or an aliphatic linker; and wherein when Y is a bond $R^A$ is not a 5-membered cycloaliphatic ring.

In some embodiments, the compound includes: ring 1 is a phenyl group, pyridyl group, or pyrimidinyl group, when ring 1 is pyridyl or pyrimidinyl the nitrogens are located at the para, meta, or ortho position in the ring; ring 2 is a furanyl group, thiophenyl group, pyrrolyl group, oxazolyl group, thiazolyl group, imidazolyl group, triazolyl group, or pyridyl group; ring 3 is a imidazolyl group, triazolyl group, or cyclopenta-pyrrolo-pyridinyl fused ring group; or cyclopenta-furo-pyridinyl group; ring 4 is a phenyl group, pyridyl group, pyrimidyl group, or triazinyl group, when ring 4 is pyridyl the nitrogen is located at the para, meta, or ortho positions in the ring; when ring 4 is pyrimidyl group, the nitrogens are at the meta or ortho positions in the ring; and Y is a bond or $C_1$-$C_6$ aliphatic.

In some embodiments, when Y is a $C_1$-$C_6$ aliphatic linker, $R^A$ is a $C_3$-$C_6$ cycloaliphatic ring, $C_5$-$C_6$ hetero cycloaliphatic ring, aromatic ring, $C_1$-$C_{11}$ straight aliphatic, or $C_1$-$C_{11}$ branched aliphatic, which can be substituted or unsubstituted, any with or without hetero atoms, or when Y is a bond, $R^A$ is a not a $C_6$-$C_6$ cycloaliphatic ring.

In some embodiments, each $R^1$, $R^6$, $R^{11}$, and $R^{12}$ is independently hydrogen, F, Br, Cl, I, methyl, ethyl, propyl, butyl, pentyl, hexyl, heptyl, octyl, isopropyl, tert-butyl, oxygen, oxide, hydroxy, methoxy, ethoxy, propoxy, butoxy, pentoxy, hexoxy, heptoxy, octoxy, trifluromethyloxy, methylthio, ethylthio, propylthio, butylthio, pentylthio, hexylthio, heptylthio, octylthio, methylalcohol, ethylalcohol, propylalcohol, butylalcohol, pentylalcohol, hexylalcohol, heptylalcohol, octylalcohol, acetyl, carboxylic acid, alkyl carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethylsulfanyl, propylsulfanyl, butylsulfanyl, pentylsulfanyl, hexylsulfanyl, heptylsulfanyl, octylsulfanyl, sulfamoyl, methylpiperazinium, piperazinyl, hydroxyethylpiperazinyl, bis(2-hydroxyethyl)amino, morpholino, or combinations thereof.

In some embodiments, $R^{11}$ and $R^{12}$ are hydrogen or nothing, and each $R^1$ or $R^6$ is independently hydrogen, F, Br, Cl, I, methyl, ethyl, propyl, butyl, pentyl, hexyl, heptyl, octyl, isopropyl, tert-butyl, trifluoromethyl, oxygen, oxide, hydroxy, methoxy, ethoxy, propoxy, butoxy, pentoxy, hexoxy, heptoxy, octoxy, trifluromethyloxy, methylthio, ethylthio, propylthio, butylthio, pentylthio, hexylthio, heptylthio, octylthio, methylalcohol, ethylalcohol, propylalcohol, butylalcohol, pentylalcohol, hexylalcohol, heptylalcohol, octylalcohol, acetyl, carboxylic acid, alkyl carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethylsulfanyl, propylsulfanyl, butylsulfanyl, pentylsulfanyl, hexylsulfanyl, heptylsulfanyl, octylsulfanyl, sulfamoyl, methylpiperazinium, piperazinyl, hydroxyethylpiperazinyl, bis(2-hydroxyethyl)amino, morpholino, or combinations thereof.

In some embodiments, each $R^1$ is independently hydrogen, F, Br, Cl, I, methyl, ethyl, propyl, butyl, pentyl, hexyl, heptyl, octyl, isopropyl, tert-butyl, trifluoromethyl, hydroxy, methoxy, ethoxy, propoxy, butoxy, pentoxy, hexoxy, heptoxy, octoxy, trifluromethyloxy, or combinations thereof.

In some embodiments, $R^{11}$ and $R^{12}$ are hydrogen or nothing, and each $R^6$ is independently hydrogen, F, Br, Cl, I, methyl, ethyl, propyl, butyl, pentyl, hexyl, heptyl, octyl, isopropyl, tert-butyl, trifluoromethyl, oxygen, oxide, hydroxy, methoxy, ethoxy, propoxy, butoxy, pentoxy, hexoxy, heptoxy, octoxy, trifluromethyloxy, methylthio, ethylthio, propylthio, butylthio, pentylthio, hexylthio, heptylthio, octylthio, methylalcohol, ethylalcohol, propylalcohol, butylalcohol, pentylalcohol, hexylalcohol, heptylalcohol, octylalcohol, acetyl, carboxylic acid, alkyl carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethylsulfanyl, propylsulfanyl, butylsulfanyl, pentylsulfanyl, hexylsulfanyl, heptylsulfanyl, octylsulfanyl, sulfamoyl, methylpiperazinium, piperazinyl, hydroxyethylpiperazinyl, bis(2-hydroxyethyl)amino, morpholino, or combinations thereof.

In some embodiments, $Y^1$ is an amide, hydrazide, carbohydrazide, hydroxy-substituted amide, alkyl-substituted amide, carboximidamide, or sulfonimidamide.

In some embodiments, $R^A$ is from hydrogen, cyclopentyl, tetrahydrofuranyl, pyrrolidinyl, piperidinyl, pyridinyl, pyrimidinyl, bicycloheptanyl, bicyclooctanyl, bicyclo[3.1.1]heptan-3yl, bicyclo[2.2.2octan-2yl, bicyclo[3.2.1]octan-3-yl, fluorotetrahydrofuranyl, difluorotetrahydrofuranyl, oxetanyl, hydroxycyclopentyl, methylcyclopentyl, cyclopropyl, cyclobutyl, cyclopentyl, cyclohexyl, methyl, ethyl, propyl, butyl, pentyl, hexyl, heptyl, octyl, isopropyl, tert-butyl, hydroxypropanyl, trifluoromethyl, methoxy, ethoxy, propoxy, butoxy, pentoxy, hexoxy, heptoxy, octoxy, phenyl, or combinations thereof.

In some embodiments, ring 1 is a phenyl group or pyridyl group, when ring 1 is pyridyl the nitrogen is located at the para, meta, or ortho position in the ring; ring 2 is a furanyl group, thiophenyl group, pyrrolyl group, oxazolyl group, thiazolyl group; imidazolyl group, triazolyl group, or pyridyl group; ring 3 is a imidazolyl group, triazolyl group, or cyclopenta-pyrrolo-pyridinyl fused ring group; or cyclopenta-furo-pyridinyl group; ring 4 is a phenyl group, pyridyl group, pyrimidyl group, or triazinyl group, when ring 4 is pyridyl the nitrogen is located at the para, meta, or ortho positions in the ring; when ring 4 is pyrimidyl group, the nitrogens are at the meta or ortho positions in the ring; Y is a bond or $C_1$-$C_6$ aliphatic; $Y^1$ is an amide linker; and when Y is a $C_1$-$C_6$ aliphatic linker, $R^A$ is a $C_3$-$C_6$ cycloaliphatic ring, $C_5$-$C_6$ hetero cycloaliphatic ring; $C_1$-$C_{12}$ straight aliphatic, or $C_1$-$C_{12}$ branched aliphatic, which can be substituted or unsubstituted, any with or without hetero atoms, or when Y is a bond, $R^A$ is a not a $C_6$-$C_6$ cycloaliphatic ring.

In some embodiments, each $R^1$ and $R^6$ is independently hydrogen, F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., CH3C═O), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl. In some aspects, $R^{11}$ and $R^{12}$ are hydrogen or nothing.

In some embodiments, the kinase inhibitor (e.g., TNIK kinase inhibitor and/or MAP4K4 kinase inhibitor) is a compound having a structure of Formula A1 or Formula A2, or derivative thereof, prodrug thereof, salt thereof, stereoisomer thereof, tautomer thereof, polymorph thereof, or solvate thereof, or having any chirality at any chiral center. In some aspects of Formulae A1 or A2: ring D is a ring structure having one or more rings fused together; each $R^1$, $R^2$, $R^3$, $R^4$, $R^5$, $R^6$, $R^7$, $R^8$, $R^9$, $R^{10}$, $R^{11}$, and $R^{12}$ is independently a chemical moiety; the $X^1$, $X^2$, $X^3$, $X^6$, $X^7$, $X^8$, $X^9$, $X^{10}$, $X^{11}$, $X^{12}$, $X^{13}$, $X^{14}$, and $X^{20}$ are each independently a carbon or a hetero atom with or without a substituent; Y is a bond or a linker; $Y^1$ is a linker; m is 1, 2, or 3; and n is 0, 1, or 2; when Y is a bond, $R^A$ is hydrogen, aromatic cycloaliphatic, straight aliphatic, or branched aliphatic, any substituted or unsubstituted, any with or without hetero atoms; when Y is a linker, $R^A$ is an aromatic, cycloaliphatic, straight aliphatic, or branched aliphatic, any substituted or unsubstituted, any with or without hetero atoms; wherein when an X group is N in an aromatic ring, the R group bonded thereto is nothing; when the dashed line forms a double bond $X^{12}$ is N (e.g., double bond to oxygen for ketone).

In some aspects: $R^A$ is a C3 cycloaliphatic, C4-C12 hetero cycloaliphatic, straight aliphatic, or branched aliphatic, any substituted or unsubstituted, wherein the $C_3$ ring structure, straight aliphatic, or branched aliphatic, are with or without hetero atoms; ring D is a ring structure having one or more rings fused together; each $R^1$, $R^2$, $R^3$, $R^5$, $R^6$, $R^7$, $R^8$, $R^9$, $R^{10}$, $R^{11}$, and $R^{12}$ is independently a substituent; the $X^1$, $X^2$, $X^3$, $X^6$, $X^7$, $X^8$, $X^9$, $X^{10}$, $X^{11}$, $X^{12}$, $X^{13}$ and $X^{14}$ are each independently a carbon or a hetero atom with or without a substituent; Y is a bond or a linker; $Y^1$ is a linker; m is 1, 2, or 3; and n is 0, 1, or 2. In some aspects, when an X group is N in an aromatic ring, the R group bonded thereto is nothing. These variables can be the same as defined herein. In some aspects, the R group substitution patterns of some of the example compounds can be applied to these formulae. In some aspects, the X group patterns of the example compounds can be applied to these formulae.

In some embodiments, the kinase inhibitor (e.g., TNIK kinase inhibitor and/or MAP4K4 kinase inhibitor) can include a structure of one of Formulae 4A-4K or 5A-5K, or derivative thereof, prodrug thereof, salt thereof, stereoisomer thereof, tautomer thereof, polymorph thereof, or solvate thereof, or having any chirality at any chiral center. In some aspects: each $R^1$, $R^2$, $R^3$, $R^4$, $R^5$, $R^6$, $R^7$, $R^8$, $R^9$, $R^{10}$, $R^{11}$, and $R^{12}$ is independently a chemical moiety; the $X^1$, $X^2$, $X^3$, $X^6$, $X^7$, $X^8$, $X^9$, $X^{10}$, $X^{11}$, $X^{12}$, $X^{13}$, $X^{14}$ and $X^{20}$ are each independently a carbon or a hetero atom with or without a substituent; $Y^1$ is a linker; m is 1, 2, or 3; and n is 0, 1, or 2; wherein when an X group is N in an aromatic ring, the R group bonded thereto is nothing; $R^{13}$ is independently selected from hydrogen, straight aliphatic, branched aliphatic, —Y-Ring A; Ring B; or —Y—$R^A$ any of which can be substituted or unsubstituted, any with or without hetero atoms, wherein: Y is a bond or a linker; Ring A is a cycloaliphatic or hetero cycloaliphatic, or combination thereof, any substituted or unsubstituted; and Ring B is a hetero cycloaliphatic. In some instances, $R^{13}$ is an aromatic, such as phenyl, pyridinyl, pyrimidinyl, or the like.

In some embodiments, $X^4$ is C (e.g., CH, $CH_2$) or N (e.g., N, NH, $NR^1$, $NOR^1$), any with or without a substituent (e.g., $R^1$); and $X^5$ is a O or N (e.g., NH, $NR^1$, $NOR^1$). Here, $R^1$ is as defined herein, where H, OH, methyl, ethyl, trifluoromethyl are examples. The $X^4$ can be C, NH or NOH, or $NOR^1$. $X^5$ is a O or $NR^1$, or $NOR^1$. In some aspects, $X^4$ is C, CH, $CH_2$, $CR^1$, $C(R^1)_2$ or N, NH, $NR^1$, NOH, any with or without a substituent.

In some embodiments, the compound can include at least one of the following: Y is a chemical moiety linker; $Y^1$ is an amide linker linked in either orientation; $X^3$ is S or NH; at least one of $X^6$, $X^7$, $X^8$, $X^9$, $X^{10}$, $X^{11}$, $X^{12}$, or $X^{13}$ is N; or $X^{14}$ is O or NH. $X^5$ is a O or NH, $NR^1$, $NOR^1$.

In some embodiments, the linker $Y^1$ is an amide, hydrazide, carbohydrazide, hydroxy-substituted amide, alkyl-substituted amide, carboximidamide, or sulfonimidamide.

In some embodiments, $Y^1$ can be:

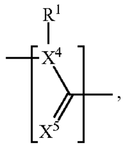, 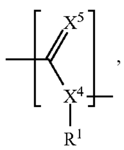, 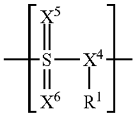, 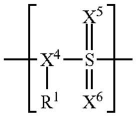

wherein $X^4$, $X^5$, and $X^6$ are hetero atoms. In some aspects, $X^4$ is N and $X^5$ is O and $R^1$ is as defined herein. In some aspects, $X^4$ is N and $X^5$ is N and $R^1$ is as defined herein, such as hydrogen. In some aspects, $X^4$ is N and $X^5$ is O and $R^1$ is hydrogen, methyl, hydroxyl, amine with or without a substituent, such as an alkyl (e.g., methyl). In some aspects, $X^4$ is N, $X^5$ is NH and $X^6$ is O. In some aspects, $X^4$ is C (e.g., CH, $CH_2$) or N (e.g., N, NH, $NR^1$, $NOR^1$), any with or without a substituent (e.g., $R^1$); and $X^5$ is a O or N (e.g., NH, $NR^1$, $NOR^1$). Here, $R^1$ is as defined herein, where H, OH, methyl, ethyl, trifluoromethyl are examples. The $X^4$ can be C, NH or NOH, or $NOR^1$. $X^5$ is a O or $NR^1$, or $NOR^1$.

In some embodiments, $Y^1$ can be:

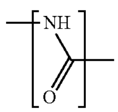 or 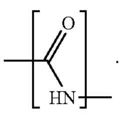.

In some embodiments, the kinase inhibitor (e.g., TNIK kinase inhibitor and/or MAP4K4 kinase inhibitor) can include a structure of Formulae 1K, 1L, 1M, 1N, 1O, 1P, or 1Q, or derivative thereof, prodrug thereof, salt thereof, stereoisomer thereof, tautomer thereof, polymorph thereof, or solvate thereof, or having any chirality at any chiral center. In some aspects, Y is a chemical moiety linker; $Y^1$ is a chemical moiety linker; $X^4$ is NH; and $X^5$ is 0. In some aspects, $X^4$ is C (e.g., CH, $CH_2$) or N (e.g., N, NH, $NR^1$, $NOR^1$), any with or without a substituent (e.g., $R^1$); and $X^5$ is a 0 or N (e.g., NH, $NR^1$, $NOR^1$). Here, $R^1$ is as defined herein, where H, OH, methyl, ethyl, trifluoromethyl are examples. The $X^4$ can be C, NH or NOH, or $NOR^1$. $X^5$ is a O or $NR^1$, or $NOR^1$.

Formula 1K

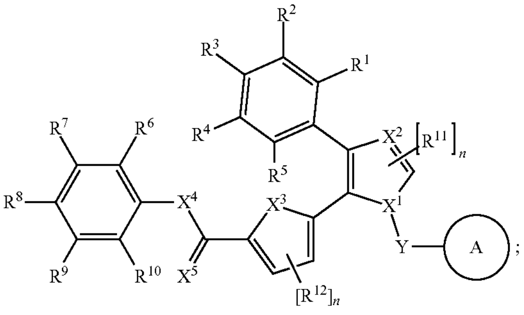

Formula 1L

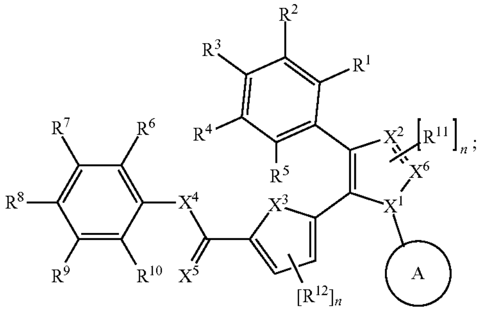

Formula 1M

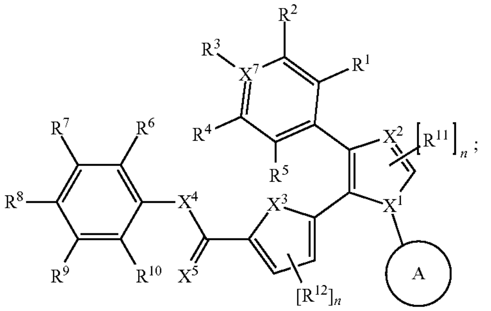

-continued

Formula 1N

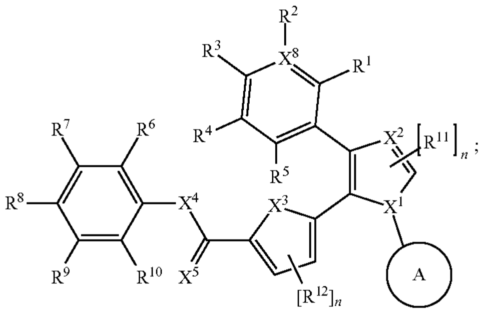

Formula 1O

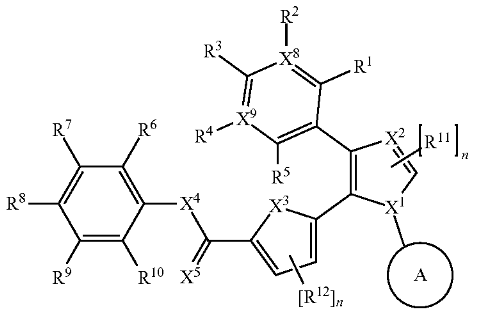

Formula 1P

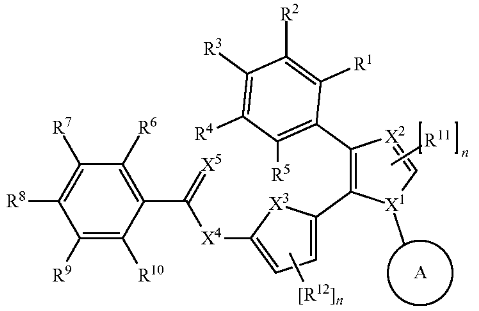

Formula 1Q

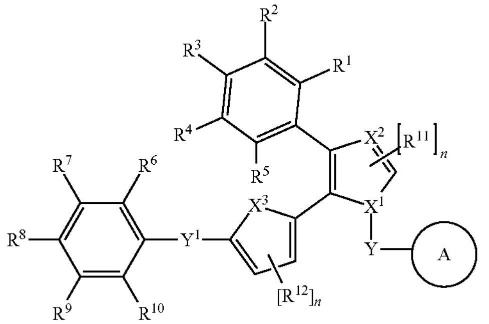

wherein; Y is a chemical moiety linker; $Y^1$ is a chemical moiety; $X^4$ is $NR^1$; and $X^5$ is 0 or N. In some aspects, $X^4$ is C (e.g., CH, $CH_2$) or N (e.g., N, NH, $NR^1$, $NOR^1$), any with or without a substituent (e.g., $R^1$); and $X^5$ is a 0 or N (e.g., NH, $NR^1$, $NOR^1$). Here, $R^1$ is as defined herein, where H, OH, methyl, ethyl, trifluoromethyl are examples. The $X^4$ can be C, NH or NOH, or $NOR^1$. $X^5$ is a O or $NR^1$, or $NOR^1$.

In some embodiments, the kinase inhibitor can include a structure of Formulae 1R, 1S, 1T, 1U, 1V, 1W, 1X, 1Y, or 1Z derivative thereof, prodrug thereof, salt thereof, stereoisomer thereof, tautomer thereof, polymorph thereof, or solvate thereof, or having any chirality at any chiral center.

Formula 1R

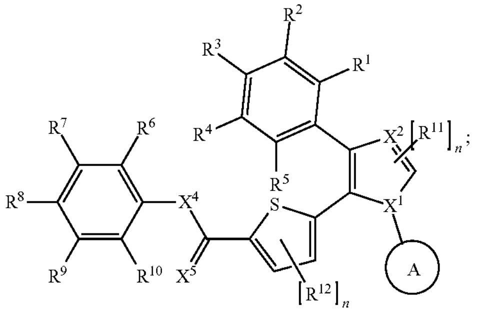

Formula 1S

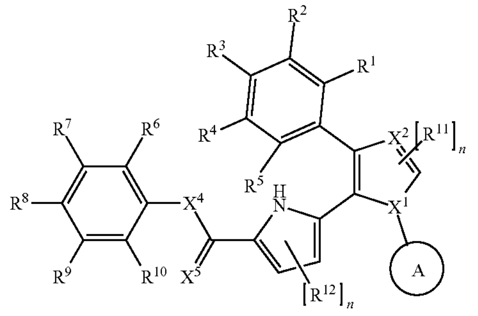

Formula 1T

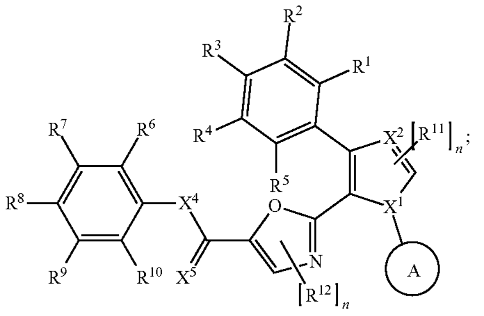

Formula 1U

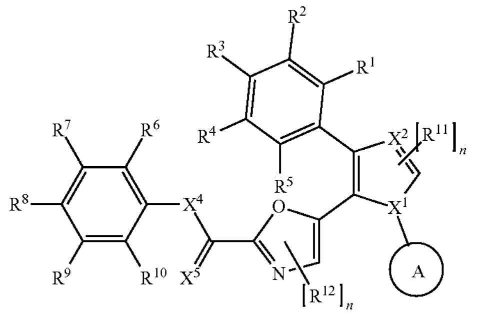

-continued

Formula 1V

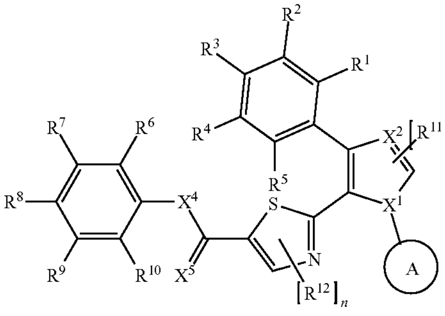

Formula 1W

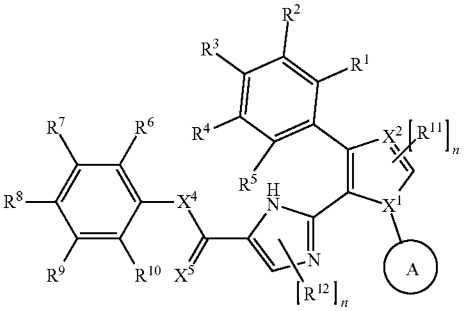

Formula 1X

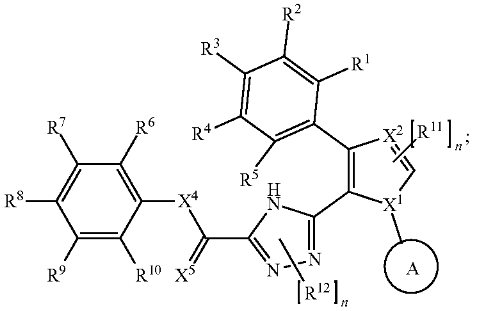

Formula 1Y

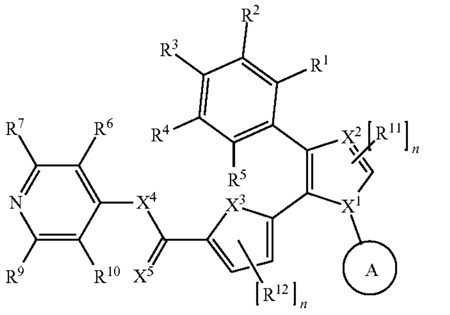

-continued

Formula 1Z

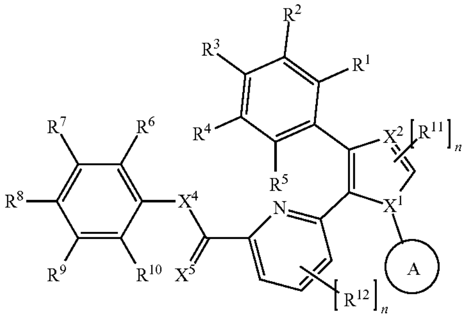

wherein, $X^4$ is $NR^1$; and $X^5$ is O or N. In some aspects, $X^4$ is C (e.g., CH, $CH_2$) or N (e.g., N, NH, $NR^1$, $NOR^1$), any with or without a substituent (e.g., $R^1$); and $X^5$ is a 0 or N (e.g., NH, $NR^1$, $NOR^1$). Here, $R^1$ is as defined herein, where H, OH, methyl, ethyl, trifluoromethyl are examples. The $X^4$ can be C, NH or NOH, or $NOR^1$. $X^5$ is a O or $NR^1$, or $NOR^1$.

In some embodiments, the kinase inhibitor can include a structure of Formulae 5K1, or 5L1, or derivative thereof, prodrug thereof, salt thereof, stereoisomer thereof, tautomer thereof, polymorph thereof, or solvate thereof, or having any chirality at any chiral center.

Formula 5K1

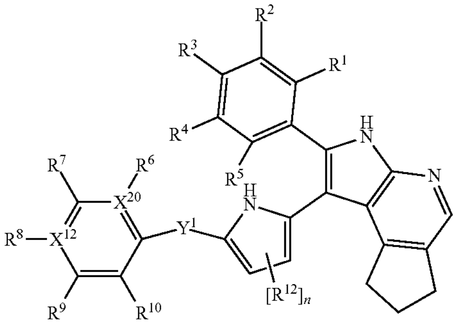

Formula 5L1

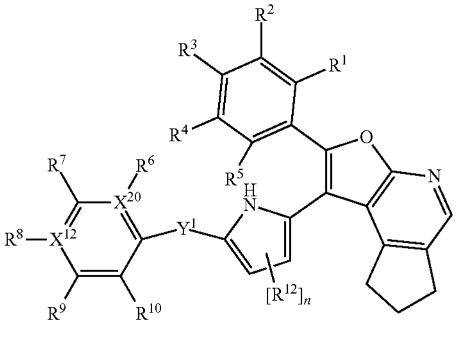

In the formulae provided herein, the compound includes at least one of the following: $R^3$ being a substituent; $R^6/R^{10}$ being a substituent; $R^7/R^9$ being a substituent; and $R^8$ being a substituent. The other R groups can be hydrogen or nothing. In some aspects, the compound includes at least one of the following: $R^3$ being F or methyl; $R^6/R^{10}$ being F, Br, Cl, methoxy, or methyl ester; $R^7/R^9$ being F or methoxy; or $R^8$ being F, methoxy, or methyl. In some aspects, the compound includes the following: $R^3$ being F or methyl; and $R^1$, $R^2$, $R^4$, and $R^5$ being H. In some aspects, the compound includes one of the following: $R^6$ and $R^9$ having the substituent, and $R^7$, $R^8$, and $R^{10}$ being H; $R^6$ having the substituent, and $R^7$, $R^8$, $R^9$, and $R^{10}$ being H; $R^8$ having the substituent, and $R^6$, $R^7$, $R^9$, and $R^{10}$ being H; or $R^6$ and $R^8$ having the substituent, and $R^7$, $R^9$, and $R^{10}$ being H. In some aspects, the compound includes the following: $R^3$ being F or methyl; $R^1$, $R^2$, $R^4$, and $R^5$ being H; $R^6$ being F, Br, Cl, methoxy, or methyl ester; $R^9$ being F or methoxy; and $R^7$, $R^8$, and $R^{16}$ being H. In some aspects, the compound includes the following: $R^3$ being F or methyl; $R^1$, $R^2$, $R^4$, and $R^5$ being H; $R^6$ being F, Br, Cl, methoxy, or methyl ester; and $R^7$, $R^8$, $R^9$, and $R^{10}$ being H. In some aspects, the compound includes the following: $R^3$ being F or methyl; $R^1$, $R^2$, $R^4$, and $R^5$ being H; $R^8$ being F methoxy, or methyl; and $R^6$, $R^7$, $R^9$, and $R^{10}$ being H. In some aspects, the compound includes the following: $R^3$ being F or methyl; $R^1$, $R^2$, $R^4$, and $R^5$ being H; $R^6$ being F, Br, Cl, methoxy, or methyl ester; $R^8$ being F methoxy, or methyl; and $R^7$, $R^9$, and $R^{16}$ being H.

In some embodiments, $R^1$, $R^2$, $R^3$, $R^4$, $R^5$, $R^6$, $R^7$, $R^8$, $R^9$, $R^{10}$, $R^{11}$, and $R^{12}$ are each independently halogen, alkyl, branched alkyl, alkoxy, alkyl ester, alkylsuflanyl (i.e., thioalkyl), acetyl, (trifluoroalkyl)oxy, trifluoroalkyl, or acetamide (i.e., acetylamino). In some aspects, $R^3$, $R^6$, $R^7$, $R^8$, $R^9$, or $R^{10}$ are each independently halogen, alkyl, branched alkyl, alkoxy, alkyl ester, alkylsulfanyl (i.e., thioalkyl), acetyl, (trifluoroalkyl)oxy, trifluoroalkyl, acetamide (i.e., acetylamino), and the rest of the R groups are hydrogen or nothing. In some aspects, n is 0 and $R^{11}$ and $R^{12}$ are nothing.

In some embodiments, each $R^1$, $R^2$, $R^3$, $R^4$, and $R^5$ is independently a hydrogen, F, Br, Cl, I, methyl, ethyl, propyl, butyl, pentyl, hexyl, heptyl, octyl, isopropyl, tert-butyl, trifluoromethyl, hydroxy, methoxy, ethoxy, propoxy, butoxy, pentoxy, hexoxy, heptoxy, octoxy, trifluromethyloxy, or combinations thereof.

In some embodiments, each $R^6$, $R^7$, $R^8$, $R^9$, or $R^{10}$ is independently hydrogen, F, Br, Cl, I, methyl, ethyl, propyl, butyl, pentyl, hexyl, heptyl, octyl, isopropyl, tert-butyl, trifluoromethyl, oxygen, oxide, hydroxy, methoxy, ethoxy, propoxy, butoxy, pentoxy, hexoxy, heptoxy, octoxy, trifluromethyloxy, methylthio, ethylthio, propylthio, butylthio, pentylthio, hexylthio, heptylthio, octylthio, methylalcohol, ethylalcohol, propylalcohol, butylalcohol, pentylalcohol, hexylalcohol, heptylalcohol, octylalcohol, acetyl, carboxylic acid, alkyl carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethylsulfanyl, propylsulfanyl, butylsulfanyl, pentylsulfanyl, hexylsulfanyl, heptylsulfanyl, octylsulfanyl, sulfamoyl, methylpiperazinium, piperazinyl, hydroxyethylpiperazinyl, bis(2-hydroxyethyl)amino, morpholino, or combinations thereof.

In some embodiments, each $R^{11}$ and $R^{12}$ is hydrogen or nothing.

In some embodiments: $X^1$, $X^2$, $X^6$, $X^7$, $X^8$, $X^9$, $X^{12}$, $X^{13}$, and $X^{20}$ are independently CH or N; $X^3$ is NH, O, or S; $X^{10}$ and $X^{11}$ are independently CH or N; and $X^{14}$ are independently NH or O.

In some embodiments, $R^{13}$ is independently a bond or $C_1$-$C_6$ alkyl coupled to at least one of: hydrogen, alkyl, cycloalkyl, hetero cycloalkyl, alkoxy, any substituted or unsubstituted, or combinations thereof.

In some embodiments, $R^{13}$ is independently a bond or $C_1$-$C_6$ alkyl coupled to at least one of: hydrogen, tetrahydrofuran, pyrrolidinyl, piperidinyl, pyridinyl, pyrimidinyl, bicycloheptanyl, bicyclooctanyl, bicyclo[3.1.1]heptan-3yl, bicyclo[2.2.2]octan-2yl, bicyclo[3.2.1]octan-3-yl, fluorotetrahydrofuranyl, difluorotetrahydrofuranyl, oxetanyl, hydroxycyclopentyl, methylcyclopentyl, cyclopropyl, cyclobutyl, cyclopentyl, cyclohexyl, methyl, ethyl, propyl, butyl, pentyl, hexyl, heptyl, octyl, isopropyl, tert-butyl, hydroxypropanyl, trifluoromethyl, methoxy, ethoxy, propoxy, butoxy, pentoxy, hexoxy, heptoxy, octoxy, phenyl, or combinations thereof.

In some embodiments, the compound is one of the following Compounds 80-106:

Compound 80

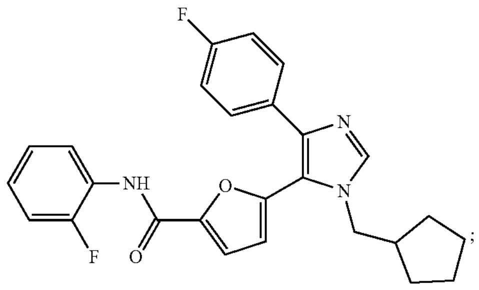

5-(1-(cyclopentylmethyl)-4-(4-fluorophenyl)-1H-imidazol-5-yl)-N-(2-fluorophenyl)furan-2-carboxamide Compound 81

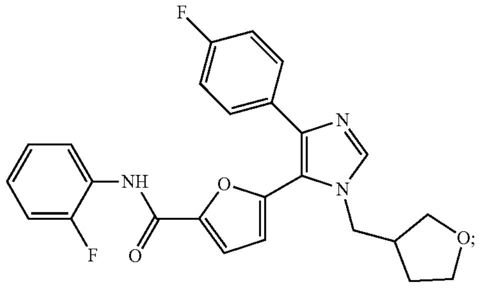

N-(2-fluorophenyl)-5-(4-(4-fluorophenyl)-1-((tetrahydrofuran-3-yl)methyl)-1H-imidazol-5-yl)furan-2-carboxamide Compound 82

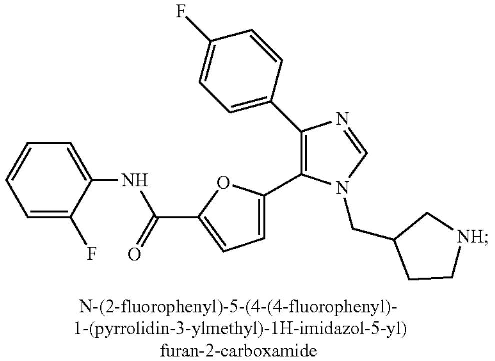

N-(2-fluorophenyl)-5-(4-(4-fluorophenyl)-1-(pyrrolidin-3-ylmethyl)-1H-imidazol-5-yl)furan-2-carboxamide Compound 83

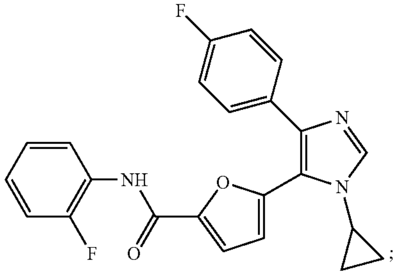

5-(1-cycloprpoyl-4-(4-fluorophenyl)-1H-imidazol-5-yl)-N-(2-fluorophenyl)furan-2-carboxamide Compound 84

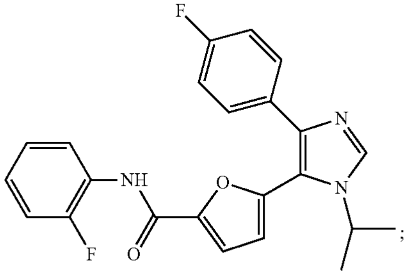

N-(2-fluorophenyl)-5-(4-(4-fluorophenyl)-1-isopropyl-1H-imidazol-5-yl)furan-2-carboxamide Compound 85

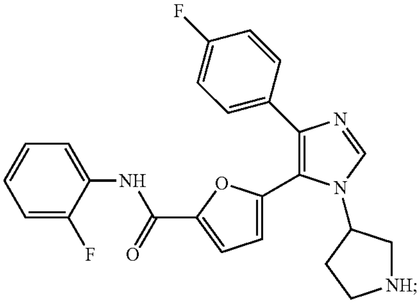

N-(2-fluorophenyl)-5-(4-(4-fluorophenyl)-1-(pyrrolidin-3-yl)-1H-imidazol-5-yl)furan-2-carboxamide Compound 86

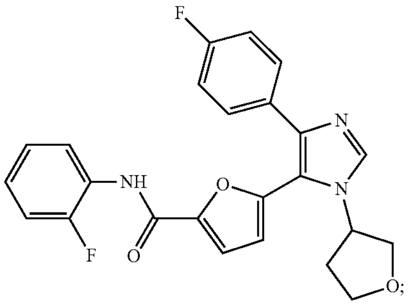

N-(2-fluorophenyl)-5-(4-(4-fluorophenyl)-1-(tetrahydrofuran-3-yl)-1H-imidazol-5-yl)furan-2-carboxamide Compound 87

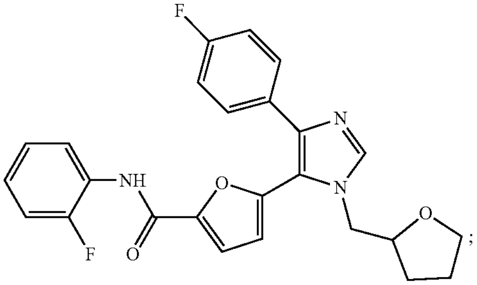

N-(2-fluorophenyl)-5-(4-(4-fluorophenyl)-1-((tetrahydrofuran-2-yl)methyl)-1H-imidazol-5-yl)furan-2-carboxamide Compound 88

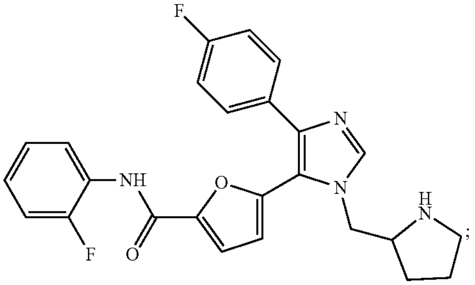

N-(2-fluorophenyl)-5-(4-(4-fluorophenyl)-1-(pyrrolidin-2-ylmethyl)-1H-imidazol-5-yl)furan-2-carboxamide Compound 89

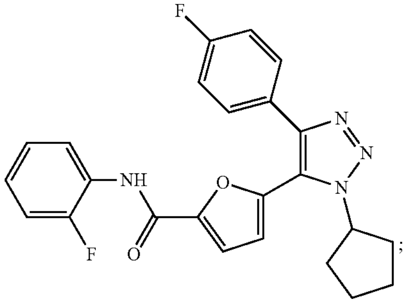

5-(1-cyclopentyl-4-(4-fluorophenyl)-1H-1,2,3-trizol-5-yl)-N-(2-fluorophenyl)furan-2-carboxamide Compound 90

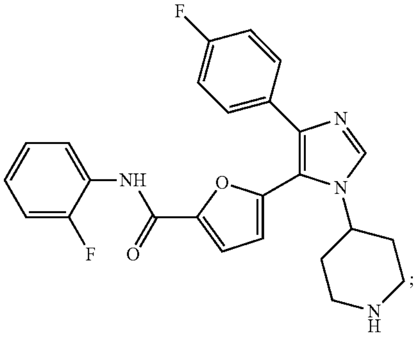

N-(2-fluorophenyl)-5-4-(4-fluorophenyl)-1-(piperidin-4-yl)-1H-imidazol-5-yl)furan-2-carboxamide -continued Compound 91

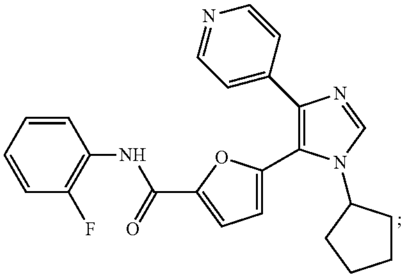

5-(1-cyclopentyl-4-(pyridin-4-yl)-1H-imidazol-5-yl)-N-(2-fluorophenyl)furan-2-carboxamide Compound 92

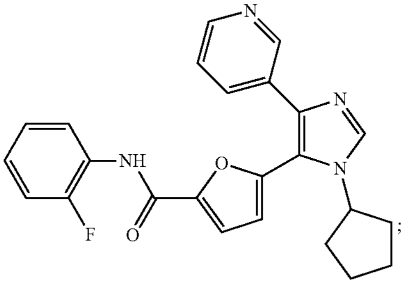

5-(1-cyclopentyl-4-(pyridin-3-yl)-1H-imidazol-5-yl)-N-(2-fluorophenyl)furan-2-carboxamide Compound 93

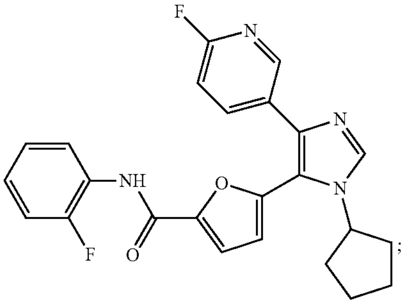

5-(1-cyclopentyl-4-(6-fluoropyridin-3-yl)-1H-imidazol-5-yl)-N-(2-fluorophenyl)furan-2-carboxamide Compound 94

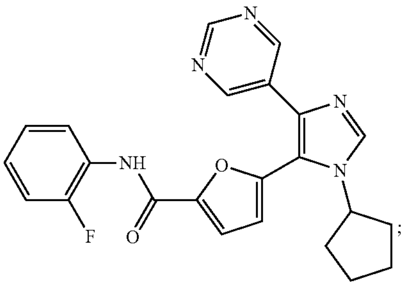

5-(1-cyclopentyl-4-(pyrimidin-5-yl)-1H-imidazol-5-yl)-N-(2-fluorophenyl)furan-2-carboxamide -continued Compound 95

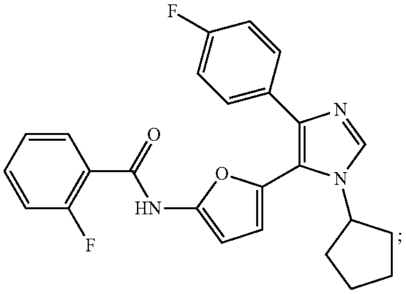

N-(5-(1-cyclopentyl-4-(4-fluorophenyl)-1H-imidazol-5-yl)furan-2-yl)-2-fluorobenzamide Compound 96

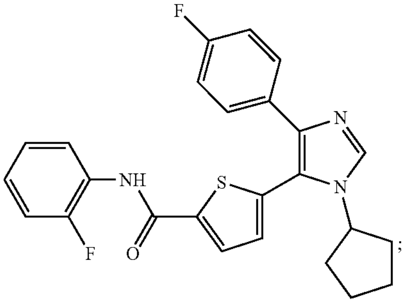

5-(1-cyclopentyl-4-(4-fluorophenyl)-1H-imidazol-5-yl)-N-(2-fluorophenyl)thiophene-2-carboxamide Compound 97

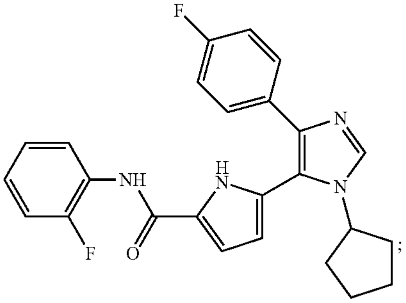

5-(1-cyclopentyl-4-(4-fluorophenyl)-1H-imidazol-5-yl)-N-(2-fluorophenyl)-1H-pyrrole-2-carboxamide Compound 98

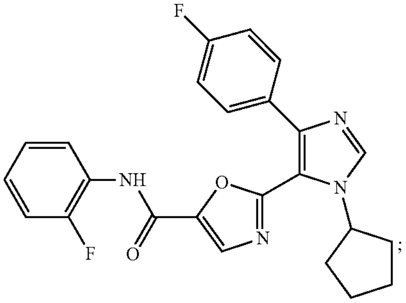

2-(1-cyclopentyl-4-(4-fluorophenyl)-1H-imidazol-5-yl)-N-(2-fluorophenyl)-oxazole-5-carboxamide -continued Compound 99

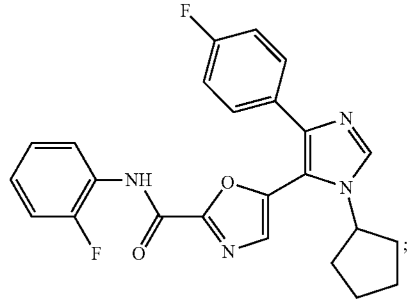

5-(1-cyclopentyl-4-(4-fluorophenyl)-1H-imidazol-5-yl)-N-(2-fluorophenyl)-oxazole-5-carboxamide Compound 100

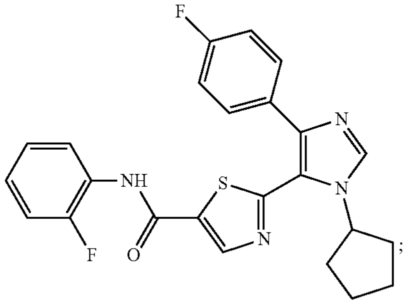

2-(1-cyclopentyl-4-(4-fluorophenyl)-1H-imidazol-5-yl)-N-(2-fluorophenyl)-thiazole-5-carboxamide Compound 101

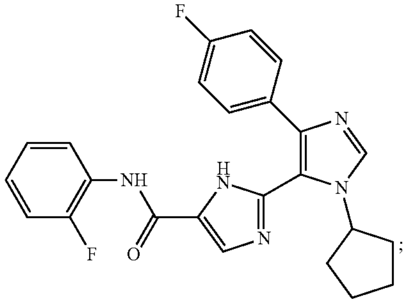

3′-cyclopentyl-N-(2-fluorophenyl)-5′-(4-fluorophenyl)-1H,3′H-[2,4′-biimidazole]-5-carboxamide Compound 102

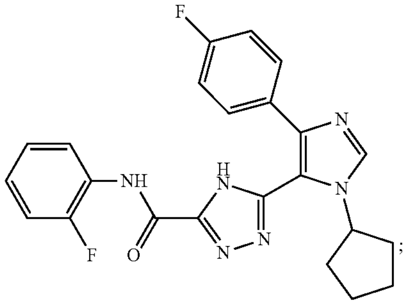

5-(1-cyclopentyl-4-(4-fluorophenyl)-1H-imidazol-5-yl)-N-(2-fluorophenyl)-4H-1,2,4-triazole-3-carboxamide -continued Compound 103

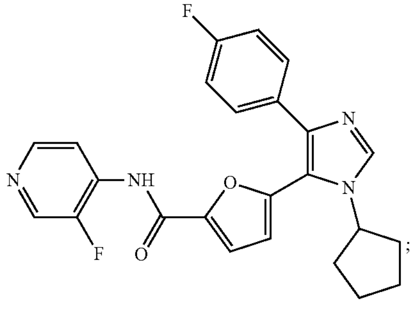

5-(1-cyclopentyl-4-(4-fluorophenyl)-1H-imidazol-5-yl)-N-(3-fluoropyridin-4-yl)furan-2-carboxamide Compound 104

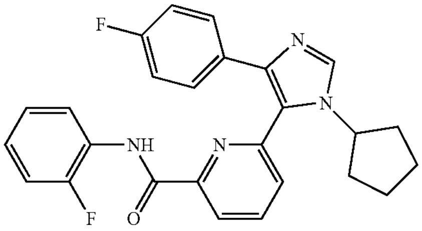

6-(1-cyclopentyl-4-(4-fluorophenyl)-1H-imidazol-5-yl)-N-(2-fluorophenyl) picolinamide Compound 105

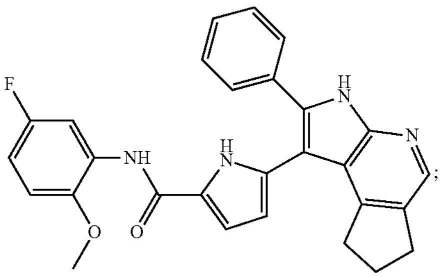

N-(5-fluoro-2-methoxyphenyl)-5-(2-phenyl-3,6,7,8-tetrahydrocyclopenta[d]pyrrolo[2,3-b]pyridin-1-yl)-1H-pyrrole-2-carboxamide Compound 106

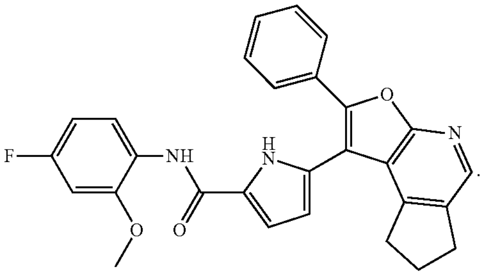

N-(4-fluoro-2-methoxyphenyl)-5-(2-phenyl-7,8-dihydro-6H-cyclopenta[d]furo[2,3-b]pyridin-1-yl)-1H-pyrrole-2-carboxamide In some embodiments, the R group substitution pattern and substituents thereof of Compounds 1-79 can be applied to any of the Compounds 80-106. As such, the data from the Compounds 1-79 may provide indications of the corresponding Compounds 80-106. In some aspects, the substitution pattern and substituents thereof of the following compounds are applied to the core structures of Compounds 80-106: Compound 2—5-(1-cyclopentyl-4-(4-fluorophenyl)-1H-imidazol-5-yl)-N-(2,5-dimethoxyphenyl)furan-2-carboxamide; Compound 3-5-(1-cyclopentyl-4-(4-fluorophenyl)-1H-imidazol-5-yl)-N-(2,5-difluorophenyl)furan-2-carboxamide; Compound 13—N-(2-bromophenyl)-5-(1-cyclopentyl-4-(4-fluorophenyl)-1H-imidazol-5-yl)furan-2-carboxamide; Compound 14—N-(2-chlorophenyl)-5-(1-cyclopentyl-4-(4-fluorophenyl)-1H-imidazol-5-yl)furan-2-carboxamide; Compound 18—5-(1-cyclopentyl-4-(4-fluorophenyl)-1H-imidazol-5-yl)-N-(2,4-dimethoxyphenyl)furan-2-carboxamide; Compound 24—5-(1-cyclopentyl-4-(4-fluorophenyl)-1H-imidazol-5-yl)-N-(2-fluorophenyl)furan-2-carboxamide; Compound 27—methyl 2-(5-(1-cyclopentyl-4-(4-fluorophenyl)-1H-imidazol-5-yl)furan-2-carboxamido)benzoate; Compound 47—5-(1-cyclopentyl-4-(4-fluorophenyl)-1H-imidazol-5-yl)-N-(p-tolyl)furan-2-carboxamide; or Compound 50—5-(1-cyclopentyl-4-(4-fluorophenyl)-1H-imidazol-5-yl)-N-(2-methoxyphenyl)furan-2-carboxamide.

In some embodiments, the compound has one of the following structures of Compounds A-1 through A-63:

Compound A-1

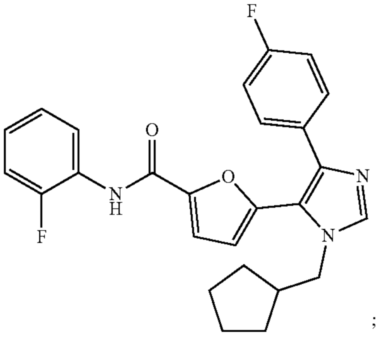

;

5-(1-(cyclopentylmethyl)-4-(4-fluorophenyl)-1H-imidazol-5-yl)-N-(2-fluorophenyl)furan-2-carboxamide Compound A-2

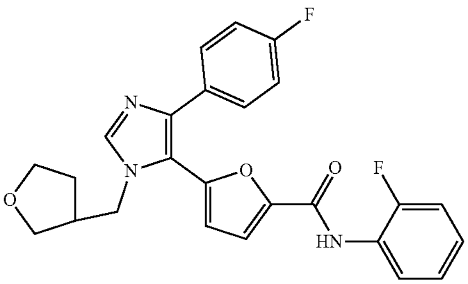

N-(2-fluorophenyl)-5-(4-(4-fluorophenyl)-1-((tetrahydrofuran-3-yl)methyl)-1H-imidazol-5-yl)furan-2-carboxamide -continued Compound A-3

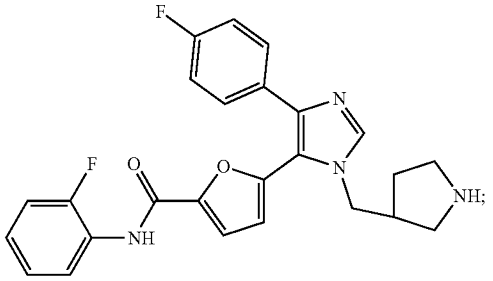

N-(2-fluorophenyl)-5-(4-(4-fluorophenyl)-1-(pyrrolidin-3-ylmethyl)-1H-imidazol-5-yl)furan-2-carboxamide Compound A-4

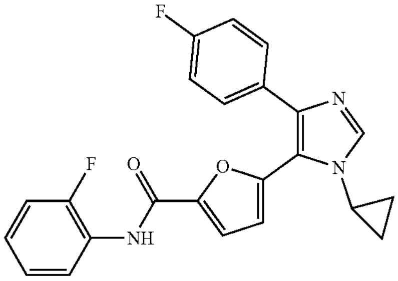

5-(1-cyclopropyl-4-(4-fluorophenyl)-1H-imidazol-5-yl)-N-(2-fluorophenyl)furan-2-carboxamide Compound A-5

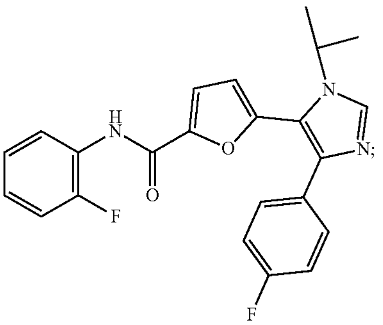

N-(2-fluorophenyl)-5-(4-(4-fluorophenyl)-1-isopropyl-1H-imidazol-5-yl)furan-2-carboxamide Compound A-6

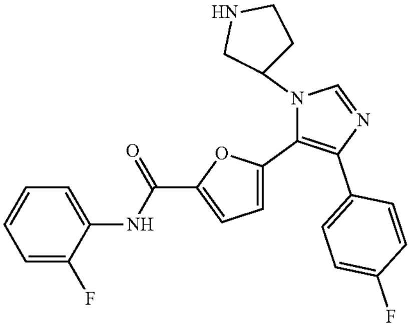

N-(2-fluorophenyl)-5-(4-(4-fluorophenyl)-1-(pyrrolidin-3-yl)-1H-imidazol-5-yl)furan-2-carboxamide -continued Compound A-8

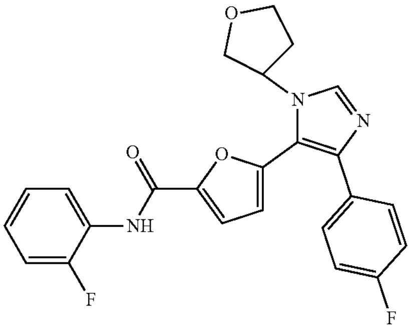

N-(2-fluorophenyl)-5-(4-(4-fluorophenyl)-1-(tetrahydrofuran-3-yl)-1H-imidazol-5-yl)furan-2-carboxamide Compound A-9

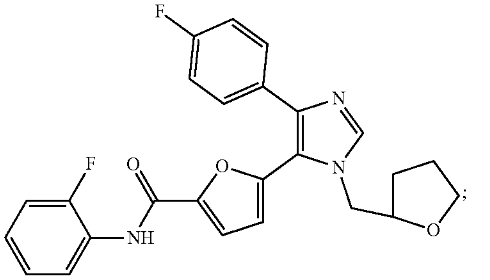

N-(2-fluorophenyl)-5-(4-(4-fluorophenyl)-1-((tetrahydrofuran-2-yl)methyl)-1H-imidazol-5-yl)furan-2-carboxamide Compound A-10

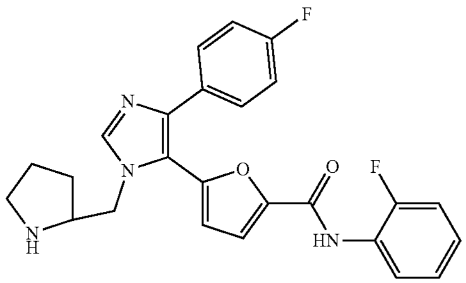

N-(2-fluorophenyl)-5-(4-(4-fluorophenyl)-1-(pyrrolidin-2-ylmethyl)-1H-imidazol-5-yl)furan-2-carboxamide Compound A-11

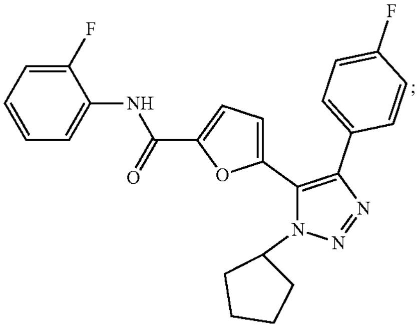

5-(1-cyclopentyl-4-(4-fluorophenyl)-1H-1,2,3-triazol-5-yl)-N-(2-fluorophenyl)furan-2-carboxamide -continued Compound A-12

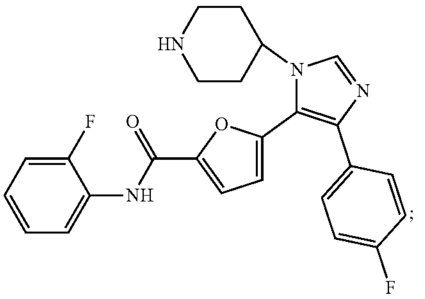

N-(2-fluorophenyl)-5-(4-(4-fluorophenyl)-1-(piperidin-4-yl)-1H-imidazol-5-yl)furan-2-carboxamide Compound A-13

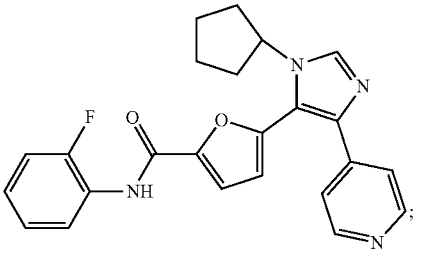

5-(1-cyclopentyl-4-(pyridin-4-yl)-1H-imidazol-5-yl)-N-(2-fluorophenyl)furan-2-carboxamide Compound A-14

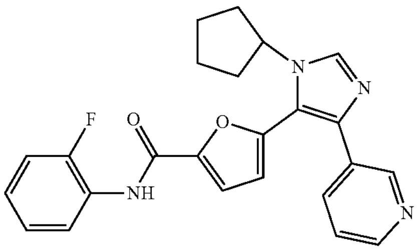

5-(1-cyclopentyl-4-(pyridin-3-yl)-1H-imidazol-5-yl)-N-(2-fluorophenyl)furan-2-carboxamide Compound A-15

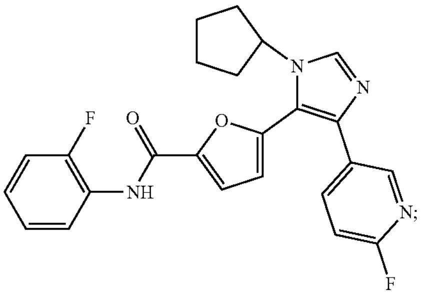

5-(1-cyclopentyl-4-(6-fluoropyridin-3-yl)-1H-imidazol-5-yl)-N-(2-fluorophenyl)furan-2-carboxamide -continued Compound A-16

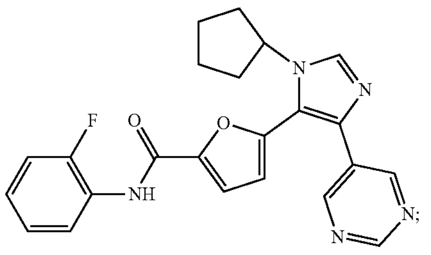

5-(1-cyclopentyl-4-(pyrimidin-5-yl)-1H-imidazol-5-yl)-N-(2-fluorophenyl)furan-2-carboxamide Compound A-17

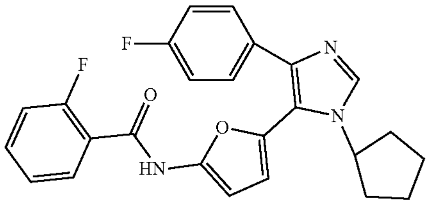

N-(5-(1-cyclopentyl-4-(4-fluorophenyl)-1H-imidazol-5-yl)furan-2-yl)-2-fluorobenzamide Compound A-18

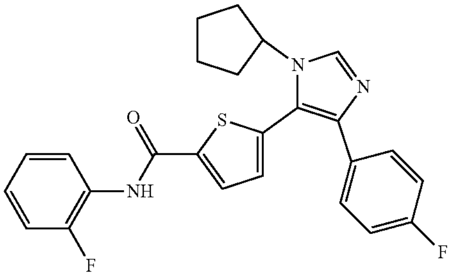

5-(1-cyclopentyl-4-(4-fluorophenyl)-1H-imidazol-5-yl)-N-(2-fluorophenyl)thiophene-2-carboxamide Compound A-19

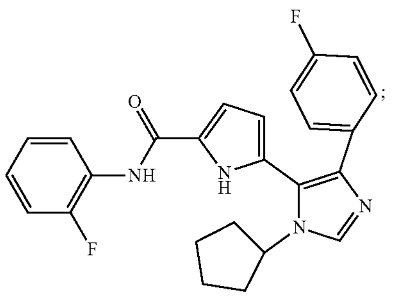

5-(1-cyclopentyl-4-(4-fluorophenyl)-1H-imidazol-5-yl)-N-(2-fluorophenyl)-1H-pyrrole-2-carboxamide -continued Compound A-20

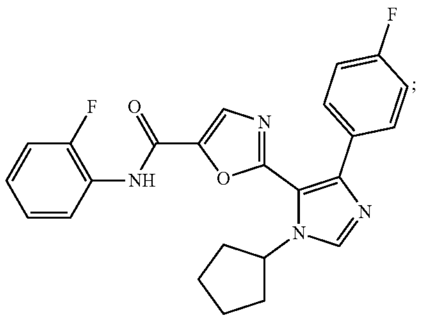

2-(1-cyclopentyl-4-(4-fluorophenyl)-1H-imidazol-5-yl)-N-(2-fluorophenyl)-oxazole-5-carboxamide Compound A-21

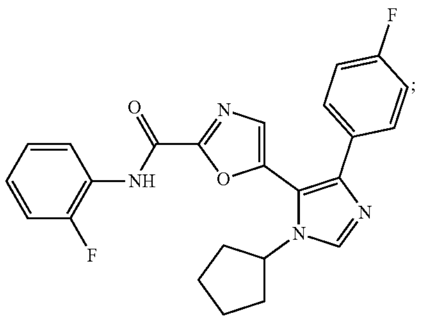

5-(1-cyclopentyl-4-(4-fluorophenyl)-1H-imidazol-5-yl)-N-(2-fluorophenyl)-oxazole-2-carboxamide Compound A-22

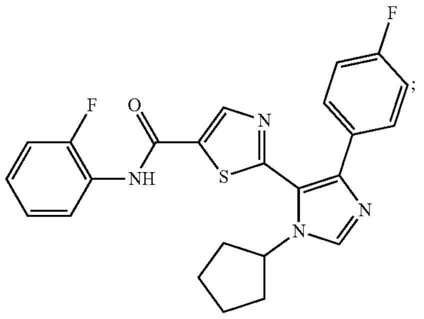

2-(1-cyclopentyl-4-(4-fluorophenyl)-1H-imidazol-5-yl)-N-(2-fluorophenyl)thiazole-5-carboxamide Compound A-23

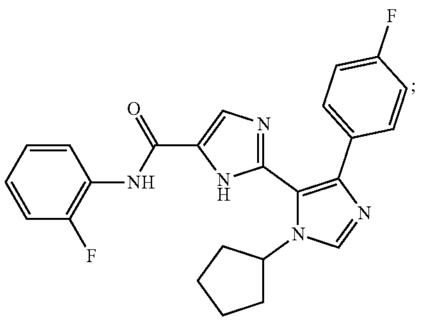

3′-cyclopentyl-N-(2-fluorophenyl)-5′-(4-fluorophenyl)-1H-3′H-[2,4′-biimidazole]-5-carboxamide -continued Compound A-24

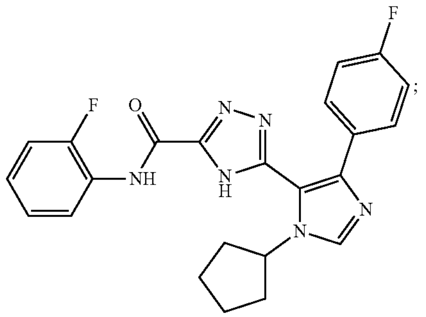

5-(1-cyclopentyl-4-(4-fluorophenyl)-1H-imidazol-5-yl)-N-(2-fluorophenyl)-4H-1,2,4-triazole-3-carboxamide Compound A-25

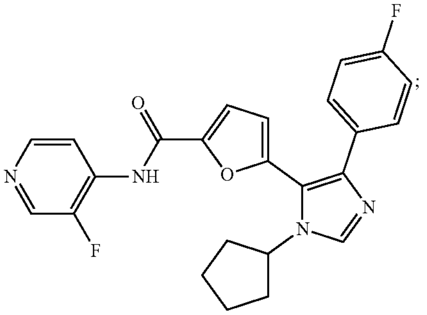

5-(1-cyclopentyl-4-(4-fluorophenyl)-1H-imidazol-5-yl)-N-(3-fluoropyridin-4-yl)furan-2-carboxamide Compound A-26

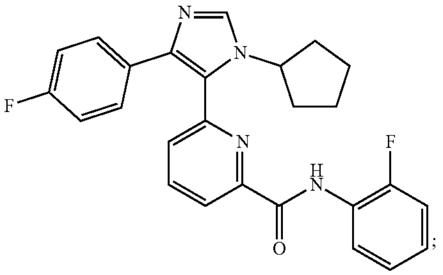

6-(1-cyclopentyl-4-(4-fluorophenyl)-1H-imidazol-5-yl)-N-(2-fluorophenyl)picolinamide Compound A-36

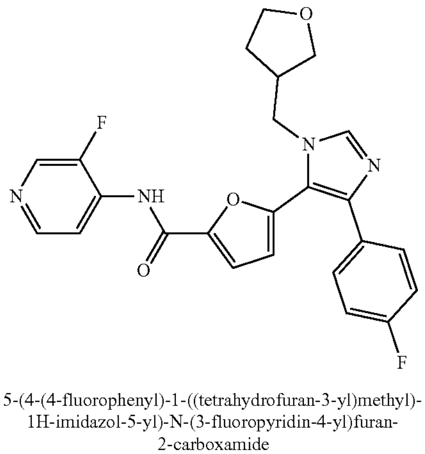

5-(4-(4-fluorophenyl)-1-((tetrahydrofuran-3-yl)methyl)-1H-imidazol-5-yl)-N-(3-fluoropyridin-4-yl)furan-2-carboxamide -continued Compound A-37

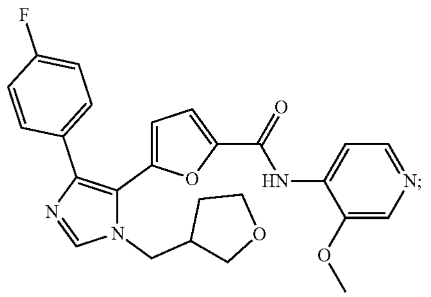

5-(4-(4-fluorophenyl)-1-((tetrahydrofuran-3-yl)methyl)-1H-imidazol-5-yl)-N-(3-methoxypyridin-4-yl)furan-2-carboxamide Compound A-38

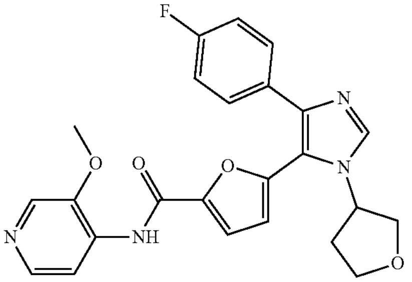

5-(4-(4-fluorophenyl)-1-(tetrahydrofuran-3-yl)-1H-imidazol-5-yl)-N-(3-methoxy pyridin-4-yl)furan-2-carboxamide Compound A-39

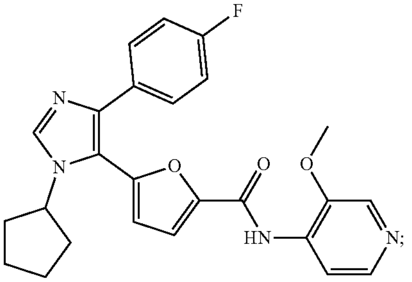

5-(1-cyclopentyl-4-(4-fluorophenyl)-1H-imidazol-5-yl)-N-(3-methoxypyridin-4-yl)furan-2-carboxamide Compound A-40

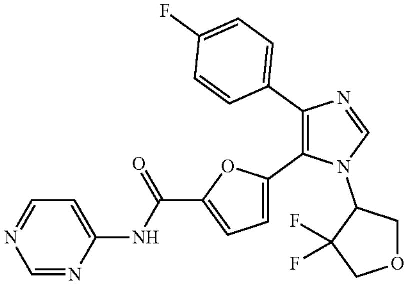

5-(1-(4,4-difluorotetrahydrofuran-3-yl)-4-(4-fluorophenyl)-1H-imidazol-5-yl)-N-(pyrimidin-4-yl)furan-2-carboxamide -continued Compound A-41

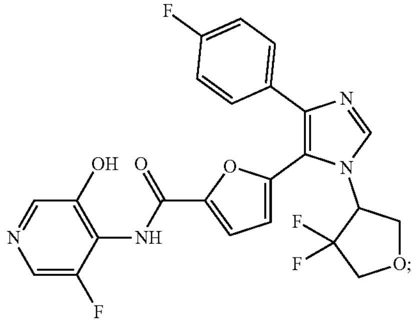

5-(1-(4,4-difluorotetrahydrofuran-3-yl)-4-(4-fluorophenyl)-1H-imidazol-5-yl)-N-(3-fluoro-5-hydroxypyridin-4-yl)furan-2-carboxamide Compound A-42

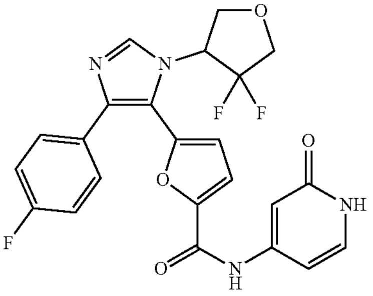

5-(1-(4,4-difluorotetrahydrofuran-3-yl)-4-(4-fluorophenyl)-1H-imidazol-5-yl)-N-(2-oxo-1,2-dihydroxypyridin-4-yl)furan-2-carboxamide Compound A-43

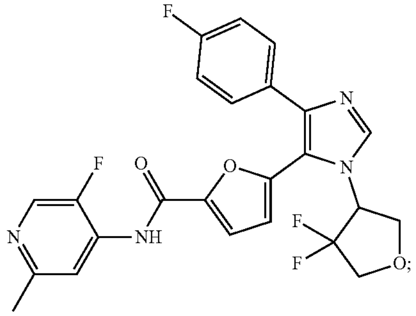

5-(1-(4,4-difluorotetrahydrofuran-3-yl)-4-(4-fluorophenyl)-1H-imidazol-5-yl)-N-(5-fluoro-2-methylpyridin-4-yl)furan-2-carboxamide Compound A-44

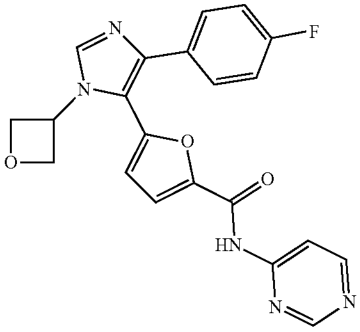

5-(4-(4-fluorophenyl)-1-(oxetan-3-yl)-1H-imidazol-5-yl)-N-(pyrimidin-4-yl)furan-2-carboxamide -continued Compound A-45

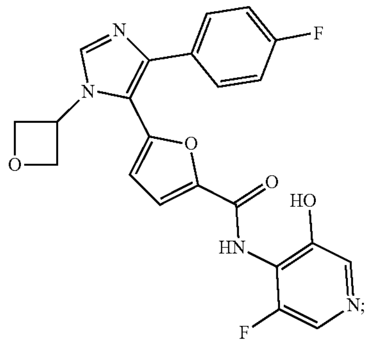

N-(3-fluoro-5-hydroxypyridin-4-yl)-5-(4-(4-fluorophenyl)-1-(oxetan-3-yl)-1H-imidazol-5-yl)furan-2-carboxamide Compound A-46

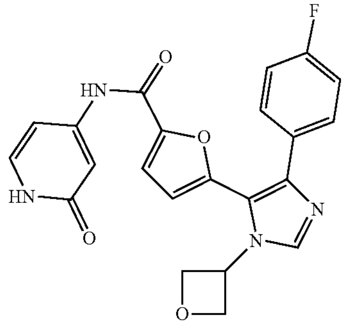

5-(4-(4-fluorophenyl)-1-(oxetan-3-yl)-1H-imidazol-5-yl)-N-(2-oxo-1,2-dihydropyridin-4-yl)furan-2-carboxamide Compound A-47

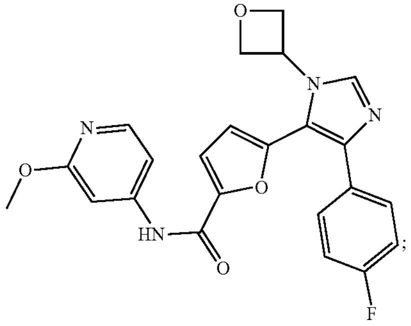

5-(4-(4-fluorophenyl)-1-(oxetan-3-yl)-1H-imidazol-5-yl)-N-(2-methoxy pyridin-4-yl)furan-2-carboxamide -continued Compound A-48

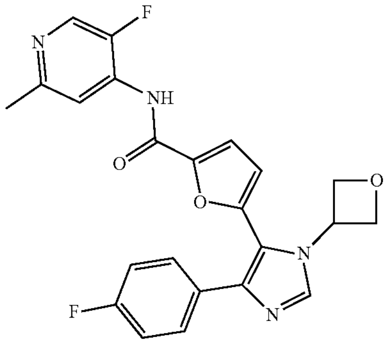

N-(5-fluoro-2-methylpyridin-4-yl)-5-(4-(4-fluorophenyl)-1-(oxetan-3-yl)-1H-imidazol-5-yl)furan-2-carboxamide Compound A-49

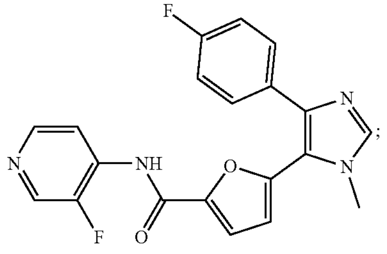

5-(4-(4-fluorophenyl)-1-methyl-1H-imidazol-5-yl)-N-(3-fluoropyridin-4-yl)furan-2-carboxamide Compound A-50

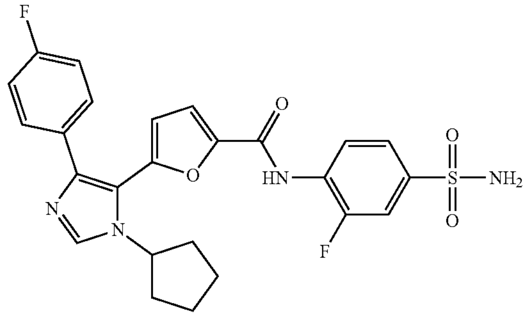

5-(1-cyclopentyl-4-(4-fluorophenyl)-1H-imidazol-5-yl)-N-(2-fluoro-4-sulfamoylphenyl)furan-2-carboxamide Compound A-51

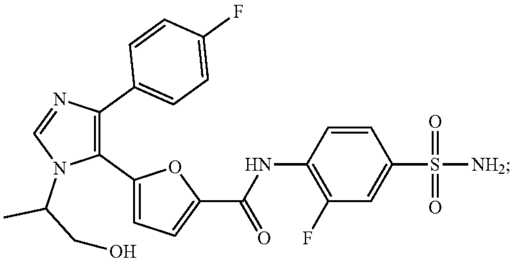

N-(2-fluoro-4-sulfamoylphenyl)-5-(4-(4-fluorophenyl)-1-(1-hydroxypropan-2-yl)-1H-imidazol-5-yl)furan-2-carboxamide -continued Compound A-52

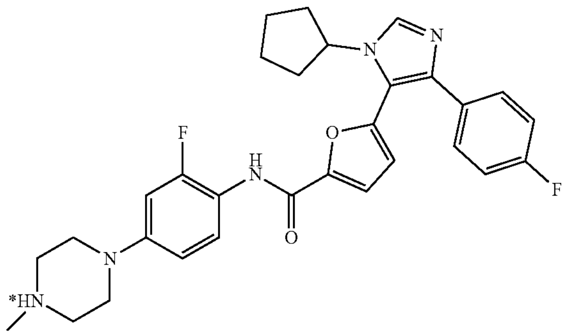

4-(4-(5-(1-cyclopentyl-4-(4-fluorophenyl)-1H-imidazol-5-yl)furan-2-carboxamido)-3-fluorophenyl)-1-methylpiperazin-1-ium Compound A-53

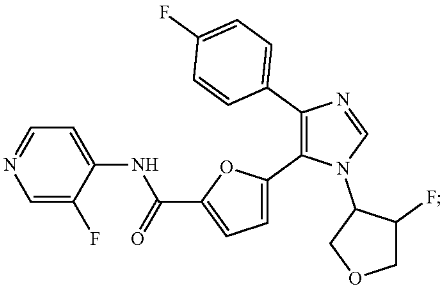

5-(4-(4-fluorophenyl)-1-(4-fluorotetrahydrofuran-3-yl)-1H-imidazol-5-yl)-N-(3-fluoropyridin-4-yl)furan-2-carboxamide Compound A-54

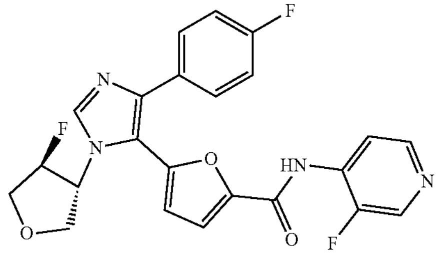

rac-5-(4-(4-fluorophenyl)-1-((3R,4S)-4-fluorotetrahydrofuran-3-yl)-1H-imidazol-5-yl)-N-(3-fluoropyridin-4-yl)furan-2-carboxamide Compound A-55

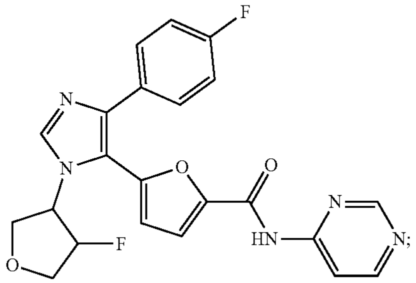

5-(4-(4-fluorophenyl)-1-(4-fluorotetrahydrofuran-3-yl)-1H-imidazol-5-yl)-N-(pyrimidin-4-yl)furan-2-carboxamide -continued Compound A-56

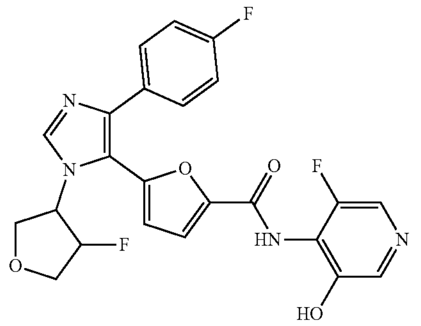

N-(3-fluoro-5-hydroxypyridin-4-yl)-5-(4-(4-fluorophenyl)-1-(4-fluorotetrahydrofuran-3-yl)-1H-imidazol-5-yl)furan-2-carboxamide Compound A-57

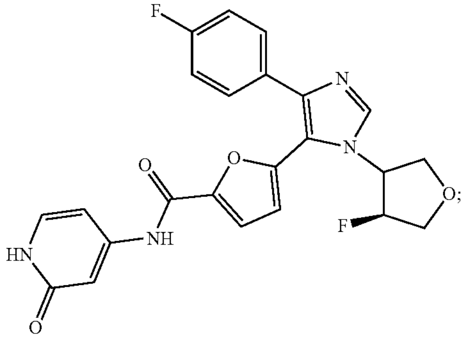

rac-5-(4-(4-fluorophenyl)-1-((4R)-4-fluorotetra hydrofuran-3-yl)-1H-imidazol-5-yl)-N-(2-oxo-1,2-dihydropyridin-4-yl)furan-2-carboxamide Compound A-58

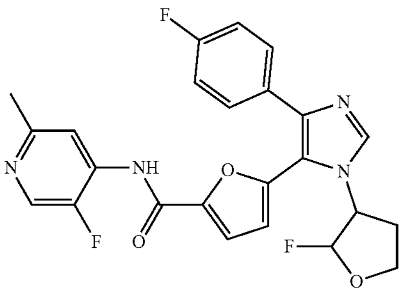

N-(5-fluoro-2-methylpyridin-4-yl)-5-(4-(4-fluorophenyl)-1-(4-fluorotetrahydrofuran-3-yl)-1H-imidazol-5-yl)furan-2-carboxamide -continued Compound A-60

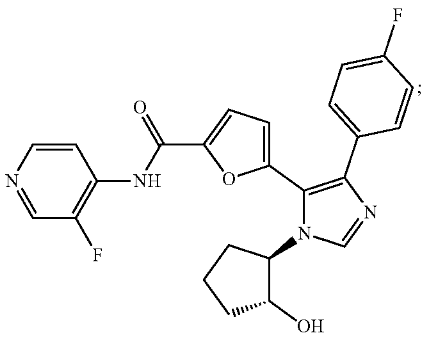

rac-5-(4-(4-fluorophenyl)-1-((1R,2R)-2-hydroxycyclopentyl)-1H-imidazol-5-yl)-N-(3-fluoropyridin-4-yl)furan-2-carboxamide Compound A-61

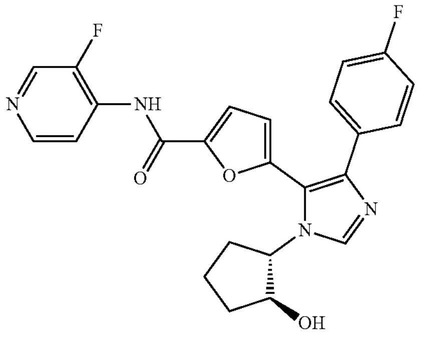

rac-5-(4-(4-fluorophenyl)-1-((1R,2R)-2-hydroxycyclopentyl)-1H-imidazol-5-yl)-N-(3-fluoropyridin-4-yl)furan-2-carboxamide Compound A-62

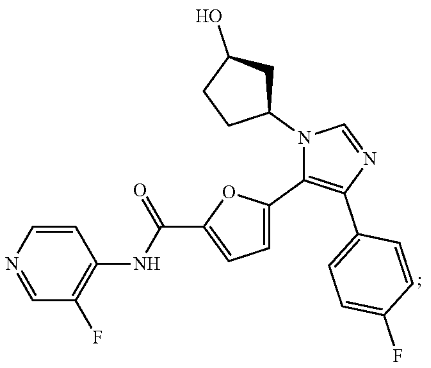

rac-5-(4-(4-fluorophenyl)-1-((1R,3S)-3-hydroxycyclopentyl)-1H-imidazol-5-yl)-N-(3-fluoropyridin-4-yl)furan-2-carboxamide -continued Compound A-63

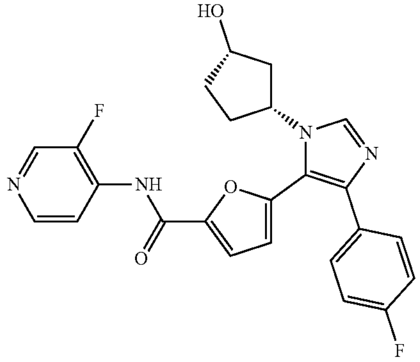

rac-5-(4-(4-fluorophenyl)-1-((1R,3S)-3-hydroxycyclopentyl)-1H-imidazol-5-yl)-N-(3-fluoropyridin-4-yl)furan-2-carboxamide In some embodiments, the compound has one of the following structures of Compounds B-1 through B-79:

Compound B-1

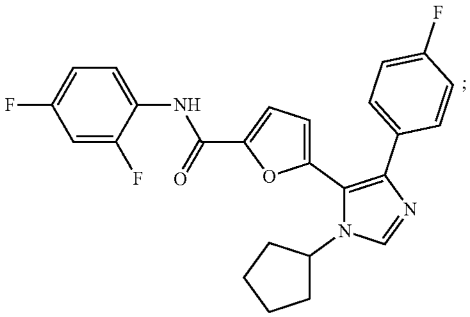

5-(1-cyclopentyl-4-(4-fluorophenyl)-1H-imidazol-5-yl)-N-(2,4-difluorophenyl) furan-2-carboxamide Compound B-2

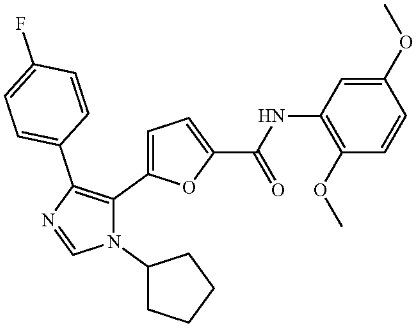

5-(1-cyclopentyl-4-(4-fluorophenyl)-1H-imidazol-5-yl)-N-(2,5-dimethoxyphenyl) furan-2-carboxamide -continued Compound B-3

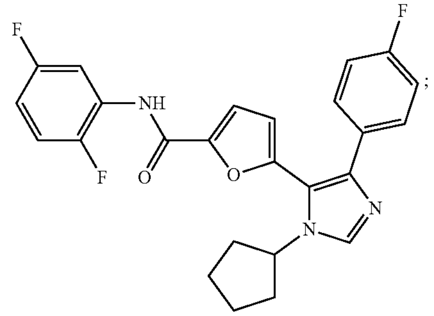

5-(1-cyclopentyl-4-(4-fluorophenyl)-1H-imidazol-5-yl-N-(2,5-difluorophenyl) furan-2-carboxamide Compound B-4

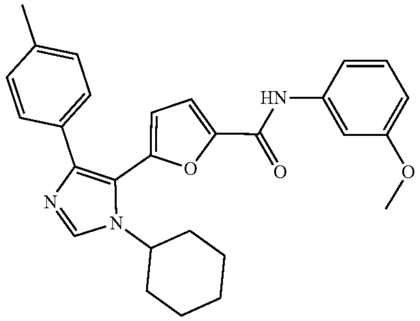

5-(1-cyclohexyl-4-(p-tolyl)-1H-imidazol-5-yl)-N-(3-methoxy phenyl)furan-2-carboxamide Compound B-5

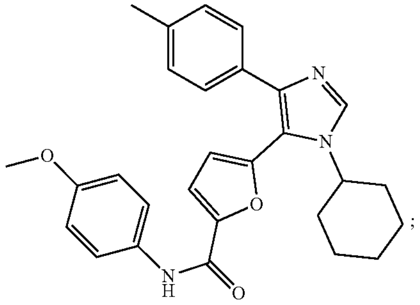

5-(1-cyclohexyl-4-(p-tolyl)-1H-imidazol-5-yl)-N-(4-methoxyphenyl) furan-2-carboxamide Compound B-6

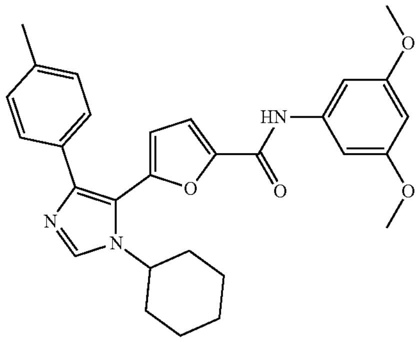

5-(1-cyclohexyl-4-(p-tolyl)-1H-imidazol-5-yl)-N-(3,5-dimethoxy phenyl)furan-2-carboxamide -continued Compound B-7

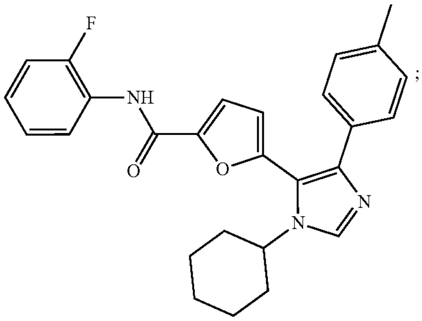

5-(1-cyclohexyl-4-(p-tolyl)-1H-imidazol-5-yl)-N-(2-fluoro phenhyl)furan-2-carboxamide Compound B-8

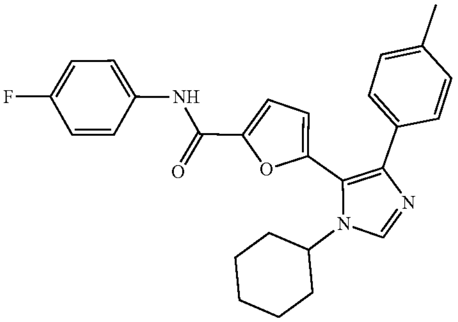

5-(1-cyclohexyl-4-(p-tolyl)-1H-imidazol-5-yl)-N-(4-fluoro phenyl)furan-2-carboxamide Compound B-9

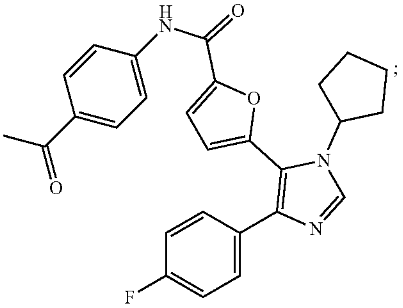

N-(4-acetylphenyl)-5-(1-cyclo pentyl-4-(4-fluorophenyl)-1H-imidazol-5-yl)furan-2-carboxamide Compound B-10

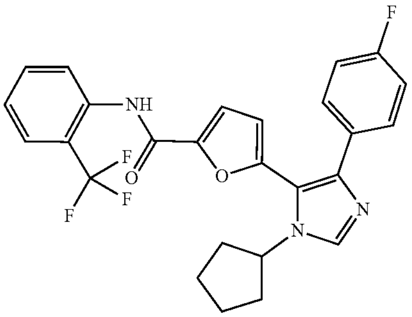

5-(1-cylcopentyl-4-(4-fluorophenyl)-1H-imidazol-5-yl)-N-(2-trifluoromethyl) phenyl)furan-2-carboxamide -continued Compound B-11

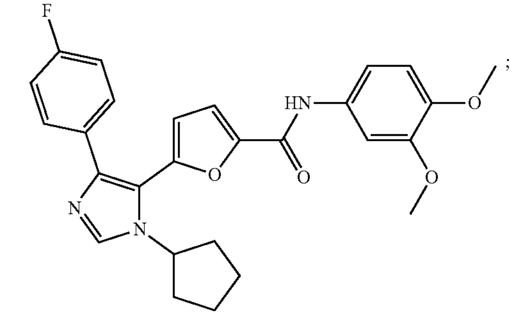

5-(1-cyclopentyl-4-(4-fluorophenyl)-1H-imidazol-5-yl)-N-(3,4-dimethoxy phenyl)furan-2-carboxamide Compound B-12

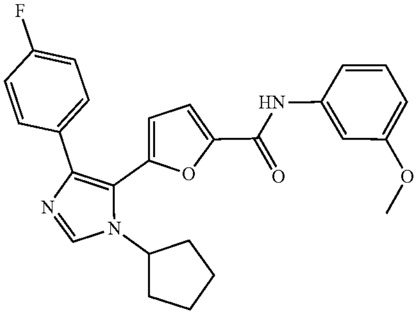

5-(1-cyclopentyl-4-(4-fluorophenyl)-1H-imidazol-5-yl)-N-(3-methoxy phenyl)furan-2-carboxamide Compound B-13

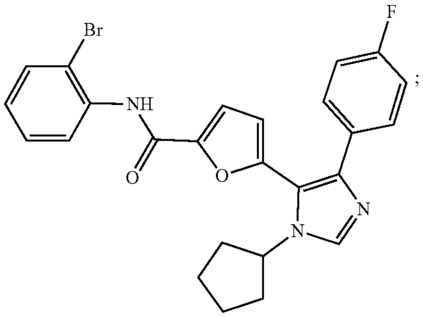

N-(2-bromophenyl)-5-(1-cyclopentyl-4-(4-fluorophenyl)-1H-imidazol-5-yl)furan-2-carboxamide Compound B-14

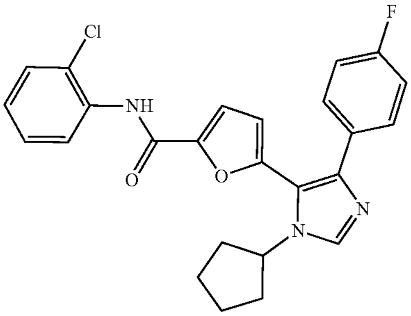

N-(2-chlorphenyl)-5-(1-cyclopentyl-4-(4-fluorophenyl)-1H-imidazol-5-yl)furan-2-carboxamide -continued Compound B-15

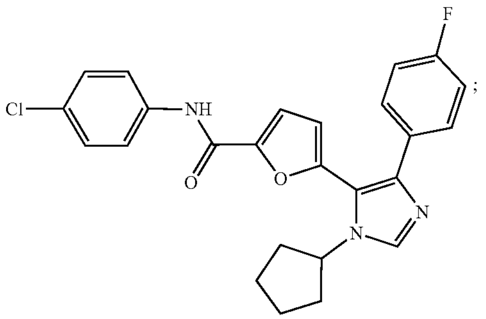

N-(4-chlorphenyl)-5-(1-cyclopentyl-4-(4-fluorophenyl)-1H-imidazol-5-yl)furan-2-carboxamide Compound B-16

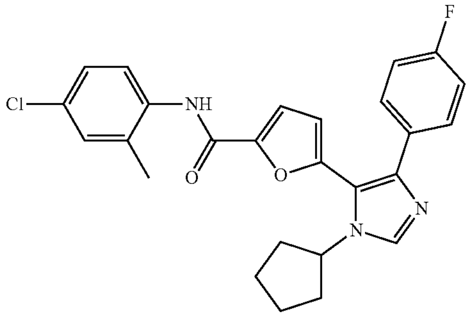

N-(4-chloro-2-methylphenyl)-5-(1-cyclopentyl-4-(4-fluorophenyl)-1H-imidazol-5-yl)furan-2-carboxamide Compound B-17

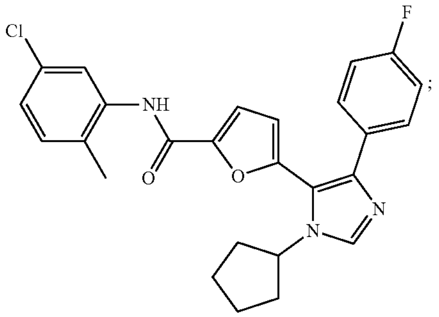

N-(5-chloro-2-methylphenyl)-5-(1-cyclopentyl-4-(4-fluorophenyl)-1H-imidazol-5-yl)furan-2-carboxamide -continued Compound B-18

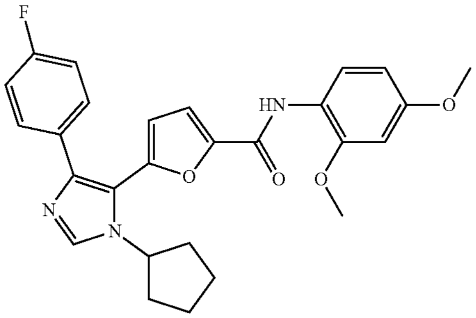

5-(1-cyclopentyl-4-(4-fluorophenyl)-1H-imidazol-5-yl)-N-(2,4-dimethoxy phenyl)furan-2-carboxamide Compound B-19

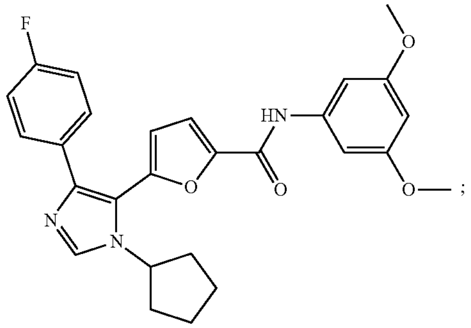

5-(1-cyclopentyl-4-(4-fluorophenyl)-1H-imidazol-5-yl)-N-(3,5-dimethoxy phenyl)furan-2-carboxamide Compound B-20

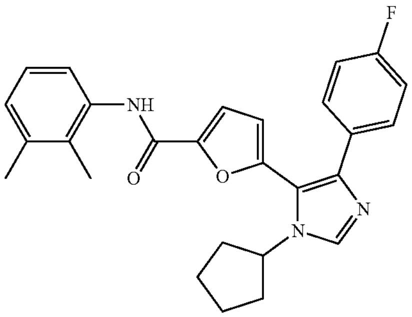

5-(1-cyclopentyl-4-(4-fluorophenyl)-1H-imidazol-5-yl)-N-(2,3-dimethyl phenyl)furan-2-carboxamide -continued Compound B-21

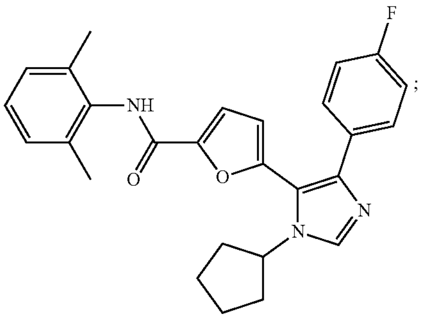

5-(1-cyclopentyl-4-(4-fluoro phenyl)-1H-imidazol-5-yl)-N-(2,6-dimethyl phenyl)furan-2-carboxamide Compound B-22

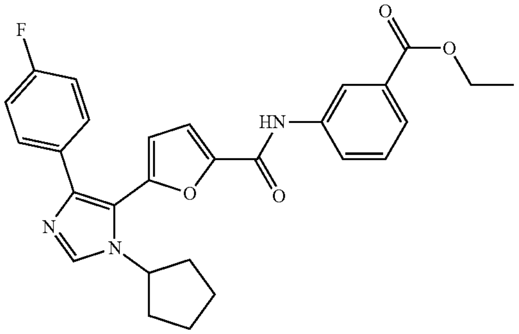

ethyl 3-(5-(1-cyclopentyl-4-(4-fluoro phenyl)-1H-imidazol-5-yl)furan-2-carboxamido)benzoate Compound B-23

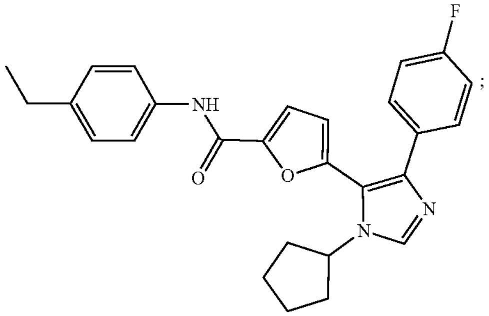

5-(1-cyclopentyl-4-(4-fluoro phenyl)-1H-imidazol-5-yl)-N-(4-ethylphenyl)furan-2-carboxamide -continued Compound B-24

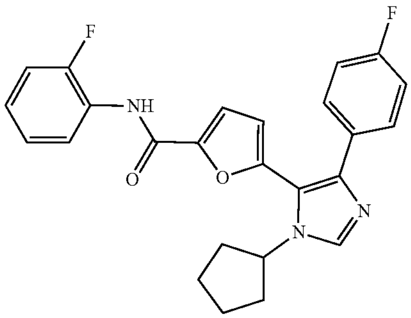

5-(1-cyclopentyl-4-(4-fluoro phenyl)-1H-imidazol-5-yl)-N-(2-fluoro phenyl)furan-2-carboxamide Compound B-25

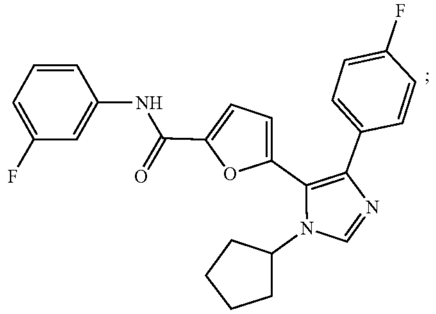

5-(1-cyclopentyl-4-(4-fluoro phenyl)-1H-imidazol-5-yl)-N-(3-fluoro phenyl)furan-2-carboxamide Compound B-26

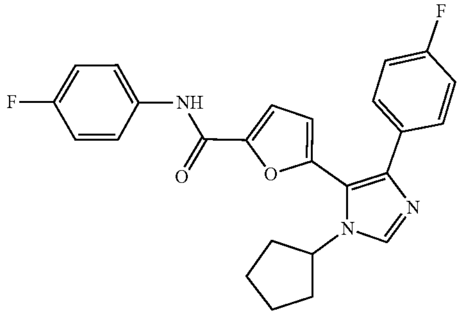

5-(1-cyclopentyl-4-(4-fluoro phenyl)-1H-imidazol-5-yl)-N-(4-fluoro phenyl)furan-2-carboxamide -continued Compound B-27

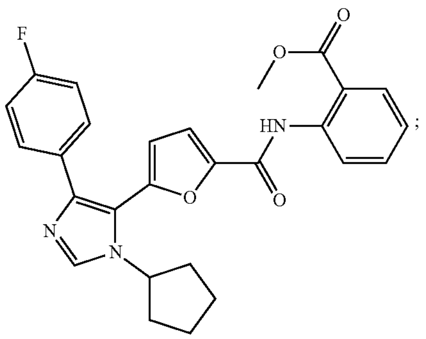

methyl 2-(5-(1-cyclopentyl-4-(4-fluorophenyl)-1H-imidazol-5-yl)furan-2-carboxamido)benzoate Compound B-28

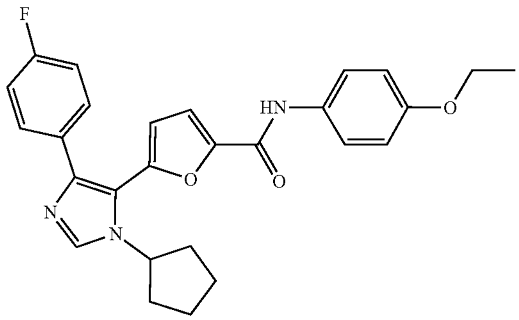

5-(1-cyclopentyl-4-(4-fluorophenyl)-1H-imidazol-5-yl)-N-(4-ethyoxyphenyl)furan-2-carboxamide Compound B-29

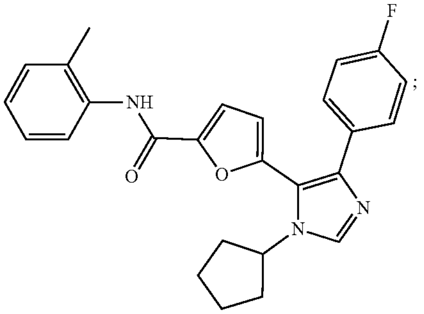

5-(1-cyclopentyl-4-(4-fluorophenyl)-1H-imidazol-5-yl)-N-(o-tolyl)furan-2-carboxamide -continued Compound B-30

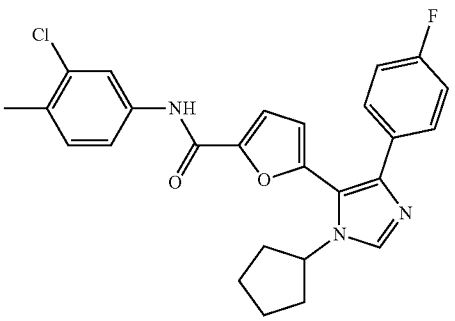

N-(3-chloro-4-methylphenyl)-5-(1-cyclopentyl-4-(4-fluorophenyl)-1H-imidazol-5-yl)furan-2-carboxamide Compound B-31

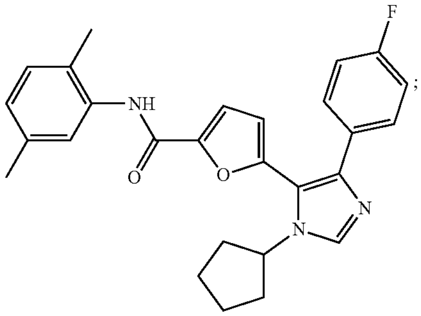

5-(1-cyclopentyl-4-(4-fluorophenyl)-1H-imidazol-5-yl)-N-(2,5-dimethylphenyl)furan-2-carboxamide Compound B-32

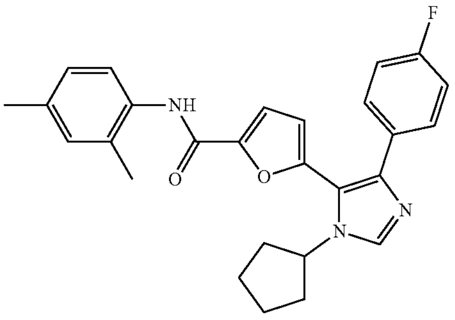

5-(1-cyclopentyl-4-(4-fluorophenyl)-1H-imidazol-5-yl)-N-(2,4-dimethylphenyl)furan-2-carboxamide -continued Compound B-33

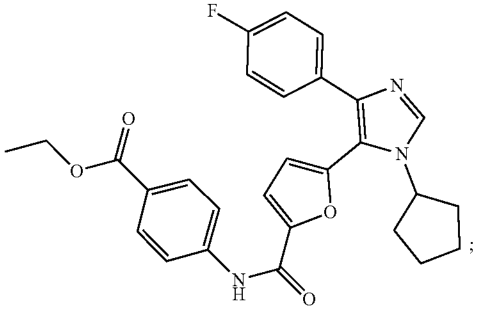

ethyl 4-(5-(1-cyclopentyl-4-(4-fluorophenyl)-1H-imidazol-5-yl)furan-2-carboxamido)benzoate Compound B-34

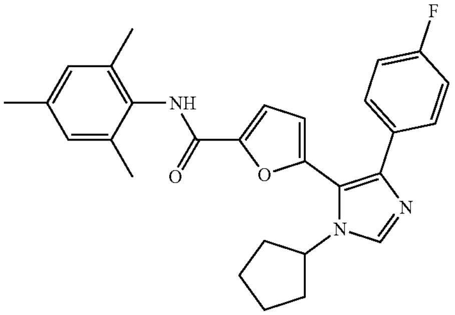

5-(1-cyclopentyl-4-(4-fluoro phenyl)-1H-imidazol-5-yl)-N-mesityl furan-2-carboxamide Compound B-35

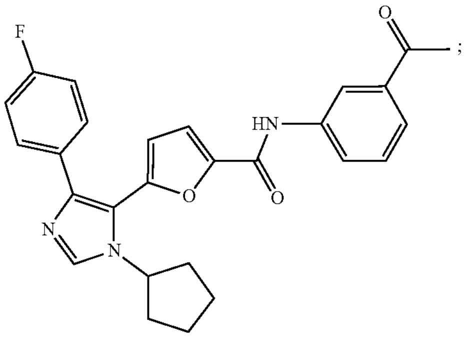

N-(3-acetylphenyl)-5-(1-cyclopentyl-4-(4-fluorophenyl)-1H-imidazol-5-yl)furan-2-carboxamide -continued Compound B-36

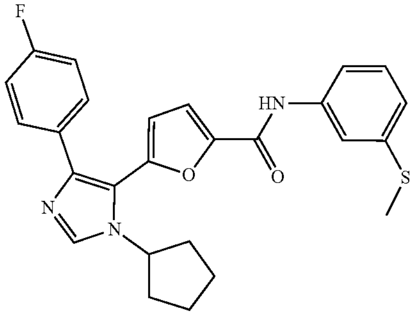

5-(1-cyclopentyl-4-(4-fluorophenyl)-1H-imidazol-5-yl)-N-(3-(methylthio) phenyl)furan-2-carboxamide Compound B-37

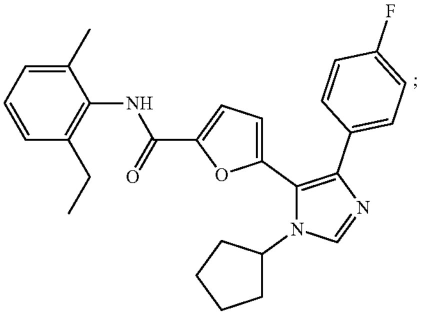

5-(1-cyclopentyl-4-(4-fluoro phenyl)-1H-imidazol-5-yl)-N-(2-ethyl-6-methyl phenyl)furan-2-carboxamide Compound B-38

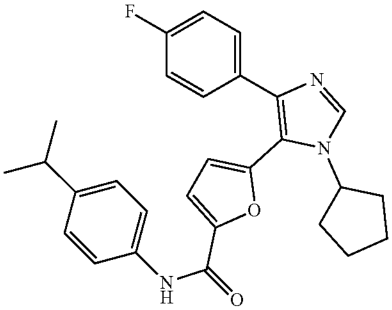

5-(1-cyclopentyl-4-(4-fluoro phenyl)-1H-imidazol-5-yl)-N-(4-isopropyl phenyl)furan-2-carboxamide Compound B-39

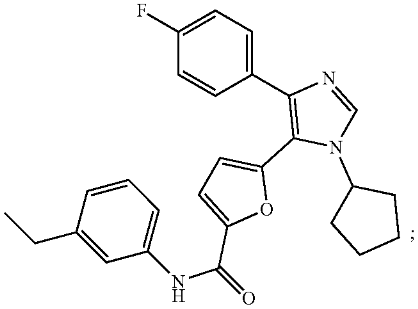

5-(1-cyclopentyl-4-(4-fluoro phenyl)-1H-imidazol-5-yl)-N-(3-ethyl phenyl)furan-2-carboxamide -continued Compound B-40

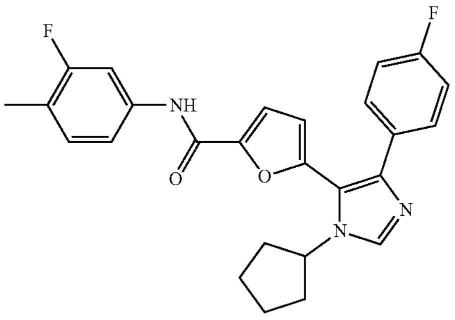

5-(1-cyclopentyl-4-(4-fluorophenyl)-1H-imidazol-5-yl)-N-(3-fluoro-4-methylphenyl)furan-2-carboxamide Compound B-41

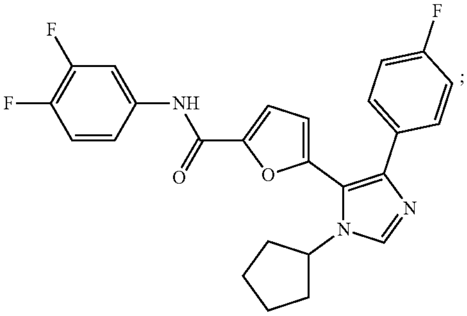

5-(1-cyclopentyl-4-(4-fluorophenyl)-1H-imidazol-5-yl)-N-(3,4-difluoro phenyl)furan-2-carboxamide Compound B-42

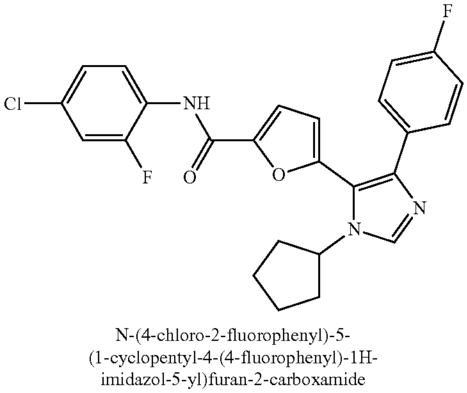

N-(4-chloro-2-fluorophenyl)-5-(1-cyclopentyl-4-(4-fluorophenyl)-1H-imidazol-5-yl)furan-2-carboxamide -continued Compound B-43

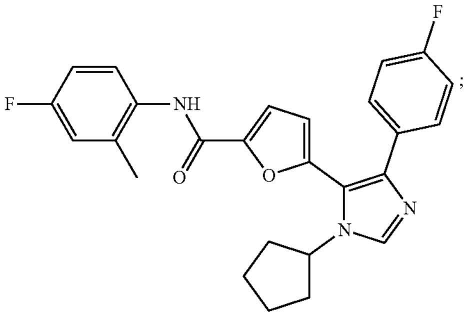

5-(1-cyclopentyl-4-(4-fluorophenyl)-1H-imidazol-5-yl)-N-(4-fluoro-2-methyl phenyl)furan-2-carboxamide Compound B-44

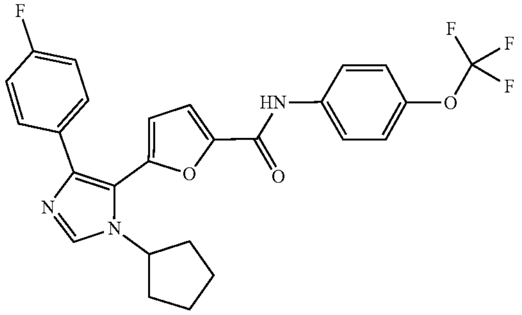

5-(1-cyclopentyl-4-(4-fluorophenyl)-1H-imidazol-5-yl)-N-(4-(trifluoro methoxy)phenyl)furan-2-carboxamide Compound B-45

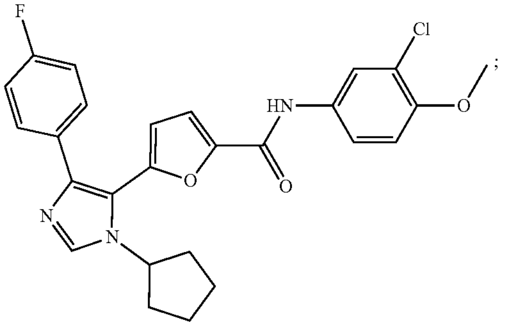

N-(3-chloro-4-methoxyphenyl)-5-(1-cyclopentyl-4-(4-fluorophenyl)-1H-imidazol-5-yl)furan-2-carboxamide Compound B-46

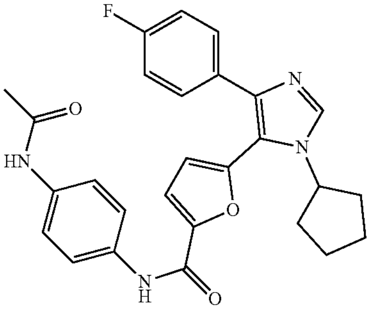

N-(4-acetamidophenyl)-5-(1-cyclo pentyl-4-(4-fluorophenyl)-1H-imidazol-5-yl)furan-2-carboxamide -continued Compound B-47

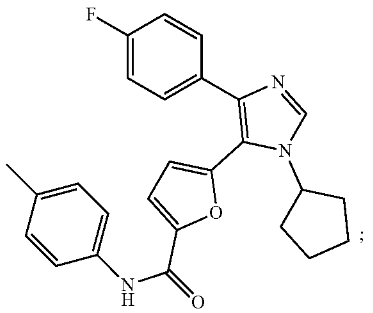

5-(1-cyclopentyl-4-(4-fluorophenyl)-1H-imidazol-5-yl)-N-(p-tolyl) furan-2-carboxamide Compound B-48

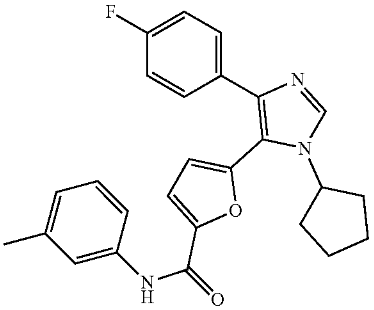

5-(1-cyclopentyl-4-(4-fluoro phenyl)-1H-imidazol-5-yl)-N-(m-tolyl)furan-2-carboxamide Compound B-49

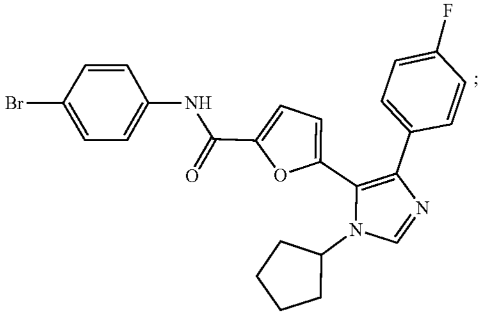

N-(4-bromophenyl)-5-(1-cyclo pentyl-4-(4-fluorophenyl)-1H-imidazol-5-yl)furan-2-carboxamide Compound B-50

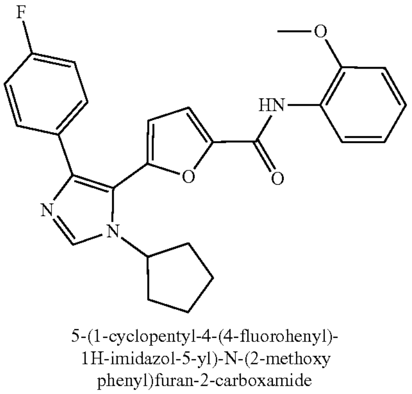

5-(1-cyclopentyl-4-(4-fluorohenyl)-1H-imidazol-5-yl)-N-(2-methoxy phenyl)furan-2-carboxamide -continued Compound B-51

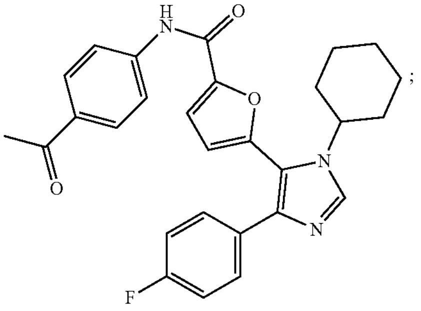

N-(4-acetylphenyl)-5-(1-cyclohexyl-4-(4-fluorophenyl)-1H-imidazol-5-yl)furan-2-carboxamide Compound B-52

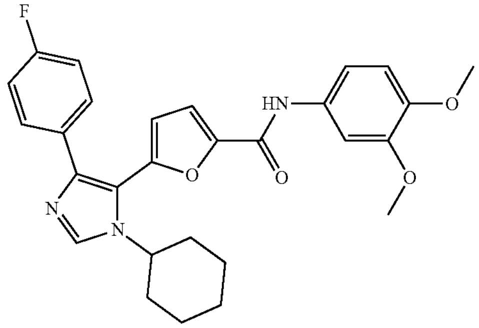

5-(1-cyclohexyl-4-(4-fluorophenyl)-1H-imidazol-5-yl)-N-(3,4-dimethoxy phenyl)furan-2-carboxamide Compound B-53

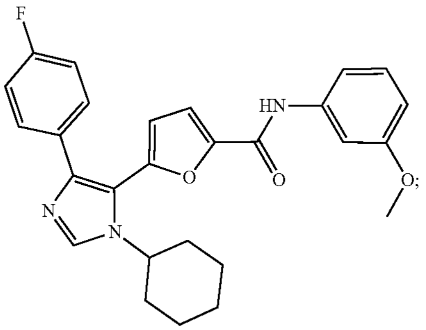

5-(1-cyclohexyl-4-(4-fluorophenyl)-1H-imidazol-5-yl)-N-(3-methoxy phenyl)furan-2-carboxamide -continued Compound B-54

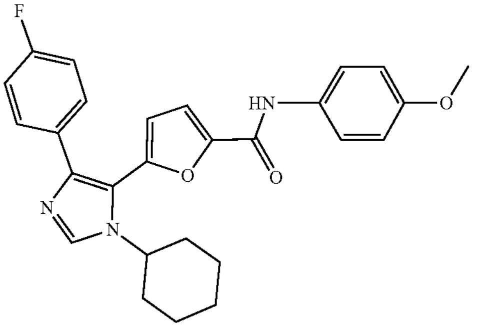

5-(1-cyclohexyl-4-(4-fluorophenyl)-1H-imidazol-5-yl)-N-(4-methoxy phenyl)furan-2-carboxamide Compound B-55

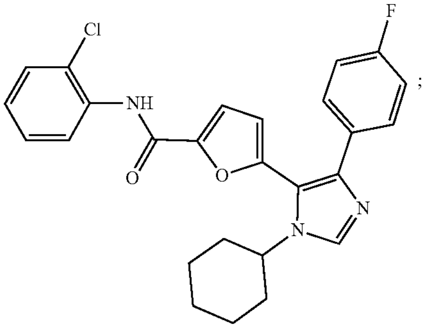

N-(2-chlorophenyl)-5-(1-cyclo hexyl-4-(4-fluorophenyl)-1H-imidazol-5-yl)furan-2-carboxamide Compound B-56

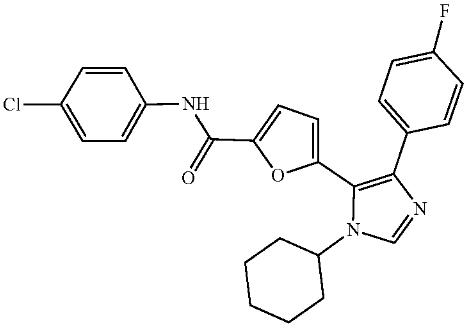

N-(4-chlorophenyl)-5-(1-cyclo hexyl-4-(4-fluorophenyl)-1H-imidazol-5-yl)furan-2-carboxamide -continued Compound B-57

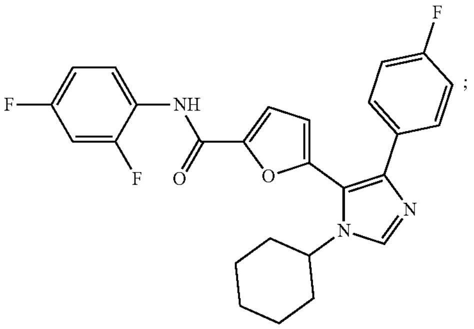

5-(1-cyclohexyl-4-(4-fluorophenyl)-1H-imidazol-5-yl)-N-(2,4-difluoro phenyl)furan-2-carboxamide Compound B-58

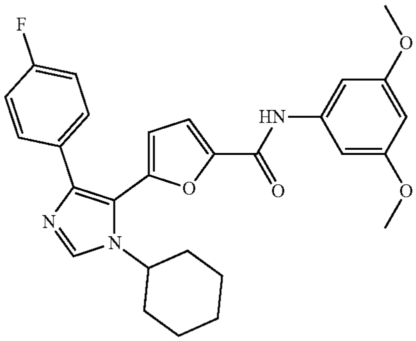

5-(1-cyclohexyl-4-(4-fluorophenyl)-1H-imidazol-5-yl)-N-(3,5-dimethoxy phenyl)furan-2-carboxamide Compound B-59

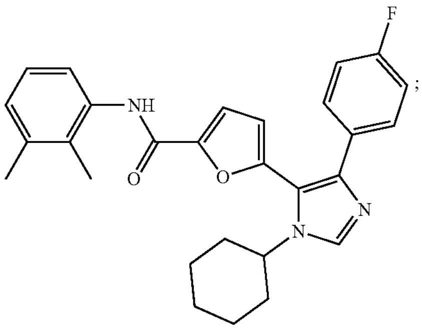

5-(1-cyclohexyl-4-(4-fluoro phenyl)-1H-imidazol-5-yl)-N-(2,3-dimethyl phenyl)furan-2-carboxamide Compound B-60

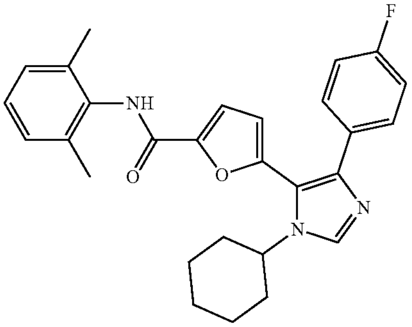

5-(1-cyclohexyl-4-(4-fluoro phenyl)-1H-imidazol-5-yl)-N-(2,6-dimethylphenyl)furan-2-carboxamide Compound B-61

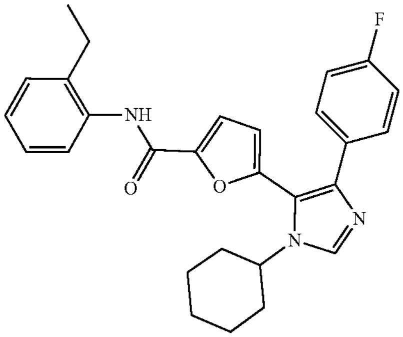

;

5-(1-cyclohexyl-4-(4-fluoro phenyl)-1H-imidazol-5-yl)-N-(2-ethyl phenyl)furan-2-carboxamide Compound B-62

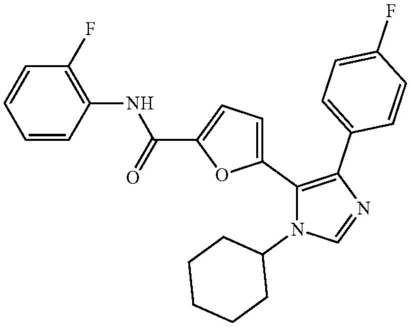

5-(1-cyclohexyl-4-(4-fluoro phenyl)-1H-imidazol-5-yl)-N-(2-fluoro phenyl)furan-2-carboxamide Compound B-63

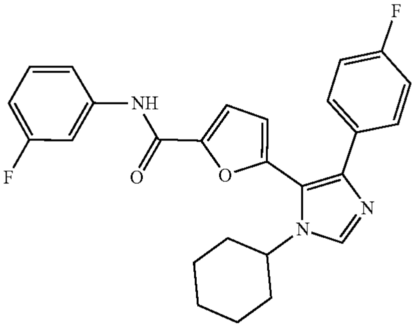

5-(1-cyclohexyl-4-(4-fluoro phenyl)-1H-imidazol-5-yl)-N-(3-fluoro phenyl)furan-2-carboxamide Compound B-64

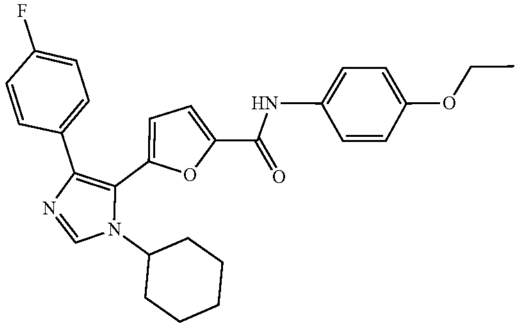

5-(1-cyclohexyl-4-(4-fluoro phenyl)-1H-imidazol-5-yl)-N-(4-ethoxyphenyl)furan-2-carboxamide Compound B-65

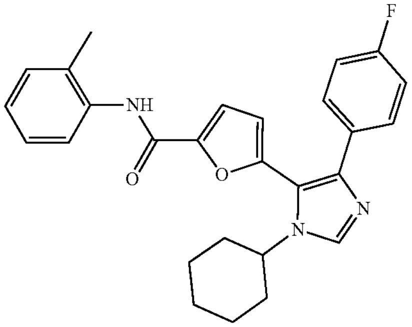

;

5-(1-cyclohexyl-4-(4-fluoro phenyl)-1H-imidazol-5-yl)-N-(o-tolyl)furan-2-carboxamide -continued Compound B-66

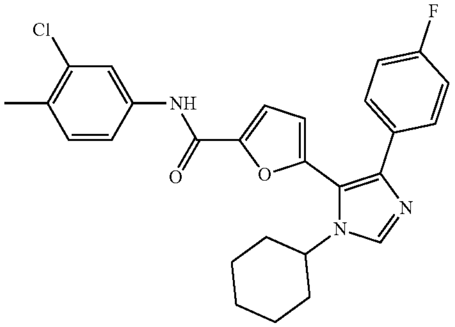

N-(3-chloro-4-methylphenyl)-5-(1-cyclohexyl-4-(4-fluorophenyl)-1H-imidazol-5-yl)furan-2-carboxamide Compound B-67

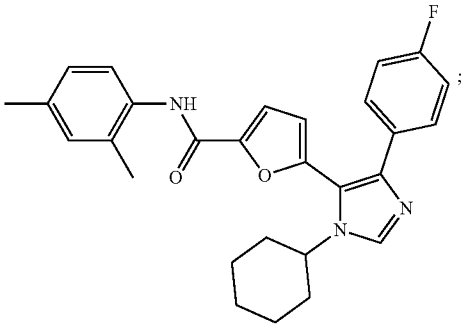

5-(1-cyclohexyl-4-(4-fluoro phenyl)-1H-imidazol-5-yl)-N-(2,4-dimethyl phenyl)furan-2-carboxamide Compound B-68

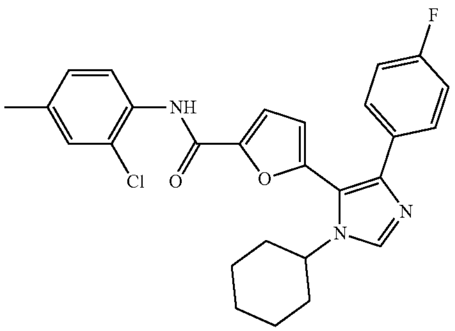

N-(2-chloro-4-methylphenyl)-5-(1-cyclohexyl-4-(4-fluorophenyl)-1H-imidazol-5-yl)furan-2-carboxamide -continued Compound B-69

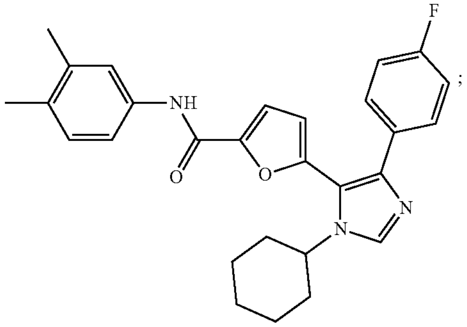

5-(1-cyclohexyl-4-(4-fluoro phenyl)-1H-imidazol-5-yl)-N-(3,4-dimethylphenyl)furan-2-carboxamide Compound B-70

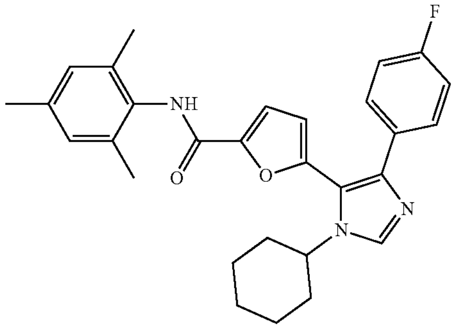

5-(1-cyclohexyl-4-(4-fluoro phenyl)-1H-imidazol-5-yl)-N-mesitylfuran-2-carboxamide Compound B-71

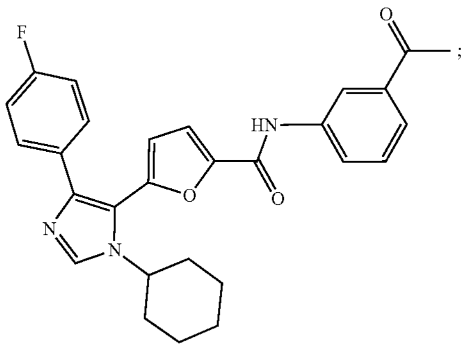

N-(3-acetylphenyl)-5-(1-cyclo hexyl-4-(4-fluorophenyl)-1H-imidazol-5-yl)furan-2-carboxamide -continued Compound B-72

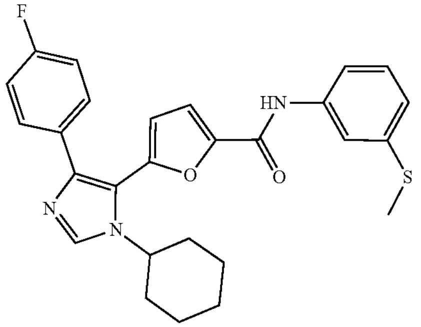

5-(1-cyclohexyl-4-(4-fluoro phenyl)-1H-imidazol-5-yl)-N-(3-(methylthio) phenyl)furan-2-carboxamide Compound B-73

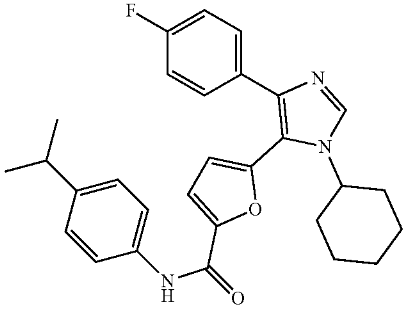

;

5-(1-cyclohexyl-4-(4-fluorophenyl)-1H-imidazol-5-yl)-N-(4-isopropyl phenyl)furan-2-carboxamide Compound B-74

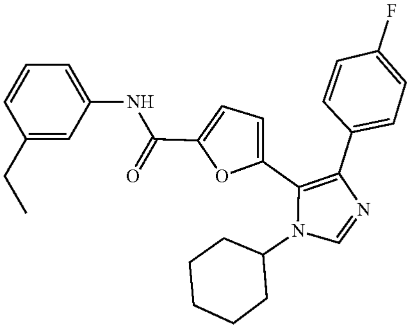

5-(1-cyclohexyl-4-(4-fluoro phenyl)-1H-imidazol-5-yl)-N-(3-ethylphenyl)furan-2-carboxamide Compound B-75

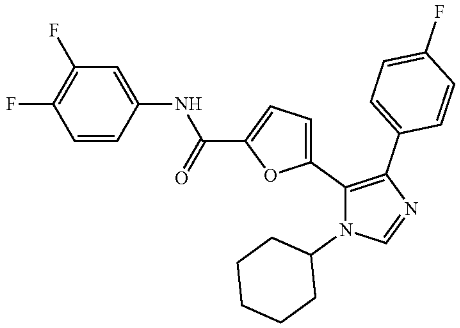

;

5-(1-cyclohexyl-4-(4-fluoro phenyl)-1H-imidazol-5-yl)-N-(3,4-difluorophenyl)furan-2-carboxamide -continued Compound B-76

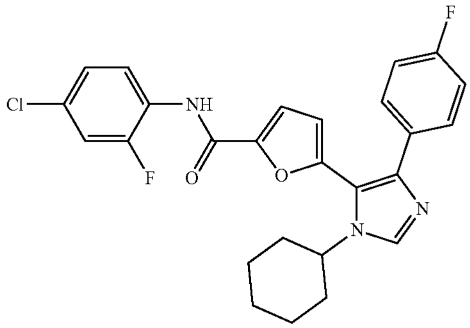

N-(4-chloro-2-fluorophenyl)-5-(1-cyclohexyl-4-(4-fluorophenyl)-1H-imidazol-5-yl)furan-2-carboxamide Compound B-77

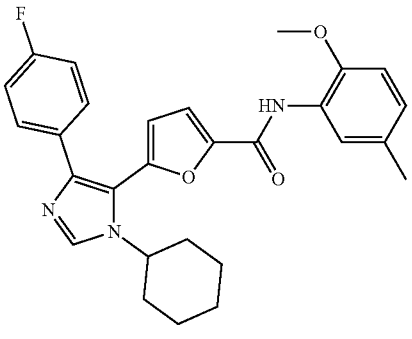

;

5-(1-cyclohexyl-4-(4-fluoro phenyl)-1H-imidazol-5-yl)-N-(2-methoxy-5-methylphenyl)furan-2-carboxamide Compound B-78

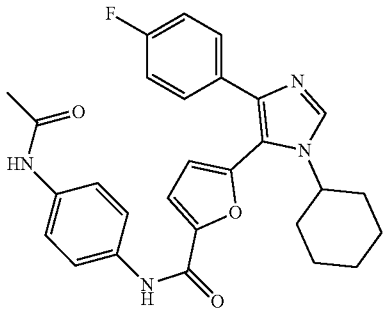

N-(4-acetamidophenyl)-5-(1-cyclohexyl-4-(4-fluorophenyl)-1H-imidazol-5-yl)furan-2-carboxamide -continued Compound B-79

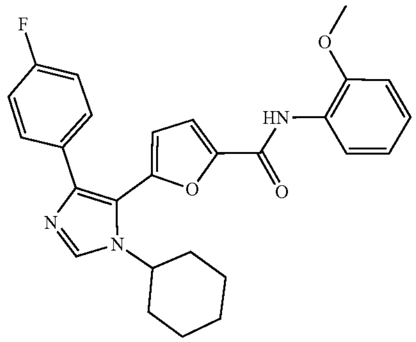

5-(1-cyclohexyl-4-(4-fluoro phenyl)-1H-imidazol-5-yl)-N-(2-methoxy phenyl)furan-2-carboxamide In some embodiments, the compound has one of the following structures of Compounds C-1 through C-59:

Compound C-1

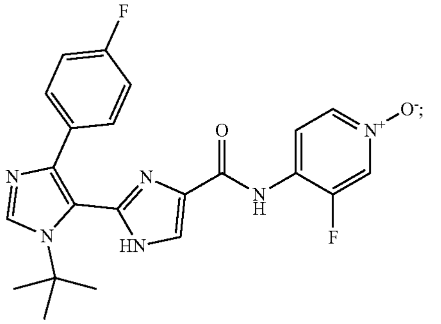

4-(3′-tert-butyl)-5′-(4-fluoro phenyl)-1H,3′H-[2,4′-biimidazole]-4-carboxamido)-3-fluoropyridine 1-oxide Compound C-2

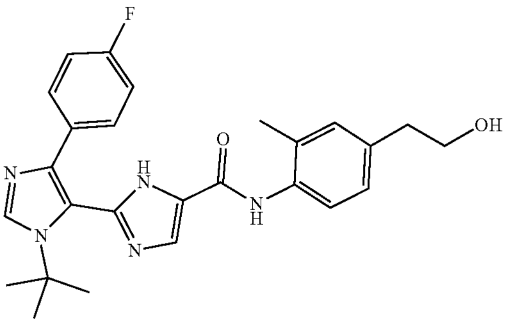

3′-(tert-butyl)-N-(2-chloro-4-(2-hydroxyethyl)phenyl)-5′-(4-fluorophenyl)-1H,3′H-[2,4′-biimidazole]-5-carboxamide -continued Compound C-3

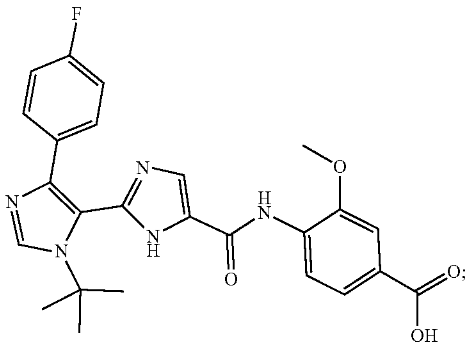

4-(3′-tert-butyl)-5′-(4-fluoro phenyl)-1H,3′H-[2,4′-biimidazole]-5-carboxamido)-3-methoxybenzoic acid Compound C-4

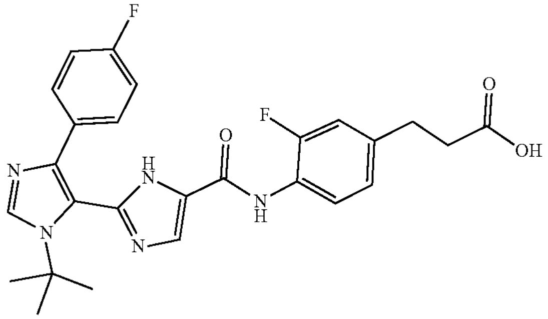

3-(4-(3′-tert-butyl)-5′-(4-fluoro phenyl)-1H,3′H-[2,4′-biimidazole]-5-carboxamido)-3-fluorophenyl)propanoic acid Compound C-5

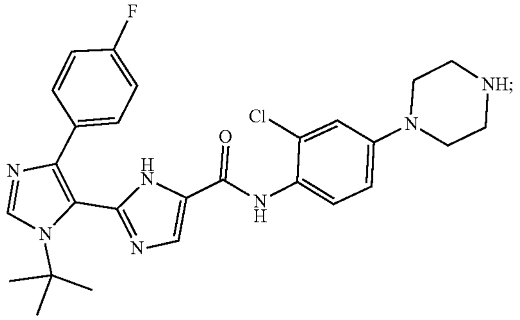

3′-(tert-butyl)-N-(2-chloro-4-(piperazin-1-yl)phenyl)-5′-(4-fluorophenyl)-1H,3′H-[2,4′-biimidazole]-5-carboxamide -continued Compound C-6

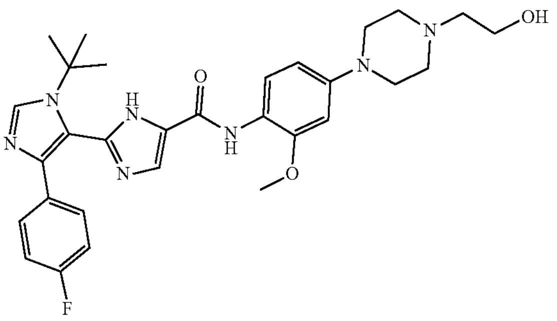

3′-(tert-butyl)-5′-(4-fluorophenyl)-N-(4-(4-(2-hydroxyethyl)piperazin-1-yl)-2-methoxyphenyl)-1H,3′H-[2,4′-biimidazole]-5-carboxamide Compound C-7

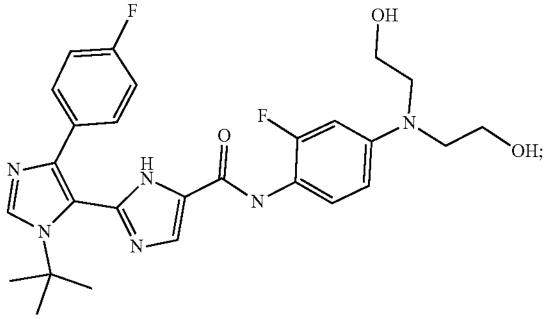

N-(4-bis(2-hydroxyethyl)amino)-2-fluorophenyl)-3′-(tert-butyl)-5′-(4-fluorophenyl)-1H,3′H-[2,4′-biimidazole]-5-carboxamide Compound C-8

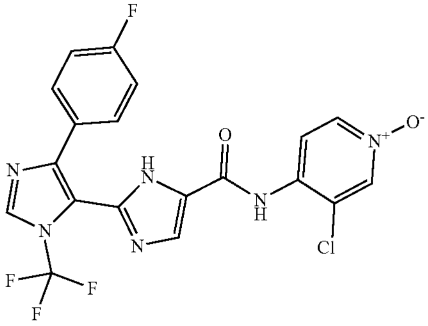

3-chloro-4-(5′-(4-fluorophenyl)-3′-(trifluoromethyl)-1H,3′H-[2,4′-biimidazole]-5-carboxamido)pyridine 1-oxide -continued Compound C-9

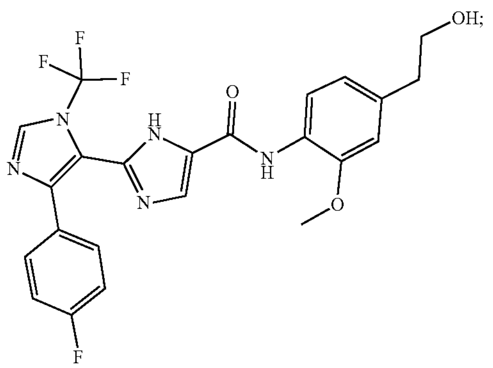

5′-(4-fluorophenyl)-N-(4-(2-hydroxyethyl)-2-methoxyphenyl)-3′-trifluoromethyl)-1H,3′H-[2,4′-biimidazole]-5-carboxamide Compound C-10

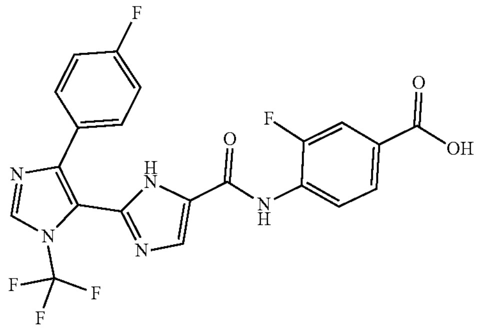

3-fluoro-4-(5′-(4-fluorophenyl)-3′-(trifluoromethyl)-1H,3′H-[2,4′-biimidazole]-5-carboxamido)benzoic acid Compound C-11

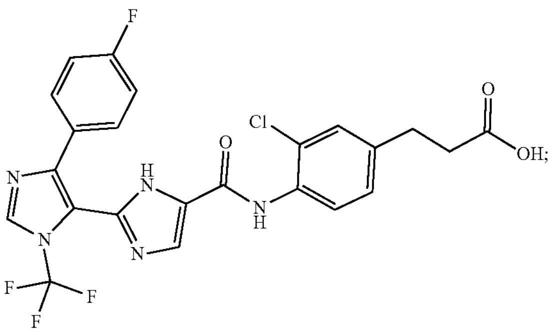

3-(3-chloro-4-(5′-(4-fluorophenyl)-3′-(trifluoromethyl)-1H,3′H-[2,4′-biimidazole]-5-carboxamido)phenyl)propanoic acid -continued Compound C-12

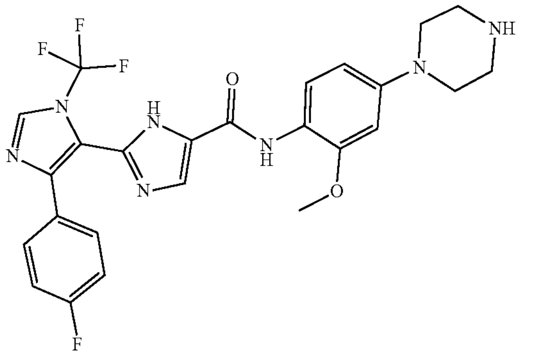

5′-(4-fluorophenyl)-N-(2-methoxy-4-(piperazin-1-yl)phenyl)-3′-trifluoromethyl)-1H,3′H-[2,4′-biimidazole]-5-carboxamide Compound C-13

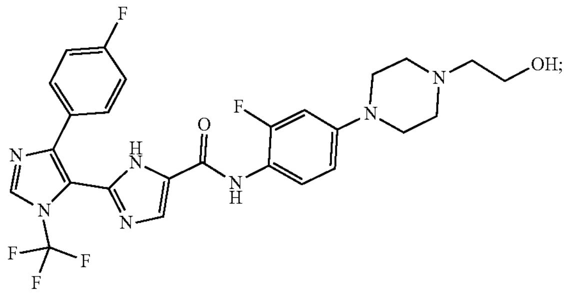

N-(2-fluoro-4-(4-(2-hydroxyethyl)piperazin-1-yl)phenyl)-5′-(4-fluorophenyl)-3′-(trifluoromethyl)-1H,3′H-[2,4′-biimidazole]-5-carboxamide Compound C-14

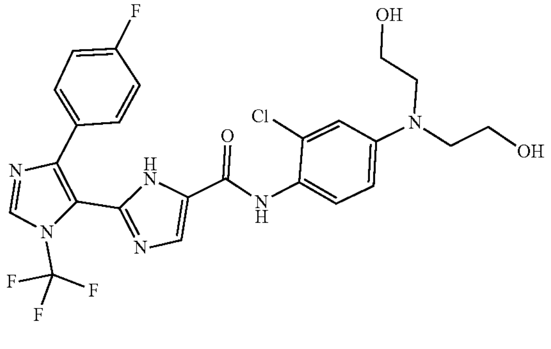

N-(4-(bis(2-hydroxyethyl)amino)-2-chlorophenyl)-5′-(4-fluorophenyl)-3′-(trifluoromethyl)-1H,3′H-[2,4′-biimidazole]-5-carboxamide -continued Compound C-15

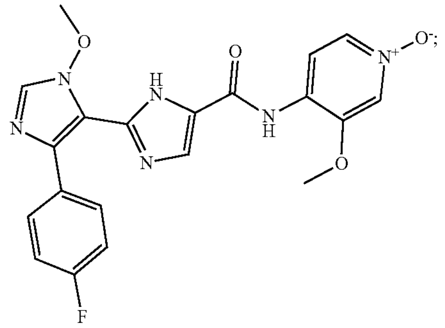

4-(5′-(4-fluorophenyl)-3′-methoxy-1H,3′H-[2,4′-biimidazole]-5-carboxamido)-3-methoxypyridine 1-oxide Compound C-16

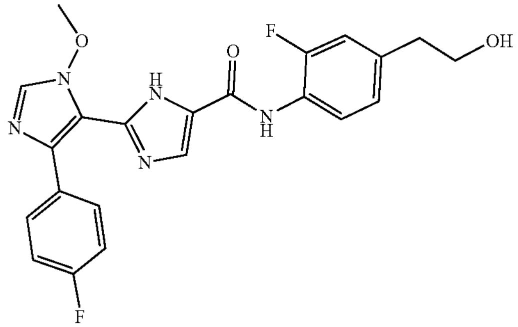

N-(2-fluoro-4-(2-hydroxyethyl)phenyl)-5′-(4-fluorophenyl)-3′-methoxy-1H,3′H-[2,4′-biimidazole]-5-carboxamide Compound C-17

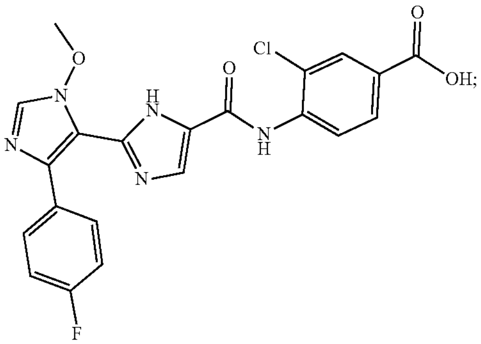

3-chloro-4-(5′-(4-fluorophenyl)-3′-methoxy-1H,3′H-[2,4′-biimidazole]-5-carboxamido)benzoic acid -continued Compound C-18

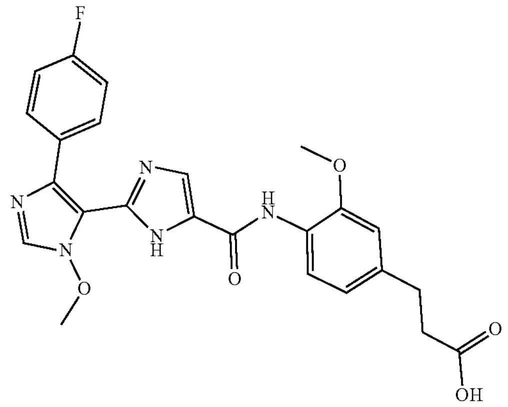

3-(4-(5′-(4-fluorophenyl)-3′-methoxy-1H,3′H-[2,4′-biimidazole]-5-carboxamido)-3-methoxyphenyl)propanoic acid Compound C-19

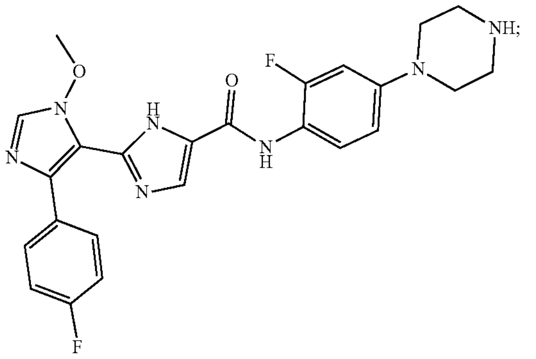

N-(2-fluoro-4-(piperazin-1-yl)phenyl)-5′-(4-fluorophenyl)-3′-methoxy-1H,3′H-[2,4′-biimidazole]-5-carboxamide Compound C-20

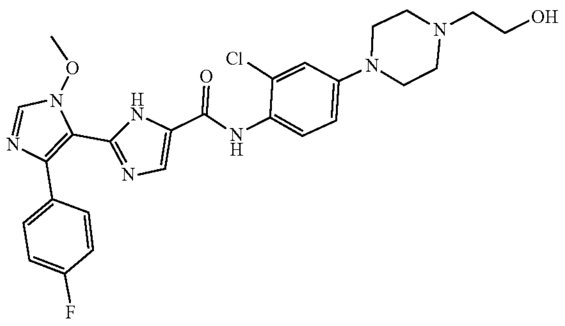

N-(2-chloro-4-(4-(2-hydroxyethyl)piperazin-1-yl)phenyl)-5′-(4-fluorophenyl)-3′-methoxy-1H,3′H-[2,4′-biimidazole]-5-carboxamide -continued Compound C-21

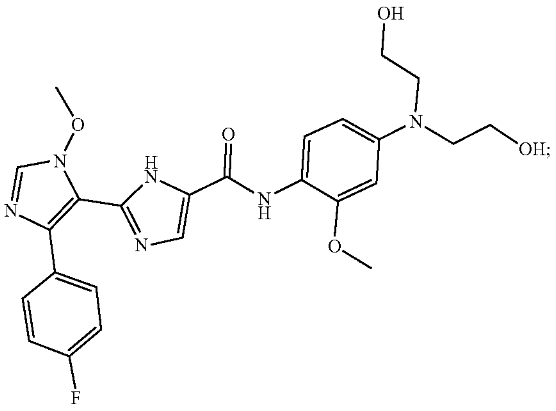

N-(4-(bis(2-hydroxyethyl)amino)-2-methoxyphenyl) 5′-(4-fluorophenyl)-3′-methoxy-1H,3′H-[2,4′-biimidazole]-5-carboxamide Compound C-22

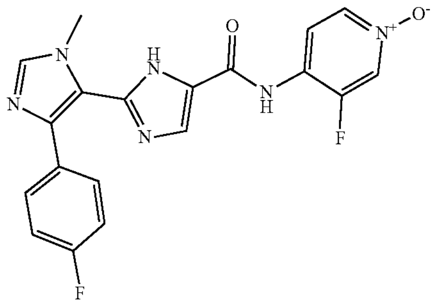

3-fluoro-4-(5′-(4-fluorophenyl)-3′-methyl-1H,3′H-[2,4′-biimidazole]-5-carboxamido)pyridine 1 oxide Compound C-23

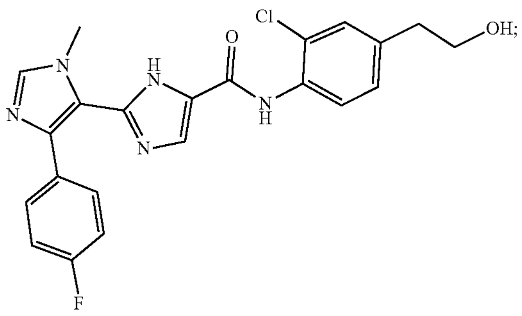

N-(2-chloro-4-(2-hydroxyethyl)phenyl)-5′-(4-fluorophenyl)-3′-methyl-1H,3′H-[2,4′-biimidazole]-5-carboxamide -continued Compound C-24

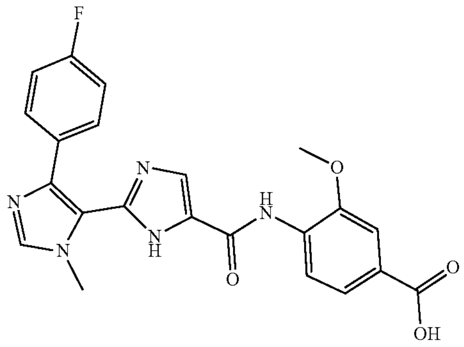

4-(5′-(4-fluorophenyl)-3′-methyl-1H,3′H-[2,4′-biimidazole]-5-carboxamido)-3-methoxybenzoic acid Compound C-25

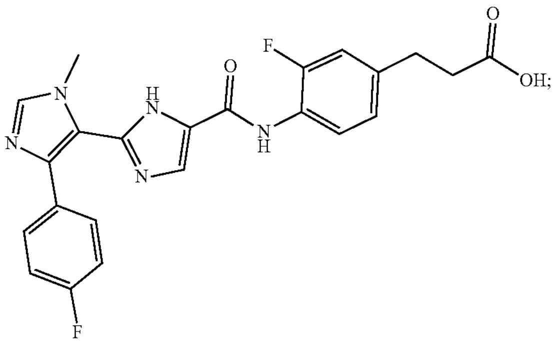

3-(3-fluoro-4-(5′-(4-fluorophenyl)-3′-methyl-1H,3′H-[2,4′-biimidazole]-5-carboxamido)phenyl)propanoic acid Compound C-26

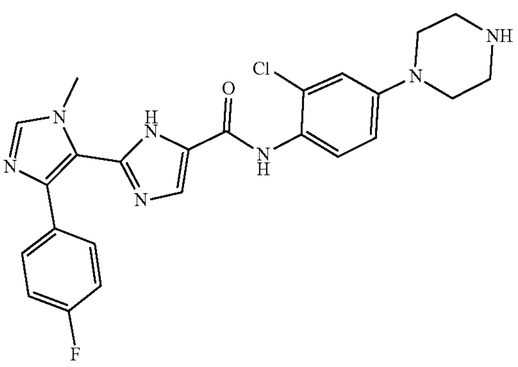

N-(2-chloro-4-(piperazin-1-yl)phenyl) 5′-(4-fluorophenyl)-3′-methyl-1H,3′H-[2,4′-biimidazole]-5-carboxamide -continued Compound C-27

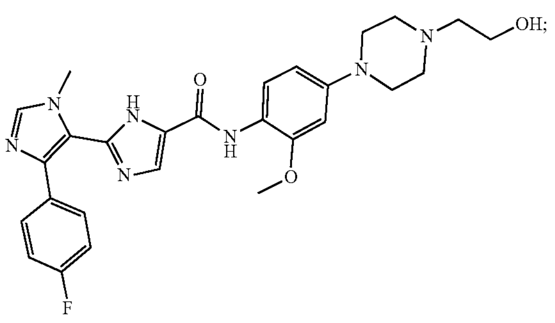

5′-(4-fluorophenyl)-N-(4-(4-(2-hydroxyethyl)piperazin-1-yl)-2-methoxyphenyl)-3′-methyl-1H,3′H-[2,4′-biimidazole]-5-carboxamide Compound C-28

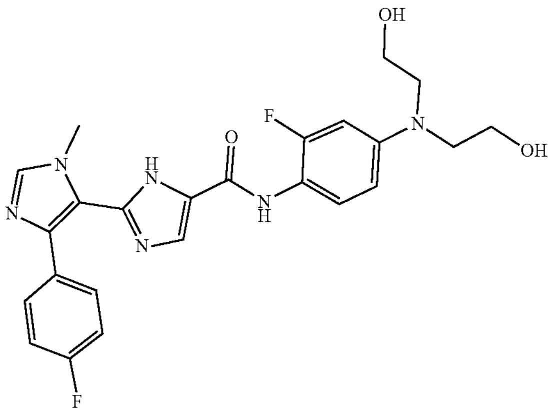

N-(4-(bis(2-hydroxyethyl)amino)-2-fluorophenyl)-5′-(4-fluorophenyl)-3′-methyl-1H,3′H-[2,4′-biimidazole]-5-carboxamide Compound C-29

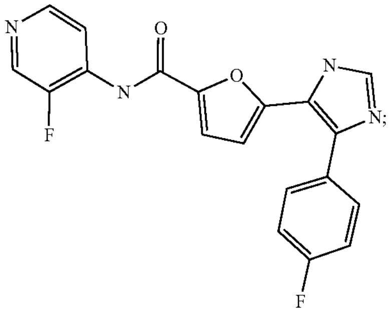

5-(4-(4-fluorophenyl)-1H-imidazol-5-yl)-N-(3-fluoropyridin-4-yl)furan-2-carboxamide -continued Compound C-30

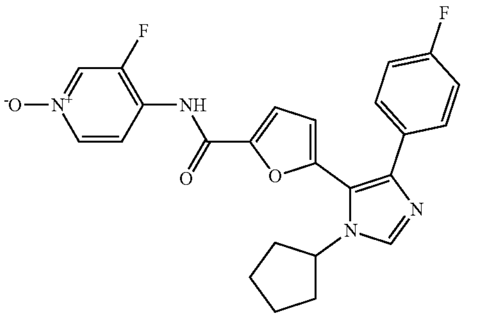

4-(5-(1-cyclopentyl-4-(4-fluorophenyl)-1H-imidazol-5-yl)furan-2-carboxamido)-3-fluoropyridine 1-oxide Compound C-31

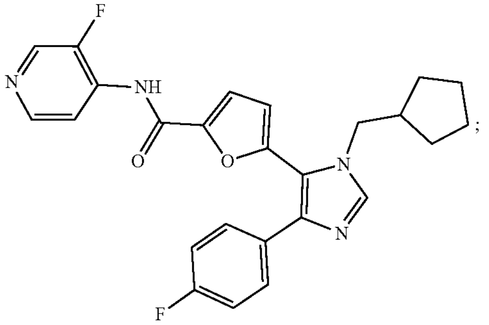

5-(1-cyclopentylmethyl)-4-(4-fluorophenyl)-1H-imidazol-5-yl)-N-(3-fluoropyridin-4-yl)furan-2-carboxamide Compound C-32

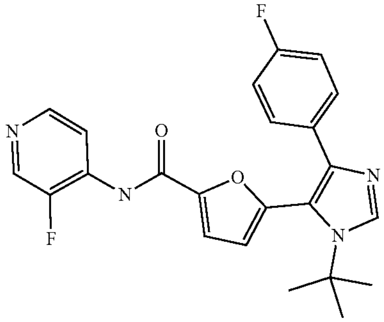

5-(1-tert-butyl)-4-(4-fluorophenyl)-1H-imidazol-5-yl)-N-(3-fluoropyridin-4-yl)furan-2-carboxamide -continued Compound C-33

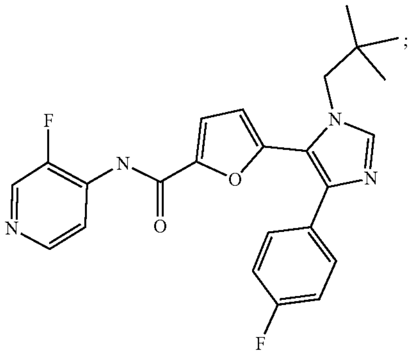

5-(4-(4-fluorophenyl)-1-neopentyl-1H-imidazol-5-yl)-N-(3-fluoropyridin-4-yl)furan-2-carboxamide Compound C-34

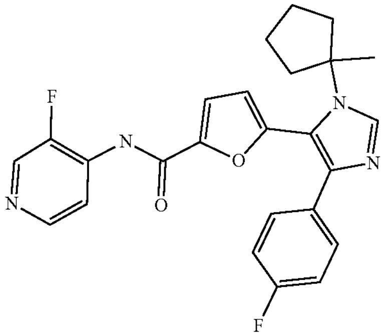

5-(4-(4-fluorophenyl)-1-(1-methylcyclopentyl)-1H-imidazol-5-yl)-N-(3-fluoropyridin-4-yl)furan-2-carboxamide Compound C-35

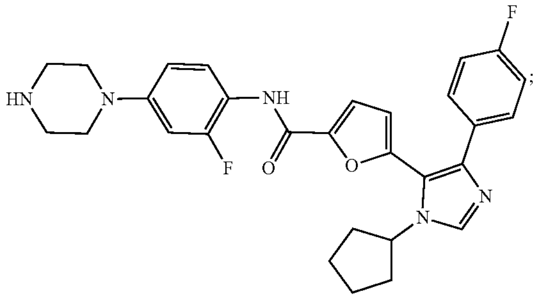

5-(1-cyclopentyl-4-(4-fluorophenyl)-1H-imidazol-5-yl)-N-(2-fluoro-4-(piperazin-1-yl)phenyl)furan-2-carboxamide Compound C-36

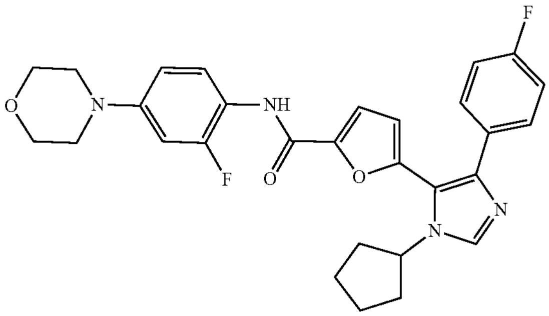

5-(1-cyclopentyl-4-(4-fluorophenyl)-1H-imidazol-5-yl)-N-(2-fluoro-4-morpholinophenyl)furan-2-carboxamide -continued Compound C-37

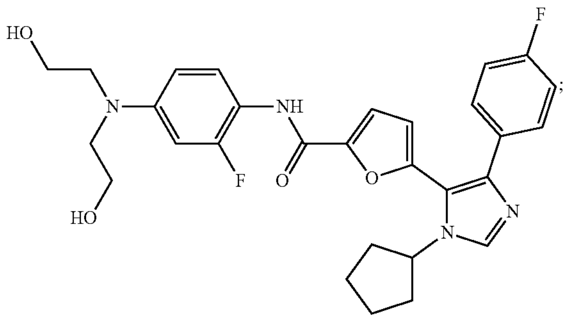

N-(4-(bis(2-hydroxyethyl)amino)-2-fluorophenyl)-5-(1-cyclopentyl-4-(4-fluorophenyl)-1H-imidazol-5-yl)furan-2-carboxamide Compound C-38

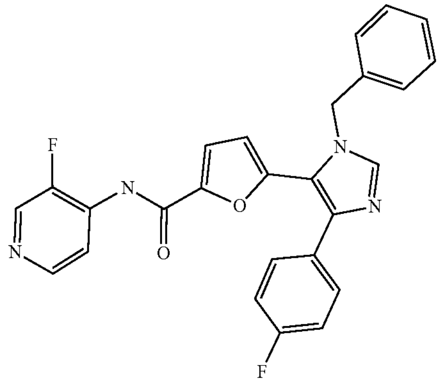

5-(1-benzyl-4-(4-fluorophenyl)-1H-imidazol-5-yl)-N-(3-fluoropyridin-4-yl)furan-2-carboxamide Compound C-39

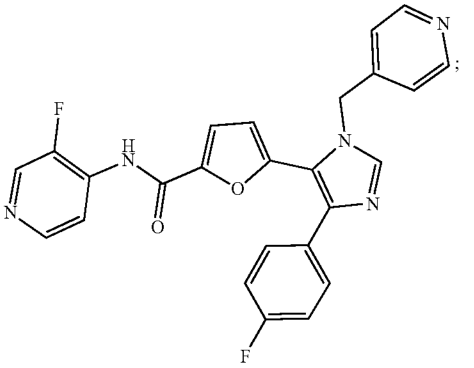

5-(4-(4-fluorophenyl)-1-(pyridin-4-ylmethyl)-1H-imidazol-5-yl)-N-(3-fluoropyridin-4-yl)furan-2-carboxamide -continued Compound C-40

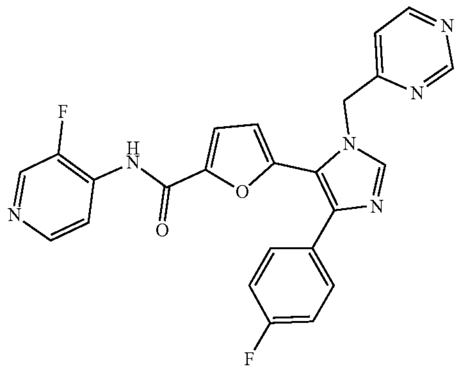

5-(4-(4-fluorophenyl)-1-(pyrimidin-4-ylmethyl)-1H-imidazol-5-yl)-N-(3-fluoropyridin-4-yl)furan-2-carboxamide Compound C-41

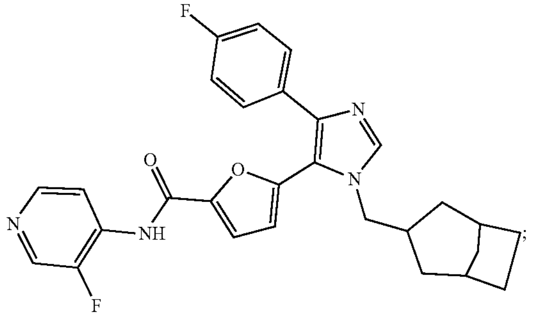

5-(1-bicyclo[3.2.1]octan-3-ylmethyl)-4-(4-fluorophenyl)-1H-imidazol-5-yl)-N-(3-fluoropyridin-4-yl)furan-2-carboxamide Compound C-42

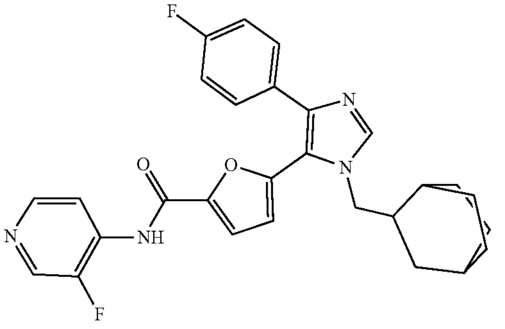

5-(1-bicyclo[2.2.2]octan-3-ylmethyl)-4-(4-fluorophenyl)-1H-imidazol-5-yl)-N-(3-fluoropyridin-4-yl)furan-2-carboxamide -continued Compound C-43

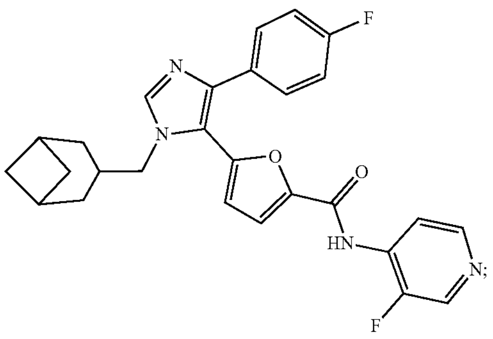

5-(1-bicyclo[3.1.1]heptan-3-ylmethyl)-4-(4-fluorophenyl)-1H-imidazol-5-yl)-N-(3-fluoropyridin-4-yl)furan-2-carboxamide Compound C-44

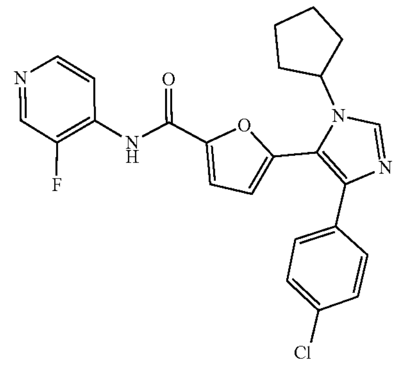

5-(4-(4-chlorophenyl)-1-cyclopentyl-1H-imidazol-5-yl)-N-(3-fluoropyridin-4-yl)furan-2-carboxamide Compound C-45

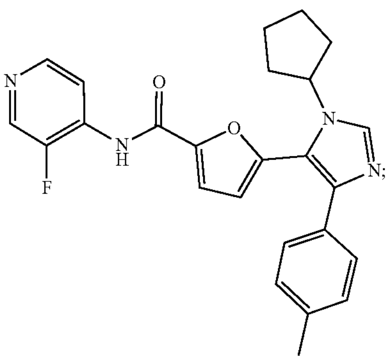

5-(1-cyclopentyl-4-(p-tolyl)-1H-imidazol-5-yl)-N-(3-fluoropyridin-4-yl)furan-2-carboxamide -continued Compound C-46

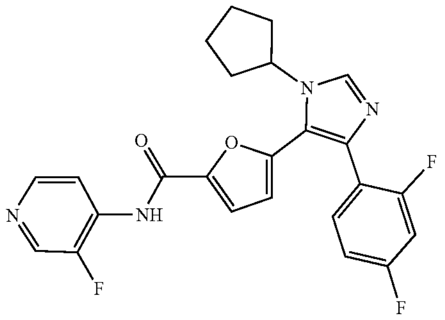

5-(1-cyclopentyl-4-(2,4-difluorophenyl)-1H-imidazol-5-yl)-N-(3-fluoropyridin-4-yl)furan-2-carboxamide Compound C-47

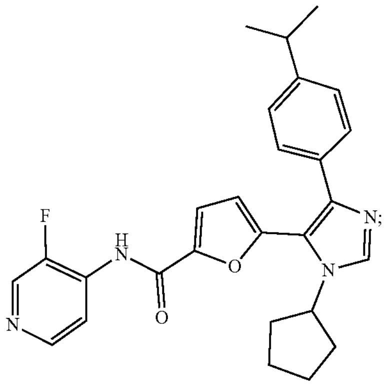

5-(1-cyclopentyl-4-(4-isopropylphenyl)-1H-imidazol-5-yl)-N-(3-fluoropyridin-4-yl)furan-2-carboxamide Compound C-48

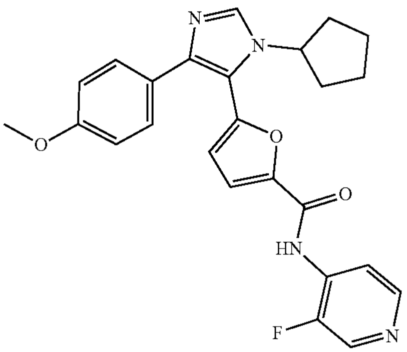

5-(1-cyclopentyl-4-(4-methoxyphenyl)-1H-imidazol-5-yl)-N-(3-fluoropyridin-4-yl)furan-2-carboxamide Compound C-49

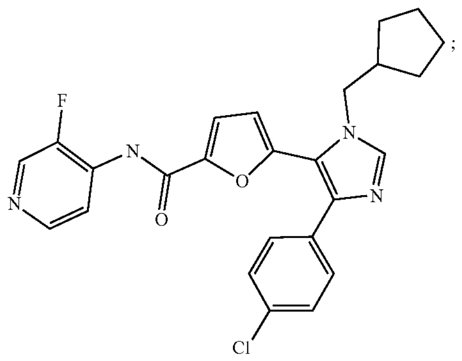

5-(4-(4-chlorophenyl)-1-(cyclopentylmethyl)-1H-imidazol-5-yl)-N-(3-fluoropyridin-4-yl)furan-2-carboxamide Compound C-50

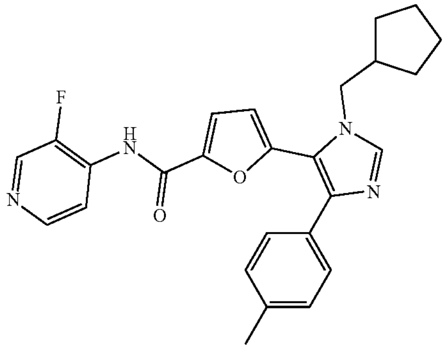

5-(1-(cyclopentylmethyl)-4-(p-tolyl)-1H-imidazol-5-yl)-N-(3-fluoropyridin-4-yl)furan-2-carboxamide Compound C-51

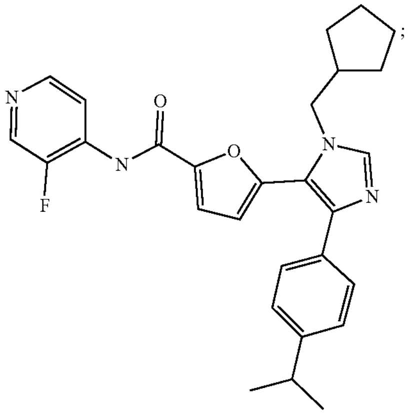

5-(1-(cyclopentylmethyl)-4-(4-isopropylphenyl)-1H-imidazol-5-yl)-N-(3-fluoropyridin-4-yl)furan-2-carboxamide Compound C-52

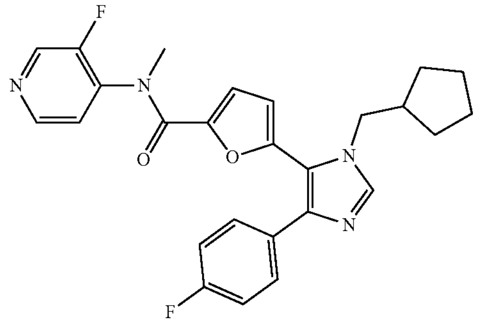

5-(1-(cyclopentylmethyl)-4-(4-fluorophenyl)-1H-imidazol-5-yl)-N-(3-fluoropyridin-4-yl)-N-methylfuran-2-carboxamide Compound C-56

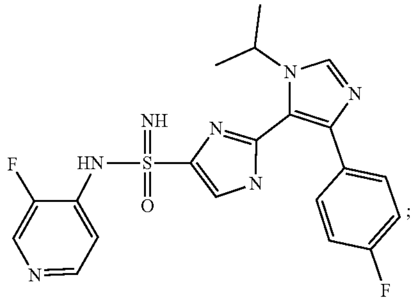

5′-(4-fluorophenyl)-N-(3-fluoropyridin-4-yl)-3′-isopropyl-1H,3′H-[2,4′-biimidazole]-4-sulfonimidamide Compound C-57

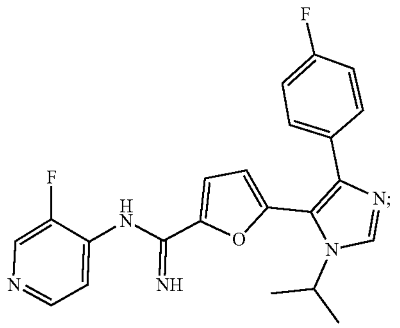

5-(4-(4-fluorophenyl)-1-isopropyl-1H-imidazol-5-yl)-N-(3-fluoropyridin-4-yl)furan-2-carboxamide Compound C-58

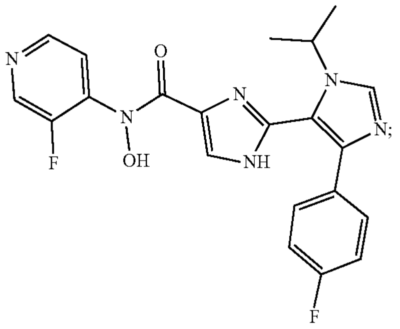

5′-(4-fluorophenyl)-N-(3-fluoropyridin-4-yl)-N-hydroxy-3′-isopropyl-1H,3′H-[2,4′-biimidazole]-4-carboxamide -continued Compound C-59

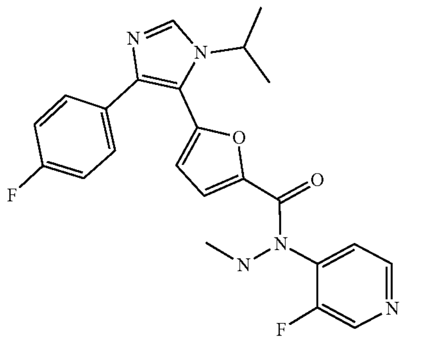

5-(4-(4-fluorophenyl)-1-isopropyl-1H-imidazol-5-yl)-N-(3-fluoropyridin-4-yl)-N'-methylfuran-2-carbohydrazide In some embodiments, the core structures of Compounds 80-106 that are TNIK kinase inhibitors can be devoid of the substitution pattern and substituents of the Compounds 1-79 that are not specifically recited in this paragraph.

In some embodiments, wherein the compound is one of the following (Compound 80-106): 5-(1-(cyclopentylmethyl)-4-(4-fluorophenyl)-1H-imidazol-5-yl)-N-(2-fluorophenyl)furan-2-carboxamide (Compound 80); N-(2-fluorophenyl)-5-(4-(4-fluorophenyl)-1-((tetrahydrofuran-3-yl)methyl)-1H-imidazol-5-yl)furan-2-carboxamide (Compound 81); N-(2-fluorophenyl)-5-(4-(4-fluorophenyl)-1-(pyrrolidin-3-ylmethyl)-1H-imidazol-5-yl)furan-2-carboxamide (Compound 82); 5-(1-cyclopropyl-4-(4-fluorophenyl)-1H-imidazol-5-yl)-N-(2-fluorophenyl)furan-2-carboxamide (Compound 83); N-(2-fluorophenyl)-5-(4-(4-fluorophenyl)-1-isopropyl-1H-imidazol-5-yl)furan-2-carboxamide (Compound 84); N-(2-fluorophenyl)-5-(4-(4-fluorophenyl)-1-(pyrrolidin-3-yl)-1H-imidazol-5-yl)furan-2-carboxamide (Compound 85); N-(2-fluorophenyl)-5-(4-(4-fluorophenyl)-1-(tetrahydrofuran-3-yl)-1H-imidazol-5-yl)furan-2-carboxamide (Compound 86); N-(2-fluorophenyl)-5-(4-(4-fluorophenyl)-1-((tetrahydrofuran-2-yl)methyl)-1H-imidazol-5-yl)furan-2-carboxamide (Compound 87); N-(2-fluorophenyl)-5-(4-(4-fluorophenyl)-1-(pyrrolidin-2-ylmethyl)-1H-imidazol-5-yl)furan-2-carboxamide (Compound 88); 5-(1-cyclopentyl-4-(4-fluorophenyl)-1H-1,2,3-triazol-5-yl)-N-(2-fluorophenyl)furan-2-carboxamide (Compound 89); N-(2-fluorophenyl)-5-(4-(4-fluorophenyl)-1-(piperidin-4-yl)-1H-imidazol-5-yl)furan-2-carboxamide (Compound 90); 5-(1-cyclopentyl-4-(pyridin-4-yl)-1H-imidazol-5-yl)-N-(2-fluorophenyl)furan-2-carboxamide (Compound 91); 5-(1-cyclopentyl-4-(pyridin-3-yl)-1H-imidazol-5-yl)-N-(2-fluorophenyl)furan-2-carboxamide (Compound 92); 5-(1-cyclopentyl-4-(6-fluoropyridin-3-yl)-1H-imidazol-5-yl)-N-(2-fluorophenyl)furan-2-carboxamide (Compound 93); 5-(1-cyclopentyl-4-(pyrimidin-5-yl)-1H-imidazol-5-yl)-N-(2-fluorophenyl)furan-2-carboxamide (Compound 94); N-(5-(1-cyclopentyl-4-(4-fluorophenyl)-1H-imidazol-5-yl)furan-2-yl)-2-fluorobenzamide (Compound 95); 5-(1-cyclopentyl-4-(4-fluorophenyl)-1H-imidazol-5-yl)-N-(2-fluorophenyl)thiophene-2-carboxamide (Compound 96); 5-(1-cyclopentyl-4-(4-fluorophenyl)-1H-imidazol-5-yl)-N-(2-fluorophenyl)-1H-pyrrole-2-carboxamide (Compound 97); 2-(1-cyclopentyl-4-(4-fluorophenyl)-1H-imidazol-5-yl)-N-(2-fluorophenyl)oxazole-5-carboxamide (Compound 98); 5-(1-cyclopentyl-4-(4-fluorophenyl)-1H-imidazol-5-yl)-N-(2-fluorophenyl)oxazole-2-carboxamide (Compound 99); 2-(1-cyclopentyl-4-(4-fluorophenyl)-1H-imidazol-5-yl)-N-(2-fluorophenyl)thiazole-5-carboxamide (Compound 100); 3'-cyclopentyl-N-(2-fluorophenyl)-5'-(4-fluorophenyl)-1H,3'H-[2,4'-biimidazole]-5-carboxamide (Compound 101); 5-(1-cyclopentyl-4-(4-fluorophenyl)-1H-imidazol-5-yl)-N-(2-fluorophenyl)-4H-1,2,4-triazole-3-carboxamide (Compound 102); 5-(1-cyclopentyl-4-(4-fluorophenyl)-1H-imidazol-5-yl)-N-(3-fluoropyridin-4-yl)furan-2-carboxamide (Compound 103); 6-(1-cyclopentyl-4-(4-fluorophenyl)-1H-imidazol-5-yl)-N-(2-fluorophenyl)picolinamide (Compound 104); N-(5-fluoro-2-methoxyphenyl)-5-(2-phenyl-3,6,7,8-tetrahydrocyclopenta[d]pyrrolo[2,3-b]pyridin-1-yl)-1H-pyrrole-2-carboxamide (Compound 105); or N-(4-fluoro-2-methoxyphenyl)-5-(2-phenyl-7,8-dihydro-6H-cyclopenta[d]furo[2,3-b]pyridin-1-yl)-1H-pyrrole-2-carboxamide (Compound 106).

In some embodiments, wherein the compound is one of the following (Compound A-1 through A-63): 5-(1-(Cyclopentylmethyl)-4-(4-fluorophenyl)-1H-imidazol-5-yl)-N-(2-fluorophenyl)furan-2-carboxamide (Compound A-1); N-(2-fluorophenyl)-5-(4-(4-fluorophenyl)-1-((tetrahydrofuran-3-yl)methyl)-1H-imidazol-5-yl)furan-2-carboxamide (Compound A-2); N-(2-fluorophenyl)-5-(4-(4-fluorophenyl)-1-(pyrrolidin-3-ylmethyl)-1H-imidazol-5-yl)furan-2-carboxamide (Compound A-3); 5-(1-cyclopropyl-4-(4-fluorophenyl)-1H-imidazol-5-yl)-N-(2-fluorophenyl)furan-2-carboxamide (Compound A-4); N-(2-fluorophenyl)-5-(4-(4-fluorophenyl)-1-isopropyl-1H-imidazol-5-yl)furan-2-carboxamide (Compound A-5); N-(2-fluorophenyl)-5-(4-(4-fluorophenyl)-1-(pyrrolidin-3-yl)-1H-imidazol-5-yl)furan-2-carboxamide (Compound A-6); N-(2-fluorophenyl)-5-(4-(4-fluorophenyl)-1-(tetrahydrofuran-3-yl)-1H-imidazol-5-yl)furan-2-carboxamide (Compound A-8); N-(2-fluorophenyl)-5-(4-(4-fluorophenyl)-1-((tetrahydrofuran-2-yl)methyl)-1H-imidazol-5-yl)furan-2-carboxamide (Compound A-9); N-(2-fluorophenyl)-5-(4-(4-fluorophenyl)-1-(pyrrolidin-2-ylmethyl)-1H-imidazol-5-yl)furan-2-carboxamide (Compound A-10); 5-(1-cyclopentyl-4-(4-fluorophenyl)-1H-1,2,3-triazol-5-yl)-N-(2-fluorophenyl)furan-2-carboxamide (Compound A-11); N-(2-fluorophenyl)-5-(4-(4-fluorophenyl)-1-(piperidin-4-yl)-1H-imidazol-5-yl)furan-2-carboxamide (Compound A-12); 5-(1-cyclopentyl-4-(pyridin-4-yl)-1H-imidazol-5-yl)-N-(2-fluorophenyl)furan-2-carboxamide (Compound A-13); 5-(1-cyclopentyl-4-(pyridin-3-yl)-1H-imidazol-5-yl)-N-(2-fluorophenyl)furan-2-carboxamide (Compound A-14); 5-(1-cyclopentyl-4-(6-fluoropyridin-3-yl)-1H-imidazol-5-yl)-N-(2-fluorophenyl)furan-2-carboxamide (Compound A-15); 5-(1-cyclopentyl-4-(pyrimidin-5-yl)-1H-imidazol-5-yl)-N-(2-fluorophenyl)furan-2-carboxamide (Compound A-16); N-(5-(1-cyclopentyl-4-(4-fluorophenyl)-1H-imidazol-5-yl)furan-2-yl)-2-fluorobenzamide (Compound A-17); 5-(1-cyclopentyl-4-(4-fluorophenyl)-1H-imidazol-5-yl)-N-(2-fluorophenyl)thiophene-2-carboxamide (Compound A-18); 5-(1-cyclopentyl-4-(4-fluorophenyl)-1H-imidazol-5-yl)-N-(2-fluorophenyl)-1H-pyrrole-2-carboxamide (Compound A-19); 2-(i-cyclopentyl-4-(4-fluorophenyl)-1H-imidazol-5-yl)-N-(2-fluorophenyl)oxazole-5-carboxamide (Compound A-20); 5-(1-cyclopentyl-4-(4-fluorophenyl)-1H-imidazol-5-yl)-N-(2-fluorophenyl)oxazole-2-carboxamide (Compound A-21); 2-(1-cyclopentyl-4-(4-fluorophenyl)-1H-imidazol-5-yl)-N-(2-fluorophenyl)thiazole-5-carboxamide (Compound A-22); 3'-cyclopentyl-N-(2-fluorophenyl)-5'-(4-fluorophenyl)-1H,3'H-[2,4'-biimidazole]-5-carboxamide (Compound A-23); 5-(1-cyclopentyl-4-(4-fluorophenyl)-1H-imidazol-5-yl)-N-(2-fluorophenyl)-4H-1,2,4-triazole-3-carboxamide (Compound A-24); 5-(1-cyclopentyl-4-(4-fluorophenyl)-

1H-imidazol-5-yl)-N-(3-fluoropyridin-4-yl)furan-2-carboxamide (Compound A-25); 6-(1-cyclopentyl-4-(4-fluorophenyl)-1H-imidazol-5-yl)-N-(2-fluorophenyl)picolinamide (Compound A-26); 5-(4-(4 fluorophenyl)-1-((tetrahydrofuran-3-yl)methyl)-1H-imidazol-5-yl)-N-(3-fluoropyridin-4-yl)furan-2-carboxamide (Compound A-36); 5-(4-(4-fluorophenyl)-1-((tetrahydrofuran-3-yl)methyl)-1H-imidazol-5-yl)-N-(3-methoxypyridin-4-yl)furan-2-carboxamide (Compound A 37); 5-(4-(4-fluorophenyl)-1-(tetrahydrofuran-3-yl)-1H-imidazol-5-yl)-N-(3-methoxypyridin-4-yl) furan-2-carboxamide (Compound A-38); 5-(1-cyclopentyl-4-(4-fluorophenyl)-1H-imidazol-5-yl)-N-(3-methoxypyridin-4-yl)furan-2-carboxamide (Compound A-39); 5-(1-(4,4-difluorotetrahydrofuran-3-yl)-4-(4-fluorophenyl)-1H-imidazol-5-yl)-N-(pyrimidin-4-yl)furan-2-carboxamide (Compound A-40); 5-(1-(4,4-difluorotetrahydrofuran-3-yl)-4-(4-fluorophenyl)-1H-imidazol-5-yl)-N-(3-fluoro-5-hydroxypyridin-4-yl)furan-2-carboxamide (Compound A-41); 5 (1-(4,4-difluorotetrahydrofuran-3-yl)-4-(4-fluorophenyl)-1H-imidazol-5-yl)-N-(2-oxo-1,2-dihydropyridin-4-yl) furan-2-carboxamide (Compound A-42); 5-(1-(4,4-difluorotetrahydrofuran-3-yl)-4-(4-fluorophenyl)-1H-imidazol-5-yl)-N-(5-fluoro-2-methylpyridin-4-yl)furan-2-carboxamide (Compound A-43); 5-(4-(4-fluorophenyl)-1-(oxetan-3-yl)-1H-imidazol-5-yl)-N-(pyrimidin-4-yl)furan-2-carboxamide (Compound A-44); N-(3-fluoro-5-hydroxypyridin-4-yl)-5-(4-(4-fluorophenyl)-1-(oxetan-3-yl)-1H-imidazol-5-yl) furan-2-carboxamide (Compound A-45); 5-(4-(4-fluorophenyl)-1-(oxetan-3-yl)-1H-imidazol-5-yl)-N-(2-oxo-1,2-dihydropyridin-4-yl)furan-2-carboxamide (Compound A-46); 5-(4-(4-fluorophenyl)-1-(oxetan-3-yl)-1H-imidazol-5-yl)-N-(2-methoxypyridin-4-yl)furan-2-carboxamide (Compound A-47); N-(5-fluoro-2-methylpyridin-4-yl)-5-(4-(4-fluorophenyl)-1-(oxetan-3-yl)-1H-imidazol-5-yl)furan-2-carboxamide (Compound A-48); 5-(4-(4-fluorophenyl)-1-methyl-1H-imidazol-5-yl)-N-(3-fluoropyridin-4-yl)furan-2-carboxamide (Compound A-49); S-(1-cyclopentyl-4-(4-fluorophenyl)-1H-imidazol-5-yl)-N-(2-fluoro-4-sulfamoylphenyl)furan-2-carboxamide (Compound A-50); N-(2-fluoro-4-sulfamoylphenyl)-5-(4-(4-fluorophenyl)-1-(1-hydroxy propan-2-yl)-1H-imidazol-5-yl)furan-2-carboxamide (Compound A-51); 4-(4-(5-(1-cyclopentyl-4-(4-fluorophenyl)-1H-imidazol-5-yl)furan-2-carboxamido)-3-fluorophenyl)-1-methylpiperazin-1-ium (Compound A-52); 5-(4-(4-fluorophenyl)-1-(4-fluorotetrahydrofuran-3-yl)-1H-imidazol-5-yl)-N-(3-fluoropyridin-4-yl)furan-2-carboxamide (Compound A-53); rac-5-(4-(4-fluorophenyl)-1-((3R,4S)-4-fluorotetrahydrofuran-3-yl)-1H-imidazol-5-yl)-N-(3-fluoropyridin-4-yl)furan-2-carboxamide (Compound A-54); 5-(4-(4-fluorophenyl)-1-(4-fluorotetrahydrofuran-3-yl)-1H-imidazol-5-yl)-N-(pyrimidin-4-yl)furan-2-carboxamide (Compound A-55); N-(3-fluoro-5-hydroxypyridin-4-yl)-5-(4-(4-fluorophenyl)-1-(4-fluorotetrahydrofuran-3-yl)-1H-imidazol-5-yl)furan-2-carboxamide (Compound A-56); rac-5-(4-(4-fluorophenyl)-1-((4R)-4-fluorotetrahydrofuran-3-yl)-1H-imidazol-5-yl)-N-(2-oxo-1,2-dihydropyridin-4-yl) furan-2-carboxamide (Compound A-57); N-(5-fluoro-2-methylpyridin-4-yl)-5-(4-(4-fluorophenyl)-1-(4-fluorotetrahydrofuran-3-yl)-1H-imidazol-5-yl)furan-2-carboxamide (Compound A-58); rac-5-(4-(4-fluorophenyl)-1-((1R,2R)-2-hydroxycyclopentyl)-1H-imidazol-5-yl)-N-(3-fluoropyridin-4-yl)furan-2-carboxamide (Compound A-60); rac-5-(4-(4-fluorophenyl)-1-((1R,2R)-2-hydroxycyclopentyl)-1H-imidazol-5-yl)-N-(3-fluoropyridin-4-yl)furan-2-carboxamide (Compound A-61); rac-5-(4-(4-fluorophenyl)-1-((1R,3S)-3-hydroxycyclopentyl)-1H-imidazol-5-yl)-N-(3-fluoropyridin-4-yl)furan-2-carboxamide (Compound A-62); or rac-5-(4-(4-fluorophenyl)-1-((1R,3 S)-3-hydroxycyclopentyl)-1H-imidazol-5-yl)-N-(3-fluoropyridin-4-yl)furan-2-carboxamide (Compound A-63).

In some embodiments, wherein the compound is one of the following (Compound B-1 through B-79): 5-(1-cyclopentyl-4-(4-fluorophenyl)-1H-imidazol-5-yl)-N-(2,4-difluorophenyl)furan-2-carboxamide (Compound B-1); 5-(1-cyclopentyl-4-(4-fluorophenyl)-1H-imidazol-5-yl)-N-(2,5-dimethoxyphenyl)furan-2-carboxamide (Compound B-2); 5-(1-cyclopentyl-4-(4-fluorophenyl)-1H-imidazol-5-yl)-N-(2,5-di fluorophenyl)furan-2-carboxamide (Compound B-3); 5-(1-cyclohexyl-4-(p-tolyl)-1H-imidazol-5-yl)-N-(3-methoxyphenyl)furan-2-carboxamide; (Compound B-4); 5-(1-cyclohexyl-4-(p-tolyl)-1H-imidazol-5-yl)-N-(4-methoxyphenyl)furan-2-carboxamide (Compound B-5); 5-(1-cyclohexyl-4-(p-tolyl)-1H-imidazol-5-yl)-N-(3,5-dimethoxyphenyl)furan-2-carboxamide (Compound B-6); 5-(1-cyclohexyl-4-(p-tolyl)-1H-imidazol-5-yl)-N-(2-fluorophenyl)furan-2-carboxamide (Compound B-7); 5-(1-cyclohexyl-4-(p-tolyl)-1H-imidazol-5-yl)-N-(4-fluorophenyl) furan-2-carboxamide (Compound B-8); N-(4-acetylphenyl)-5-(1-cyclopentyl-4-(4-fluorophenyl)-1H-imidazol-5-yl) furan-2-carboxamide (Compound B-9); 5-(1-cyclopentyl-4-(4-fluorophenyl)-1H-imidazol-5-yl)-N-(2-(trifluoromethyl) phenyl)furan-2-carboxamide (Compound B-10); 5-(1-cyclopentyl-4-(4-fluorophenyl)-1H-imidazol-5-yl)-N-(3,4-dimethoxyphenyl)furan-2-carboxamide (Compound B-11); 5-(1-cyclopentyl-4-(4-fluorophenyl)-1H-imidazol-5-yl)-N-(3-methoxyphenyl)furan-2-carboxamide (Compound B-12); N-(2-bromophenyl)-5-(1-cyclopentyl-4-(4-fluorophenyl)-1H-imidazol-5-yl)furan-2-carboxamide (Compound B-13); N-(2-chlorophenyl)-5-(1-cyclopentyl-4-(4-fluorophenyl)-1H-imidazol-5-yl)furan-2-carboxamide (Compound B-14); N-(4-chlorophenyl)-5-(1-cyclopentyl-4-(4-fluorophenyl)-1H-imidazol-5-yl)furan-2-carboxamide (Compound B-15); N-(4-chloro-2-methylphenyl)-5-(1-cyclopentyl-4-(4-fluorophenyl)-1H-imidazol-5-yl)furan-2-carboxamide (Compound B-16); N-(5-chloro-2-methylphenyl)-5-(1-cyclopentyl-4-(4-fluorophenyl)-1H-imidazol-5-yl)furan-2-carboxamide (Compound B-17); 5-(1-cyclopentyl-4-(4-fluorophenyl)-1H-imidazol-5-yl)-N-(2,4-dimethoxyphenyl) furan-2-carboxamide (Compound B-18); 5-(1-cyclopentyl-4-(4-fluorophenyl)-1H-imidazol-5-yl)-N-(3,5-dimethoxyphenyl)furan-2-carboxamide (Compound B-19); 5-(1-cyclopentyl-4-(4-fluorophenyl)-1H-imidazol-5-yl)-N-(2,3-dimethylphenyl)furan-2-carboxamide (Compound B-20); 5-(1-cyclopentyl-4-(4-fluorophenyl)-1H-imidazol-5-yl)-N-(2,6-dimethylphenyl)furan-2-carboxamide (Compound B-21); ethyl 3-(5-(1-cyclopentyl-4-(4-fluorophenyl)-1H-imidazol-5-yl)furan-2-carboxamido)benzoate (Compound B-22); 5-(1-cyclopentyl-4-(4-fluorophenyl)-1H-imidazol-5-yl)-N-(4-ethylphenyl)furan-2-carboxamide (Compound B-23); 5-(1-cyclopentyl-4-(4-fluorophenyl)-1H-imidazol-5-yl)-N-(2-fluorophenyl)furan-2-carboxamide (Compound B-24); 5-(1-cyclopentyl-4-(4-fluorophenyl)-1H-imidazol-5-yl)-N-(3-fluorophenyl)furan-2-carboxamide (Compound B-25); 5-(1-cyclopentyl-4-(4-fluorophenyl)-1H-imidazol-5-yl)-N-(4-fluorophenyl)furan-2-carboxamide (Compound B-26); methyl 2-(5-(1-cyclopentyl-4-(4-fluorophenyl)-1H-imidazol-5-yl)furan-2-carboxamido)benzoate (Compound B-27); 5-(1-cyclopentyl-4-(4-fluorophenyl)-1H-imidazol-5-yl)-N-(4-ethoxyphenyl)furan-2-carboxamide (Compound B-28); 5-(1-cyclopentyl-4-(4-fluorophenyl)-1H-imidazol-5-yl)-N-(o-tolyl)furan-2-carboxamide (Compound B-29); N-(3-chloro-4-methylphenyl)-5-(1-cyclopentyl-4-(4-fluorophenyl)-1H-imidazol-5-yl)furan-2- carboxamide (Compound B-30); 5-(1-cyclopentyl-4-(4-fluorophenyl)-1H-imidazol-5-yl)-N-(2,5-dimethylphenyl)furan-2-carboxamide (Compound B-31); 5-(1-cyclopentyl-4-(4-fluorophenyl)-1H-imidazol-5-yl)-N-(2,4-dimethylphenyl)furan-2-carboxamide (Compound B-32); ethyl 4-(5-(1-cyclopentyl-4-(4-fluorophenyl)-1H-imidazol-5-yl)furan-2-carboxamido)benzoate (Compound B-33); 5-(1-cyclopentyl-4-(4-fluorophenyl)-1H-imidazol-5-yl)-N-mesitylfuran-2-carboxamide (Compound B-34) N-(3-acetylphenyl)-5-(1-cyclopentyl-4-(4-fluorophenyl)-1H-imidazol-5-yl)furan-2-carboxamide (Compound B-35); 5-(1-cyclopentyl-4-(4-fluorophenyl)-1H-imidazol-5-yl)-N-(3-(methylthio)phenyl)furan-2-carboxamide (Compound B-36); 5-(1-cyclopentyl-4-(4-fluorophenyl)-1H-imidazol-5-yl)-N-(2-ethyl-6-methylphenyl)furan-2-carboxamide (Compound B-37); 5-(1-cyclopentyl-4-(4-fluorophenyl)-1H-imidazol-5-yl)-N-(4-isopropylphenyl)furan-2-carboxamide (Compound B-38); 5-(1-cyclopentyl-4-(4-fluorophenyl)-1H-imidazol-5-yl)-N-(3-ethylphenyl)furan-2-carboxamide (Compound B-39); 5-(1-cyclopentyl-4-(4-fluorophenyl)-1H-imidazol-5-yl)-N-(3-fluoro-4-methylphenyl)furan-2-carboxamide (Compound B-40); 5-(1-cyclopentyl-4-(4-fluorophenyl)-1H-imidazol-5-yl)-N-(3,4-difluorophenyl)furan-2-carboxamide (Compound B 41); N-(4-chloro-2-fluorophenyl)-5-(1-cyclopentyl-4-(4-fluorophenyl)-1H-imidazol-5-yl)furan-2-carboxamide (Compound B-42); 5-(1-cyclopentyl-4-(4-fluorophenyl)-1H-imidazol-5-yl)-N-(4-fluoro-2-methylphenyl)furan-2-carboxamide (Compound B-43); 5-(1-cyclopentyl-4-(4-fluorophenyl)-1H-imidazol-5-yl)-N-(4-(trifluoromethoxy)phenyl)furan-2-carboxamide (Compound B-44); N-(3-chloro-4-methoxyphenyl)-5-(1-cyclopentyl-4-(4-fluorophenyl)-1H-imidazol-5-yl)furan-2-carboxamide (Compound B-45); N-(4-acetamidophenyl)-5-(1-cyclopentyl-4-(4-fluorophenyl)-1H-imidazol-5-yl)furan-2-carboxamide (Compound B-46); 5-(1-cyclopentyl-4-(4-fluorophenyl)-1H-imidazol-5-yl)-N-(p-tolyl)furan-2-carboxamide (Compound B-47); 5-(1-cyclopentyl-4-(4-fluorophenyl)-1H-imidazol-5-yl)-N-(m-tolyl)furan-2-carboxamide (Compound B-48); N-(4-bromophenyl)-5-(1-cyclopentyl-4-(4-fluorophenyl)-1H-imidazol-5-yl)furan-2-carboxamide (Compound B-49); 5-(1-cyclopentyl-4-(4-fluorophenyl)-1H-imidazol-5-yl)-N-(2-methoxy phenyl)furan-2-carboxamide (Compound B-50); N-(4-acetylphenyl)-5-(1-cyclohexyl-4-(4-fluorophenyl)-1H-imidazol-5-yl)furan-2-carboxamide (Compound B-51); 5-(1-cyclohexyl-4-(4-fluorophenyl)-1H-imidazol-5-yl)-N-(3,4-dimethoxyphenyl)furan-2-carboxamide (Compound B-52); 5-(1-cyclohexyl-4-(4-fluorophenyl)-1H-imidazol-5-yl)-N-(3-methoxyphenyl)furan-2-carboxamide (Compound B-53); 5-(1-cyclohexyl-4-(4-fluorophenyl)-1H-imidazol-5-yl)-N-(4-methoxyphenyl)furan-2-carboxamide (Compound B-54); N-(2-chlorophenyl)-5-(1-cyclohexyl-4-(4-fluorophenyl)-1H-imidazol-5-yl)furan-2-carboxamide (Compound B-55); N-(4-chlorophenyl)-5-(1-cyclohexyl-4-(4-fluorophenyl)-1H-imidazol-5-yl)furan-2-carboxamide (Compound B-56); 5-(1-cyclohexyl-4-(4-fluorophenyl)-1H-imidazol-5-yl)-N-(2,4-difluorophenyl)furan-2-carboxamide (Compound B-57); 5-(1-cyclohexyl-4-(4-fluorophenyl)-1H-imidazol-5-yl)-N-(3,5-dimethoxyphenyl)furan-2-carboxamide (Compound B-58); 5-(1-cyclohexyl-4-(4-fluorophenyl)-1H-imidazol-5-yl)-N-(2,3-di methylphenyl)furan-2-carboxamide (Compound B-59); 5-(1-cyclohexyl-4-(4-fluorophenyl)-1H-imidazol-5-yl)-N-(2,6-dimethylphenyl)furan-2-carboxamide (Compound B-60); 5-(1-cyclohexyl-4-(4-fluorophenyl)-1H-imidazol-5-yl)-N-(2-ethyl phenyl)furan-2-carboxamide (Compound B-61); 5-(1-cyclohexyl-4-(4-fluorophenyl)-1H-imidazol-5-yl)-N-(2-fluorophenyl)furan-2-carboxamide (Compound B-62); 5-(1-cyclohexyl-4-(4-fluorophenyl)-1H-imidazol-5-yl)-N-(3-fluorophenyl)furan-2-carboxamide (Compound B-63); 5-(1-cyclohexyl-4-(4-fluorophenyl)-1H-imidazol-5-yl)-N-(4-ethoxyphenyl)furan-2-carboxamide (Compound B-64); 5-(1-cyclohexyl-4-(4-fluorophenyl)-1H-imidazol-5-yl)-N-(o-tolyl)furan-2-carboxamide (Compound B-65); N-(3-chloro-4-methylphenyl)-5-(1-cyclohexyl-4-(4-fluorophenyl)-1H-imidazol-5-yl)furan-2-carboxamide (Compound B-66); 5-(1-cyclohexyl-4-(4-fluorophenyl)-1H-imidazol-5-yl)-N-(2,4-dimethylphenyl)furan-2-carboxamide (Compound B-67); N-(2-chloro-4-methylphenyl)-5-(1-cyclohexyl-4-(4-fluorophenyl)-1H-imidazol-5-yl)furan-2-carboxamide (Compound B-68); 5-(1 cyclohexyl-4-(4-fluorophenyl)-1H-imidazol-5-yl)-N-(3,4-dimethylphenyl)furan-2-carboxamide (Compound B-69); 5-(1-cyclohexyl-4-(4-fluorophenyl)-1H-imidazol-5-yl)-N-mesitylfuran-2-carboxamide (Compound B-70); N-(3-acetylphenyl)-5-(1-cyclohexyl-4-(4-fluorophenyl)-1H-imidazol-5-yl)furan-2-carboxamide (Compound B-71); 5-(1-cyclohexyl-4-(4-fluorophenyl)-1H-imidazol-5-yl)-N-(3-(methylthio)phenyl)furan-2-carboxamide (Compound B-72); 5-(1 cyclohexyl-4-(4-fluorophenyl)-1H-imidazol-5-yl)-N-(4-isopropylphenyl)furan-2-carboxamide (Compound B-73); 5-(1-cyclohexyl-4-(4-fluorophenyl)-1H-imidazol-5-yl)-N-(3-ethylphenyl)furan-2-carboxamide (Compound B-74); 5-(1-cyclohexyl-4-(4-fluorophenyl)-1H-imidazol-5-yl)-N-(3,4-difluorophenyl)furan-2-carboxamide (Compound B-75); N-(4-chloro-2-fluorophenyl)-5-(1-cyclohexyl-4-(4-fluorophenyl)-1H-imidazol-5-yl)furan-2-carboxamide (Compound B-76); 5-(1-cyclohexyl-4-(4-fluorophenyl)-1H-imidazol-5-yl)-N-(2-methoxy-5-methylphenyl)furan-2-carboxamide (Compound B-77); N-(4-acetamidophenyl)-5-(1-cyclohexyl-4-(4-fluorophenyl)-1H-imidazol-5-yl)furan-2-carboxamide (Compound B-78); or 5-(1-cyclohexyl-4-(4-fluorophenyl)-1H-imidazol-5-yl)-N-(2-methoxyphenyl)furan-2-carboxamide (Compound B-79).

In some embodiments, wherein the compound is one of the following (Compound C-1 through C-59): 4-(3'-(tert-butyl)-5'-(4-fluorophenyl)-1H,3'H-[2,4'-biimidazole]-4-carboxamido)-3-fluoropyridine 1-oxide (Compound C-1); 3'-(tert-butyl)-N-(2-chloro-4-(2-hydroxyethyl)phenyl)-5'-(4-fluorophenyl)-1H,3'H-[2,4'-biimidazole]-5-carboxamide (Compound C-2); 4-(3'-(tert-butyl)-5'-(4-fluorophenyl)-1H,3'H-[2,4'-biimidazole]-5-carboxamido)-3-methoxybenzoic acid (Compound C-3); 3-(4-(3'-(tert-butyl)-5'-(4-fluorophenyl)-1H,3'H-[2,4'-biimidazole]-5-carboxamido)-3-fluorophenyl)propanoic acid (Compound C-4); 3'-(tert-butyl)-N-(2-chloro-4-(piperazin-1-yl)phenyl)-5'-(4-fluorophenyl)-1H,3'H-[2,4'-biimidazole]-5-carboxamide (Compound C-5); 3'-(tert-butyl)-5'-(4-fluorophenyl)-N-(4-(4-(2-hydroxyethyl)piperazin-1-yl)-2-methoxyphenyl)-1H,3'H-[2,4'-biimidazole]-5-carboxamide (Compound C-6); N-(4-(bis(2-hydroxyethyl)amino)-2-fluorophenyl)-3'-(tert-butyl)-5'-(4-fluorophenyl)-1H,3'H-[2,4'-biimidazole]-5-carboxamide (Compound C-7); 3-chloro-4-(5'-(4-fluorophenyl)-3'-(trifluoromethyl)-1H,3'H-[2,4'-biimidazole]-5-carboxamido)pyridine 1-oxide (Compound C-8); 5'-(4-fluorophenyl)-N-(4-(2-hydroxyethyl)-2-methoxyphenyl)-3'-(trifluoromethyl)-1H,3'H-[2,4'-biimidazole]-5-carboxamide (Compound C-9); 3-fluoro-4-(5'-(4-fluorophenyl)-3'-(trifluoromethyl)-1H,3'H-[2,4'-biimidazole]-5-carboxamido)benzoic acid (Compound C-10); 3-(3-chloro-4-(5'-(4-fluorophenyl)-3'-(trifluoromethyl)-1H,3'H-[2,4'-biimidazole]-5-carboxamido)phenyl)propanoic acid (Compound C-11); 5'-(4-fluorophenyl)-N-(2-methoxy-4-(piperazin-1-yl)phenyl)-3'-(trifluoromethyl)-1H,3'H-[2,4'-biimidazole]-5- carboxamide (Compound C-12); N-(2-fluoro-4-(4-(2-hydroxyethyl)piperazin-1-yl)phenyl)-5'-(4-fluorophenyl)-3'-(trifluoromethyl)-1H,3'H-[2,4'-biimidazole]-5-carboxamide (Compound C-13); N-(4-(bis(2-hydroxyethyl)amino)-2-chlorophenyl)-5'-(4-fluorophenyl)-3'-(trifluoromethyl)-1H,3'H-[2,4'-biimidazole]-5-carboxamide (Compound C-14); 4-(5'-(4-fluorophenyl)-3'-methoxy-1H,3'H-[2,4'-biimidazole]-5-carboxamido)-3-methoxypyridine 1-oxide (Compound C-15); N-(2-fluoro-4-(2-hydroxyethyl)phenyl)-5'-(4-fluorophenyl)-3'-methoxy-1H,3'H-[2,4'-biimidazole]-5-carboxamide (Compound C-16); 3-chloro-4-(5'-(4-fluorophenyl)-3'-methoxy-1H,3'H-[2,4'-biimidazole]-5-carboxamido)benzoic acid (Compound C-17); 3-(4-(5'-(4-fluorophenyl)-3'-methoxy-1H,3'H-[2,4'-biimidazole]-5-carboxamido)-3-methoxyphenyl)propanoic acid (Compound C-18); N-(2-fluoro-4-(piperazin-1-yl)phenyl)-5'-(4-fluorophenyl)-3'-methoxy-1H,3'H-[2,4'-biimidazole]-5-carboxamide (Compound C-19); N-(2-chloro-4-(4-(2-hydroxyethyl)piperazin-1-yl)phenyl)-5'-(4-fluorophenyl)-3'-methoxy-1H,3'H-[2,4'-biimidazole]-5-carboxamide (Compound C-20); N-(4-(bis(2-hydroxyethyl)amino)-2-methoxyphenyl)-5'-(4-fluorophenyl)-3'-methoxy-1H,3'H-[2,4'-biimidazole]-5-carboxamide (Compound C-21); 3-fluoro-4-(5'-(4-fluorophenyl)-3'-methyl-1H,3'H-[2,4'-biimidazole]-5-carboxamido)pyridine 1-oxide (Compound C-22); N-(2-chloro-4-(2-hydroxyethyl)phenyl)-5'-(4-fluorophenyl)-3'-methyl-1H,3'H-[2,4'-biimidazole]-5-carboxamide (Compound C-23); 4-(5'-(4-fluorophenyl)-3'-methyl-1H,3'H-[2,4'-biimidazole]-5-carboxamido)-3-methoxybenzoic acid (Compound C-24); 3-(3-fluoro-4-(5'-(4-fluorophenyl)-3'-methyl-1H,3'H-[2,4'-biimidazole]-5-carboxamido)phenyl)propanoic acid (Compound C-25); N-(2-chloro-4-(piperazin-1-yl)phenyl)-5'-(4-fluorophenyl)-3'-methyl-1H,3'H-[2,4'-biimidazole]-5-carboxamide (Compound C-26); 5'-(4-fluorophenyl)-N-(4-(4-(2-hydroxyethyl)piperazin-1-yl)-2-methoxyphenyl)-3'-methyl-1H,3'H-[2,4'-biimidazole]-5-carboxamide (Compound C-27); N-(4-(bis(2-hydroxyethyl)amino)-2-fluorophenyl)-5'-(4-fluorophenyl)-3'-methyl-1H,3'H-[2,4'-biimidazole]-5-carboxamide (Compound C-28); 5-(4-(4-fluorophenyl)-1H-imidazol-5-yl)-N-(3-fluoropyridin-4-yl)furan-2-carboxamide (Compound C-29); 4-(5-(1-cyclopentyl-4-(4-fluorophenyl)-1H-imidazol-5-yl)furan-2-carboxamido)-3-fluoropyridine 1-oxide (Compound C-30); 5-(1-(cyclopentylmethyl)-4-(4-fluorophenyl)-1H-imidazol-5-yl)-N-(3-fluoropyridin-4-yl)furan-2-carboxamide (Compound C-31); 5-(1-(tert-butyl)-4-(4-fluorophenyl)-1H-imidazol-5-yl)-N-(3-fluoropyridin-4-yl)furan-2-carboxamide (Compound C-32); 5-(4-(4-fluorophenyl)-1-neopentyl-1H-imidazol-5-yl)-N-(3-fluoropyridin-4-yl)furan-2-carboxamide (Compound C-33); 5-(4-(4-fluorophenyl)-1-(1-methylcyclopentyl)-1H-imidazol-5-yl)-N-(3-fluoropyridin-4-yl)furan-2-carboxamide (Compound C-34); 5-(1-cyclopentyl-4-(4-fluorophenyl)-1H-imidazol-5-yl)-N-(2-fluoro-4-(piperazin-1-yl)phenyl)furan-2-carboxamide (Compound C-35); 5-(1-cyclopentyl-4-(4-fluorophenyl)-1H-imidazol-5-yl)-N-(2-fluoro-4-morpholinophenyl)furan-2-carboxamide (Compound C-36); N-(4-(bis(2-hydroxyethyl)amino)-2-fluorophenyl)-5-(1-cyclopentyl-4-(4-fluorophenyl)-1H-imidazol-5-yl)furan-2-carboxamide (Compound C-37); 5-(1-benzyl-4-(4-fluorophenyl)-1H-imidazol-5-yl)-N-(3-fluoropyridin-4-yl)furan-2-carboxamide (Compound C-38); 5-(4-(4-fluorophenyl)-1-(pyridin-4-ylmethyl)-1H-imidazol-5-yl)-N-(3-fluoropyridin-4-yl)furan-2-carboxamide (Compound C-39); 5-(4-(4-fluorophenyl)-1-(pyrimidin-4-ylmethyl)-1H-imidazol-5-yl)-N-(3-fluoropyridin-4-yl)furan-2-carboxamide (Compound C-40); 5-(1-(bicyclo[3.2.1]octan-3-ylmethyl)-4-(4-fluorophenyl)-1H-imidazol-5-yl)-N-(3-fluoropyridin-4-yl)furan-2-carboxamide (Compound C-41); 5-(1-(bicyclo[2.2.2]octan-2-ylmethyl)-4-(4-fluorophenyl)-1H-imidazol-5-yl)-N-(3-fluoropyridin-4-yl)furan-2-carboxamide (Compound C-42); 5-(1-(bicyclo[3.1.1]heptan-3-ylmethyl)-4-(4-fluorophenyl)-1H-imidazol-5-yl)-N-(3-fluoropyridin-4-yl)furan-2-carboxamide (Compound C-43); 5-(4-(4-chlorophenyl)-1-cyclopentyl-1H-imidazol-5-yl)-N-(3-fluoropyridin-4-yl)furan-2-carboxamide (Compound C-44); 5-(1-cyclopentyl-4-(p-tolyl)-1H-imidazol-5-yl)-N-(3-fluoropyridin-4-yl)furan-2-carboxamide (Compound C-45); 5-(1-cyclopentyl-4-(2,4-difluorophenyl)-1H-imidazol-5-yl)-N-(3-fluoropyridin-4-yl)furan-2-carboxamide (Compound C-46); 5-(1-cyclopentyl-4-(4-isopropylphenyl)-1H-imidazol-5-yl)-N-(3-fluoropyridin-4-yl)furan-2-carboxamide (Compound C-47); 5-(1-cyclopentyl-4-(4-methoxyphenyl)-1H-imidazol-5-yl)-N-(3-fluoropyridin-4-yl)furan-2-carboxamide (Compound C-48); 5-(4-(4-chlorophenyl)-1-(cyclopentylmethyl)-1H-imidazol-5-yl)-N-(3-fluoropyridin-4-yl)furan-2-carboxamide (Compound C-49); 5-(1-(cyclopentylmethyl)-4-(p-tolyl)-1H-imidazol-5-yl)-N-(3-fluoropyridin-4-yl)furan-2-carboxamide (Compound C-50); 5-(1-(cyclopentylmethyl)-4-(4-isopropylphenyl)-1H-imidazol-5-yl)-N-(3-fluoropyridin-4-yl)furan-2-carboxamide (Compound C-51); 5-(1-(cyclopentylmethyl)-4-(4-fluorophenyl)-1H-imidazol-5-yl)-N-(3-fluoropyridin-4-yl)-N-methylfuran-2-carboxamide (Compound C-52); 5' (4-fluorophenyl)-N-(3-fluoropyridin-4-yl)-3'-isopropyl-1H,3'H-[2,4'-biimidazole]-4-sulfonimidamide (Compound C-56); 5-(4-(4-fluorophenyl)-1-isopropyl-1H-imidazol-5-yl)-N-(3-fluoropyridin-4-yl)furan-2-carboximidamide (Compound C-57); 5'-(4-fluorophenyl)-N-(3-fluoropyridin-4-yl)-N-hydroxy-3'-isopropyl-1H,3'H-[2,4'-biimidazole]-4-carboxamide (Compound C-58); or 5-(4-(4-fluorophenyl)-1-isopropyl-1H-imidazol-5-yl)-N-(3-fluoropyridin-4-yl)-N'-methylfuran-2-carbohydrazide (Compound C-59).

In some embodiments, the compound is included in a pharmaceutical composition comprising: the TNIK kinase inhibitor compound; and a pharmaceutically acceptable carrier having the compound.

In some aspects, the core structures of Compounds 80-106 that are TNIK kinase inhibitors (e.g., claimed compounds) can be devoid of the substitution pattern and substituents of the Compounds 1-79 that are not specifically recited in this paragraph.

In some embodiments, the claimed compound is not one of Compounds 1-79. However, these Compounds 1-79 can be used in the methods described herein.

In some embodiments, the claimed compound is not one of Compounds A-1 through A 63. However, these Compounds A-1 through A-63 can be used in the methods described herein.

In some embodiments, the claimed compound is not one of Compounds B-1 through B 79. However, these Compounds B-1 through B-79 can be used in the methods described herein.

In some embodiments, the claimed compound is not one of Compounds C-1 through C-59. However, these Compounds C-1 through C-59 can be used in the methods described herein.

In some embodiments, the claimed compound is not a compound under Formula B or Formula B1, which ring C as defined herein, such as a $C_5$-$C_6$ ring structure (e.g., cycloaliphatic) with or without hetero atoms. However, the compounds of Formula B or Formula B1 may be used in the methods described herein.

In some embodiments, the claimed compound is not a compound under Formula 7, Formula 8, Formula 9, Formula 10, Formula 11, Formula 12, Formula 13 or Formula 14, with Ring A as defined herein; however, these compounds may be used in the methods described herein.

In Vitro Assay Protocols

The MAP4K4 (h) is incubated with 8 mM MOPS pH 7.0, 0.2 mM EDTA, 250 uM, 10 mM MgAcetate and [gamma-33P-ATP] (specific activity and concentration as required). The reaction is initiated by the addition of the Mg/ATP mix. After incubation for 40 minutes at room temperature, the reaction is stopped by the addition of phosphoric acid to a concentration of 0.5%. 10 ul of the reaction is then spotted onto a P30 filtermat and washed four times for 4 minutes in 0.425% phosphoric acid and once in methanol prior to drying and scintillation counting.

LX-2 Fibrosis Assay.

Human hepatic stellate cell LX-2 were grown in DMEM (Invitrogen, 11960) supplied with 1% MEM Non-Essential Amino Acids (Invitrogen, 11140-050), 2% fetal bovine serum (Hyclone, SV30087.03), Penicillin (100 U/mL)-streptomycin (100 μg/mL) (Millipore, TMS-AB2-C) and 2 mM L-Glutamine (Invitrogen, 25030-001). After the cells grew in 12-well plates for 24 hours, the cell culture medium was changed to the same as above except using 0.4% fetal bovine serum. After 20 hour growth in the reduced serum medium, the cells were treated with indicated doses of compounds for 30 minutes. Subsequently, the cells were stimulated with 4 ng/mL TGF-b (R&D Systems, 240-B-002) for 48 hours. The cells were rinsed twice with DPBS before being harvested with 100 μL RIPA buffer (Sigma, R0278) supplemented with protease inhibitor cocktail (Roche, 04693132001) at 4° C. The total protein in each sample was quantified using BCA Protein Assay Kit (Pierce™, 23227) and equal amount of total protein of each sample was subject to Western blot analysis. Antibodies used were mouse anti-α-Actin (SPM332) (sc-365970), mouse anti-CTGF (E5) (sc-365970), and mouse anti-collagen al (3G3) (sc-293182), from Santa Cruz Biotechnologies; and mouse anti-GAPDH (6C5) (EMD Millipore, MAB374).

TABLE

TNIK, MAP4K4, Collagen Production Data:

| Example ID | TNIK_IC50 (nM) | MAP4K4_IC50 (nM) | Collagen Production EC50 (uM) LX-2 |
|---|---|---|---|
| A-1 | 26.35 | 102.49 | 0.4035 |
| A-2 | 36.87 | 114.02 | 1.6315 |
| A-3 | 158.31 | 3197.6 | 1.524 |
| A-4 | 63.88 | 183.11 | 1.056 |
| A-5 | 11.08 | 12.5 | 0.126 |
| A-6 | 251.33 | 1199.74 | 2.011 |
| A-8 | 25.08 | 141.72 | 1.1365 |
| A-9 | 76.49 | 222.43 | 1.503 |
| A-10 | 8452.1 | 12391.8 | |
| A-11 | 95.02 | | 1.7915 |
| A-12 | >10000 | 964.09 | |
| A-13 | 136.21 | 565.82 | 1.53 |
| A-14 | 93.17 | 111.69 | 4.28 |
| A-15 | 36.41 | 130.58 | 0.7542 |
| A-16 | >10000 | >10000 | |
| A-17 | 480.22 | 547.17 | |
| A-18 | >10000 | 55645 | |
| A-19 | | 12216 | |
| A-20 | 1732.91 | 2982.49 | |
| A-21 | 13835 | >10000 | |
| A-22 | 11692.7 | >10000 | |
| A-23 | 4.02 | 29.66 | 0.1257 |
| A-24 | >10000 | >10000 | |
| A-25 | 1.96 | 13.45 | 0.06682 |
| A-26 | 3.86 | <10 | 1.546 |
| A-36 | 83.25 | 160.75 | |
| A-37 | 26.35 | 50.31 | |
| A-38 | 4.21 | <10 | |
| A-39 | 1.29 | <10 | |
| A-40 | 26.31 | 50.47 | |
| A-41 | 316.58 | >1000 | |
| A-42 | 123.53 | 231.15 | |
| A-43 | | | |
| A-44 | | | |
| A-45 | 3723 | 6871.7 | >10 |
| A-46 | 5380 | 8303 | >10 |
| A-47 | | | 1.1965 |
| A-48 | 49.92 | 193.82 | |
| A-49 | 124.72 | >1000 | 0.4006 |
| A-50 | >1000 | >1000 | >10 |
| A-51 | | | |
| A-52 | 2.8 | <10 | 0.042 |
| A-53 | 191.21 | 337.07 | 1.983 |
| A-54 | 60.65 | 36.57 | 0.983 |
| A-55 | 91.03 | 301.06 | 0.4372 |
| A-56 | 1335.66 | 3073.36 | |
| A-57 | 1158.04 | | |
| A-58 | 75.2 | 95.38 | 0.669 |
| A-60 | 456.58 | 532.2 | 0.999 |
| A-61 | 28.75 | 23.44 | 0.22 |
| A-62 | 93 | 63.99 | 0.424 |
| A-63 | 9.32 | 4.72 | 0.286 |
| B-1 | 30 | 97.64 | |
| B-2 | 3.07 | 10.22 | |
| B-3 | 3.82 | 24.56 | |
| B-4 | 9322 | >1000 | |
| B-5 | 2408 | >1000 | |
| B-6 | 9726 | >1000 | |
| B-7 | 1506 | >1000 | |
| B-8 | 4449 | >1000 | |
| B-9 | 11 | 36.78 | |
| B-10 | <10 | 30.44 | |
| B-11 | 42 | 93.2 | |
| B-12 | 101 | 140.68 | |
| B-13 | 11.98 | 15.2 | |
| B-14 | 15.17 | 10.87 | |
| B-15 | 101 | 116.03 | |
| B-16 | 38 | 100.66 | |
| B-17 | 46 | 105.77 | |
| B-18 | 2.33 | 4.05 | |
| B-19 | 231 | 204.4 | |
| B-20 | 136 | 128.8 | |
| B-21 | 214 | >1000 | |
| B-22 | 483 | >1000 | |
| B-23 | 55 | 101.91 | |
| B-24 | 18.47 | 13.33 | |
| B-25 | 59 | 83.41 | |
| B-26 | 55 | 97.86 | |
| B-27 | 5.11 | 11.54 | |
| B-28 | 37 | 63.66 | |
| B-29 | 62 | 115.48 | |
| B-30 | 95 | 888.23 | |
| B-31 | 135 | 457.07 | |
| B-32 | 12 | 96.93 | |
| B-33 | 27 | 87.27 | |
| B-34 | 319 | 240.36 | |
| B-35 | 151 | 274.23 | |
| B-36 | 110 | 325.63 | |
| B-37 | 900 | >1000 | |
| B-38 | 46 | 167.61 | |
| B-39 | 480 | >1000 | |
| B-40 | 102 | 242.79 | |
| B-41 | 180 | 638.72 | |
| B-42 | 19 | 41.29 | |
| B-43 | 172 | 138.66 | |
| B-44 | 523 | 609.82 | |
| B-45 | 165 | 164.94 | |
| B-46 | 24 | 30.91 | |
| B-47 | 43.19 | 51.65 | |

TABLE-continued

| TNIK, MAP4K4, Collagen Production Data: | | | |
|---|---|---|---|
| Example ID | TNIK_IC50 (nM) | MAP4K4_IC50 (nM) | Collagen Production EC50 (uM) LX-2 |
| B-48 | 40 | 163.33 | |
| B-49 | 152 | 435.66 | |
| B-50 | 3.86 | 4.46 | |
| B-51 | 57 | 125.61 | |
| B-52 | 60 | 103.9 | |
| B-53 | 138 | 243.6 | |
| B-54 | 60 | 106.84 | |
| B-55 | 24 | 43.42 | |
| B-56 | 99 | 194.94 | |
| B-57 | 38 | 111.1 | |
| B-58 | 275 | 580.74 | |
| B-59 | 562 | >1000 | |
| B-60 | 874 | >1000 | |
| B-61 | 164 | 247.1 | |
| B-62 | 25 | 46.86 | |
| B-63 | 108 | 126.68 | |
| B-64 | 62 | 174.68 | |
| B-65 | 152 | 319.56 | |
| B-66 | 531 | >1000 | |
| B-67 | 77 | 247.48 | |
| B-68 | 19 | 71.71 | |
| B-69 | 90 | 287.57 | |
| B-70 | 936 | >1000 | |
| B-71 | 151 | 624.95 | |
| B-72 | 238 | 637.77 | |
| B-73 | 48 | 270.47 | |
| B-74 | 326 | 299.77 | |
| B-75 | 191 | 430.87 | |
| B-76 | 42 | 70.35 | |
| B-77 | 27 | 62.23 | |
| B-78 | 15 | 34.62 | |
| B-79 | 16 | 22.2 | |

Definitions

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively. Examples of Alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o methoxy-phenoxy, m-methoxy-phenoxy, p-methoxy-phenoxy, 2,4-dimethoxy-phenoxy, 3,4,5-trimethoxy-phenoxy, and the like.

The term “alkaryl” refers to an aryl group with an alkyl substituent, and the term “aralkyl” refers to an alkyl group with an aryl substituent, wherein “aryl” and “alkyl” are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctylnaphthyl, 3-ethyl-cyclopenta-1,4-diene, and the like.

The term “cyclic” refers to alicyclic or aromatic substituents that may or may not be substituted and/or heteroatom containing, and that may be monocyclic, bicyclic, or polycyclic.

The terms “halo” and “halogen” are used in the conventional sense to refer to a chloro, bromo, and fluoro or iodo substituent.

The term “heteroatom-containing” as in a “heteroatom-containing alkyl group” (also termed a “heteroalkyl” group) or a “heteroatom-containing aryl group” (also termed a “heteroaryl” group) or other use of “hetero” refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term “heteroalkyl” refers to an alkyl substituent that is heteroatom-containing, the term “heterocyclic” refers to a cyclic substituent that is heteroatom-containing, the terms “heteroaryl” and heteroaromatic” respectively refer to “aryl” and “aromatic” substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term “hydrocarbyl” refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. “Substituted hydrocarbyl” refers to hydrocarbyl substituted with one or more substituent groups, and the term “heteroatom-containing hydrocarbyl” refers to hydrocarbyl in which at least one carbon atom is replaced with a heteroatom. Unless otherwise indicated, the term “hydrocarbyl” is to be interpreted as including substituted and/or heteroatom-containing hydrocarbyl moieties.

By “substituted” as in “substituted alkyl,” “substituted aryl,” and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term “substituted” appears prior to a list of possible substituted groups or in reference to possible substituted groups, it is intended that the term apply to every member of that group. For example, the phrase “substituted alkyl, alkenyl, and aryl” is to be interpreted as “substituted alkyl, substituted alkenyl, and substituted aryl.” Analogously, when the term “heteroatom-containing” appears prior to a list of possible heteroatom-containing groups, it is intended that the term apply to every member of that group. For example, the phrase “heteroatom-containing alkyl, alkenyl, and aryl” is to be interpreted as “heteroatom-containing alkyl, heteroatom-containing alkenyl, and heteroatom-containing aryl.”

All other chemistry terms are defined as known in the art.

As used herein, the term “subject” refers to any animal (e.g., a mammal), including, but not limited to humans, non-human primates, rodents, and the like, which is to be the recipient of a particular treatment. Typically, the terms “subject” and “patient” are used interchangeably herein in reference to a human subject.

“Pharmaceutically acceptable” refers to approved or approvable by a regulatory agency of the Federal or a state government or listed in the U.S. Pharmacopeia or other generally recognized pharmacopeia for use in animals, including humans.

“Pharmaceutically acceptable salt” refers to a salt of a compound that is pharmaceutically acceptable and that possesses the desired pharmacological activity of the parent compound.

“Pharmaceutically acceptable excipient, carrier or adjuvant” refers to an excipient, carrier or adjuvant that can be administered to a subject, together with at least one TNIK inhibitor of the present disclosure, and which does not destroy the pharmacological activity thereof and is nontoxic when administered in doses sufficient to deliver a therapeutic amount of the TNIK inhibitor.

“Pharmaceutically acceptable vehicle” refers to a diluent, adjuvant, excipient, or carrier with which at least one TNIK inhibitor of the present disclosure is administered.

The term “effective amount,” “therapeutically effective amount” or “therapeutic effect” refers to an amount of a TNIK inhibitor, polypeptide, polynucleotide, small organic molecule, or other drug effective to “treat” a disease or disorder in a subject or mammal. In the case of cancer, the therapeutically effective amount of the drug has a therapeutic effect and as such can reduce the number of cancer cells; decrease tumorigenicity, tumorigenic frequency or tumorigenic capacity; reduce the number or frequency of cancer stem cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer; reduce morbidity and mortality; improve quality of life; or a combination of such effects.

Terms such as “treating” or “treatment” or “to treat” or “alleviating” or “to alleviate” refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder, and those in whom the disorder is to be prevented.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as “open” terms (e.g., the term “including” should be interpreted as “including but not limited to,” the term “having” should be interpreted as “having at least,” the term “includes” should be interpreted as “includes but is not limited to,” etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases “at least one” and “one or more” to introduce claim recitations. However, the use of such phrases should not be construed to imply that the introduction of a claim recitation by the indefinite articles “a” or “an” limits any particular claim containing such introduced claim recitation to embodiments containing only one such recitation, even when the same claim includes the introductory phrases “one or more” or “at least one” and indefinite articles such as “a” or “an” (e.g., “a” and/or “an” should be interpreted to mean “at least one” or “one or more”); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of “two recitations,” without other modifiers, means at least two recitations, or two or more recitations). Furthermore, in those instances where a convention analogous to “at least one of A, B, and C, etc.” is used, in general such a construction is intended in the sense one having skill in the art would understand the convention (e.g., “a system having at least one of A, B, and C” would include but not be limited to systems that have A alone, B alone, C alone, A and B together, A and C together, B and C together, and/or A, B, and C together, etc.). In those instances where a convention analogous to “at least one of A, B, or C, etc.” is used, in general such a construction is intended in the sense one having skill in the art would understand the convention (e.g., “a system having at least one of A, B, or C” would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase “A or B” will be understood to include the possibilities of “A” or “B” or “A and B.”

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety for all that they teach.

The invention claimed is:

1. A compound of a structure of Formula A, or a salt or solvate thereof,

Formula A

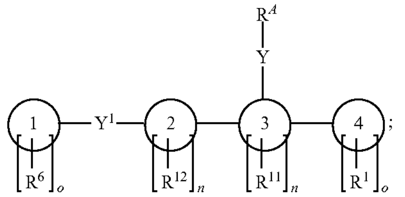

wherein:

ring 1 is a phenyl, pyridinyl, or pyrimidinyl;

ring 2 is a 5-membered hetero aromatic ring;

ring 3 is an imidazolyl;

ring 4 is a phenyl;

Y is a bond;

$Y^1$ is an amide linker having the nitrogen bonded to ring 1 and the carbon bonded to ring 2;

each n is independently 0, 1, or 2;

each o is independently 0, 1, 2, 3, 4, or 5;

each $R^1$, $R^6$, $R^{11}$, and $R^{12}$ is independently F, Br, Cl, I, methyl, ethyl, propyl, butyl, pentyl, hexyl, heptyl, octyl, isopropyl, tert-butyl, trifluoromethyl, hydroxy, methoxy, ethoxy, propoxy, butoxy, pentoxy, hexoxy, heptoxy, octoxy, trifluromethyloxy, oxygen, oxide, methylthio, ethylthio, propylthio, butylthio, pentylthio, hexylthio, heptylthio, octylthio, methylalcohol, ethylalcohol, propylalcohol, butylalcohol, pentylalcohol, hexylalcohol, heptylalcohol, octylalcohol, acetyl, carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethyl sulfanyl, propylsulfanyl, butyl sulfanyl, pentylsulfanyl, hexylsulfanyl, heptylsulfanyl, octylsulfanyl, sulfamoyl, methylpiperazinyl, piperazinyl, hydroxyethylpiperazinyl, bis(2-hydroxyethyl)amino, or morpholino;

$R^A$ is a cycloaliphatic ring, 5- or 6-membered hetero cycloaliphatic ring, straight aliphatic chain, or $C_3$-$C_{12}$ branched aliphatic chain, any of which is independently substituted or unsubstituted;

wherein the compound is subject to at least one of the following provisos a), or b):

a) when ring 1 is a phenyl group, ring 2 is not a furyl group; or b) when ring 2 is a furyl group, ring 1 is not a phenyl group.

2. The compound of claim 1, wherein:

ring 1 is a pyridinyl group, or pyrimidinyl group;

ring 2 is a furyl group;

ring 3 is an imidazolyl group; and ring 4 is a phenyl group.

3. The compound of claim 1, wherein n is 0, and each $R^1$ or $R^6$ is independently F, Br, Cl, I, methyl, ethyl, propyl, butyl, pentyl, hexyl, heptyl, octyl, isopropyl, tert-butyl, trifluoromethyl, oxygen, oxide, hydroxy, methoxy, ethoxy, propoxy, butoxy, pentoxy, hexoxy, heptoxy, octoxy, trifluromethyloxy, methylthio, ethylthio, propylthio, butylthio, pentylthio, hexylthio, heptylthio, octylthio, methyl alcohol, ethyl alcohol, propyl alcohol, butylalcohol, pentylalcohol, hexylalcohol, heptylalcohol, octylalcohol, acetyl, carboxylic acid, alkyl carboxylic acid, methyl carboxylic acid, ethyl carboxylic acid, propionyl, butyryl, acetamide, methylacetamide, ethylacetamide, propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl, thiomethyl, ethylsulfanyl, propylsulfanyl, butyl sulfanyl, pentyl sulfanyl, hexyl sulfanyl, heptyl sulfanyl, octyl sulfanyl, sulfamoyl, methylpiperazinyl, piperazinyl, hydroxyethylpiperazinyl, bis(2-hydroxyethyl)amino, or morpholino.

4. The compound of claim 3, wherein each $R^1$ is independently F, Br, Cl, I, methyl, ethyl, propyl, butyl, pentyl, hexyl, heptyl, octyl, isopropyl, tert-butyl, trifluoromethyl, hydroxy, methoxy, ethoxy, propoxy, butoxy, pentoxy, hexoxy, heptoxy, octoxy, or trifluromethyloxy.

5. The compound of claim 4, wherein each $R^6$ is independently F, Br, Cl, I, methyl, ethyl, propyl, butyl, pentyl, hexyl, heptyl, octyl, isopropyl, tert-butyl, trifluoromethyl, hydroxy, methoxy, ethoxy, propoxy, butoxy, pentoxy, hexoxy, heptoxy, octoxy, or trifluromethyloxy.

6. The compound of claim 1, wherein $R^A$ is cyclopentyl, tetrahydrofuranyl, pyrrolidinyl, piperidinyl, bicycloheptanyl, bicyclooctanyl, bicyclo[3.1.1]heptan-3-yl, bicyclo[2.2.2]octan-2-yl, bicyclo[3.2.1]octan-3-yl, fluorotetrahydrofuranyl, difluorotetrahydrofuranyl, hydroxycyclopentyl, methylcyclopentyl, cyclopropyl, cyclobutyl, cyclopentyl, cyclohexyl, isopropyl, or tert-butyl.

7. The compound of claim 1, or a salt or solvate thereof, wherein the compound is one of the following:

5-(1-cyclopentyl-4-(4-fluorophenyl)-1H-imidazol-5-yl)-N-(2-fluorophenyl)thiophene-2-carboxamide (Compound 96);

5-(1-cyclopentyl-4-(4-fluorophenyl)-1H-imidazol-5-yl)-N-(2-fluorophenyl)-1H-pyrrole-2-carboxamide (Compound 97);

2-(1-cyclopentyl-4-(4-fluorophenyl)-1H-imidazol-5-yl)-N-(2-fluorophenyl)oxazole-5-carboxamide (Compound 98);

5-(1-cyclopentyl-4-(4-fluorophenyl)-1H-imidazol-5-yl)-N-(2-fluorophenyl)oxazole-2-carboxamide (Compound 99);

2-(1-cyclopentyl-4-(4-fluorophenyl)-1H-imidazol-5-yl)-N-(2-fluorophenyl)thiazole-5-carboxamide (Compound 100);

3'-cyclopentyl-N-(2-fluorophenyl)-5'-(4-fluorophenyl)-1H,3'H-[2,4'-biimidazole]-5-carboxamide (Compound 101);

5-(1-cyclopentyl-4-(4-fluorophenyl)-1H-imidazol-5-yl)-N-(2-fluorophenyl)-4H-1,2,4-triazole-3-carboxamide (Compound 102); or 5-(1-cyclopentyl-4-(4-fluorophenyl)-1H-imidazol-5-yl)-N-(3-fluoropyridin-4-yl)furan-2-carboxamide (Compound 103).

8. A compound of one of the following, or a salt or solvate thereof:

5-(1-(Cyclopentylmethyl)-4-(4-fluorophenyl)-1H-imidazol-5-yl)-N-(2-fluorophenyl)furan-2-carboxamide (Compound A-1);

N-(2-fluorophenyl)-5-(4-(4-fluorophenyl)-1-((tetrahydrofuran-3-yl)methyl)-1H-imidazol-5-yl)furan-2-carboxamide (Compound A-2);

N-(2-fluorophenyl)-5-(4-(4-fluorophenyl)-1-(pyrrolidin-3-ylmethyl)-1H-imidazol-5-yl)furan-2-carboxamide (Compound A-3);
5-(1-cyclopropyl-4-(4-fluorophenyl)-1H-imidazol-5-yl)-N-(2-fluorophenyl)furan-2-carboxamide (Compound A-4);
N-(2-fluorophenyl)-5-(4-(4-fluorophenyl)-1-isopropyl-1H-imidazol-5-yl)furan-2-carboxamide (Compound A-5);
N-(2-fluorophenyl)-5-(4-(4-fluorophenyl)-1-(pyrrolidin-3-yl)-1H-imidazol-5-yl)furan-2-carboxamide (Compound A-6);
N-(2-fluorophenyl)-5-(4-(4-fluorophenyl)-1-(tetrahydrofuran-3-yl)-1H-imidazol-5-yl)furan-2-carboxamide (Compound A-8);
N-(2-fluorophenyl)-5-(4-(4-fluorophenyl)-1-((tetrahydrofuran-2-yl)methyl)-1H-imidazol-5-yl)furan-2-carboxamide (Compound A-9);
N-(2-fluorophenyl)-5-(4-(4-fluorophenyl)-1-(pyrrolidin-2-ylmethyl)-1H-imidazol-5-yl)furan-2-carboxamide (Compound A-10);
5-(1-cyclopentyl-4-(4-fluorophenyl)-1H-1,2,3-triazol-5-yl)-N-(2-fluorophenyl)furan-2-carboxamide (Compound A-11);
N-(2-fluorophenyl)-5-(4-(4-fluorophenyl)-1-(piperidin-4-yl)-1H-imidazol-5-yl)furan-2-carboxamide (Compound A-12);
5-(1-cyclopentyl-4-(pyridin-4-yl)-1H-imidazol-5-yl)-N-(2-fluorophenyl)furan-2-carboxamide (Compound A-13);
5-(1-cyclopentyl-4-(pyridin-3-yl)-1H-imidazol-5-yl)-N-(2-fluorophenyl)furan-2-carboxamide (Compound A-14);
5-(1-cyclopentyl-4-(6-fluoropyridin-3-yl)-1H-imidazol-5-yl)-N-(2-fluorophenyl)furan-2-carboxamide (Compound A-15);
5-(1-cyclopentyl-4-(pyrimidin-5-yl)-1H-imidazol-5-yl)-N-(2-fluorophenyl)furan-2-carboxamide (Compound A-16);
N-(5-(1-cyclopentyl-4-(4-fluorophenyl)-1H-imidazol-5-yl)furan-2-yl)-2-fluorobenzamide (Compound A-17);
5-(1-cyclopentyl-4-(4-fluorophenyl)-1H-imidazol-5-yl)-N-(2-fluorophenyl)thiophene-2-carboxamide (Compound A-18);
5-(1-cyclopentyl-4-(4-fluorophenyl)-1H-imidazol-5-yl)-N-(2-fluorophenyl)-1H-pyrrole-2-carboxamide (Compound A-19);
2-(1-cyclopentyl-4-(4-fluorophenyl)-1H-imidazol-5-yl)-N-(2-fluorophenyl)oxazole-5-carboxamide (Compound A-20);
5-(1-cyclopentyl-4-(4-fluorophenyl)-1H-imidazol-5-yl)-N-(2-fluorophenyl)oxazole-2-carboxamide (Compound A-21);
2-(1-cyclopentyl-4-(4-fluorophenyl)-1H-imidazol-5-yl)-N-(2-fluorophenyl)thiazole-5-carboxamide (Compound A-22);
3'-cyclopentyl-N-(2-fluorophenyl)-5'-(4-fluorophenyl)-1H,3'H-[2,4'-biimidazole]-5-carboxamide (Compound A-23);
5-(1-cyclopentyl-4-(4-fluorophenyl)-1H-imidazol-5-yl)-N-(2-fluorophenyl)-4H-1,2,4-triazole-3-carboxamide (Compound A-24);
5-(1-cyclopentyl-4-(4-fluorophenyl)-1H-imidazol-5-yl)-N-(3-fluoropyridin-4-yl)furan-2-carboxamide (Compound A-25);
6-(1-cyclopentyl-4-(4-fluorophenyl)-1H-imidazol-5-yl)-N-(2-fluorophenyl)picolinamide (Compound A-26);
5-(4-(4-fluorophenyl)-1-((tetrahydrofuran-3-yl)methyl)-1H-imidazol-5-yl)-N-(3-fluoropyridin-4-yl)furan-2-carboxamide (Compound A-36);
5-(4-(4-fluorophenyl)-1-((tetrahydrofuran-3-yl)methyl)-1H-imidazol-5-yl)-N-(3-methoxypyridin-4-yl)furan-2-carboxamide (Compound A-37);
5-(4-(4-fluorophenyl)-1-(tetrahydrofuran-3-yl)-1H-imidazol-5-yl)-N-(3-methoxypyridin-4-yl)furan-2-carboxamide (Compound A-38);
5-(1-cyclopentyl-4-(4-fluorophenyl)-1H-imidazol-5-yl)-N-(3-methoxypyridin-4-yl)furan-2-carboxamide (Compound A-39);
5-(1-(4,4-difluorotetrahydrofuran-3-yl)-4-(4-fluorophenyl)-1H-imidazol-5-yl)-N-(pyrimidin-4-yl)furan-2-carboxamide (Compound A-40);
5-(1-(4,4-difluorotetrahydrofuran-3-yl)-4-(4-fluorophenyl)-1H-imidazol-5-yl)-N-(3-fluoro-5-hydroxypyridin-4-yl)furan-2-carboxamide (Compound A-41);
5-(1-(4,4-difluorotetrahydrofuran-3-yl)-4-(4-fluorophenyl)-1H-imidazol-5-yl)-N-(2-oxo-1,2-dihydropyridin-4-yl)furan-2-carboxamide (Compound A-42);
5-(1-(4,4-difluorotetrahydrofuran-3-yl)-4-(4-fluorophenyl)-1H-imidazol-5-yl)-N-(5-fluoro-2-methylpyridin-4-yl)furan-2-carboxamide (Compound A-43);
5-(4-(4-fluorophenyl)-1-(oxetan-3-yl)-1H-imidazol-5-yl)-N-(pyrimidin-4-yl)furan-2-carboxamide (Compound A-44);
N-(3-fluoro-5-hydroxypyridin-4-yl)-5-(4-(4-fluorophenyl)-1-(oxetan-3-yl)-1H-imidazol-5-yl)furan-2-carboxamide (Compound A-45);
5-(4-(4-fluorophenyl)-1-(oxetan-3-yl)-1H-imidazol-5-yl)-N-(2-oxo-1,2-dihydropyridin-4-yl)furan-2-carboxamide (Compound A-46);
5-(4-(4-fluorophenyl)-1-(oxetan-3-yl)-1H-imidazol-5-yl)-N-(2-methoxypyridin-4-yl)furan-2-carboxamide (Compound A-47);
N-(5-fluoro-2-methylpyridin-4-yl)-5-(4-(4-fluorophenyl)-1-(oxetan-3-yl)-1H-imidazol-5-yl)furan-2-carboxamide (Compound A-48);
5-(4-(4-fluorophenyl)-1-methyl-1H-imidazol-5-yl)-N-(3-fluoropyridin-4-yl)furan-2-carboxamide (Compound A-49);
5-(1-cyclopentyl-4-(4-fluorophenyl)-1H-imidazol-5-yl)-N-(2-fluoro-4-sulfamoylphenyl)furan-2-carboxamide (Compound A-50);
N-(2-fluoro-4-sulfamoylphenyl)-5-(4-(4-fluorophenyl)-1-(1-hydroxypropan-2-yl)-1H-imidazol-5-yl)furan-2-carboxamide (Compound A-51);
4-(4-(5-(1-cyclopentyl-4-(4-fluorophenyl)-1H-imidazol-5-yl)furan-2-carboxamido)-3-fluorophenyl)-1-methylpiperazin-1-ium (Compound A-52);
5-(4-(4-fluorophenyl)-1-(4-fluorotetrahydrofuran-3-yl)-1H-imidazol-5-yl)-N-(3-fluoropyridin-4-yl)furan-2-carboxamide (Compound A-53);
rac-5-(4-(4-fluorophenyl)-1-((3R,4S)-4-fluorotetrahydrofuran-3-yl)-1H-imidazol-5-yl)-N-(3-fluoropyridin-4-yl)furan-2-carboxamide (Compound A-54);
5-(4-(4-fluorophenyl)-1-(4-fluorotetrahydrofuran-3-yl)-1H-imidazol-5-yl)-N-(pyrimidin-4-yl)furan-2-carboxamide (Compound A-55);
N-(3-fluoro-5-hydroxypyridin-4-yl)-5-(4-(4-fluorophenyl)-1-(4-fluorotetrahydrofuran-3-yl)-1H-imidazol-5-yl)furan-2-carboxamide (Compound A-56);
rac-5-(4-(4-fluorophenyl)-1-((4R)-4-fluorotetrahydrofuran-3-yl)-1H-imidazol-5-yl)-N-(2-oxo-1,2-dihydropyridin-4-yl)furan-2-carboxamide (Compound A-57);

N-(5-fluoro-2-methylpyridin-4-yl)-5-(4-(4-fluorophenyl)-1-(4-fluorotetrahydrofuran-3-yl)-1H-imidazol-5-yl)furan-2-carboxamide (Compound A-58);

rac-5-(4-(4-fluorophenyl)-1-((1R,2R)-2-hydroxycyclopentyl)-1H-imidazol-5-yl)-N-(3-fluoropyridin-4-yl)furan-2-carboxamide (Compound A-60);

rac-5-(4-(4-fluorophenyl)-1-((1R,2R)-2-hydroxycyclopentyl)-1H-imidazol-5-yl)-N-(3-fluoropyridin-4-yl)furan-2-carboxamide (Compound A-61);

rac-5-(4-(4-fluorophenyl)-1-((1R,3 S)-3-hydroxycyclopentyl)-1H-imidazol-5-yl)-N-(3-fluoropyridin-4-yl)furan-2-carboxamide (Compound A-62); or rac-5-(4-(4-fluorophenyl)-1-((1R,3 S)-3-hydroxycyclopentyl)-1H-imidazol-5-yl)-N-(3-fluoropyridin-4-yl)furan-2-carboxamide (Compound A-63).

9. The compound of claim 1, or a salt or solvate thereof, wherein the compound is one of the following:

4-(3'-(tert-butyl)-5'-(4-fluorophenyl)-1H,3'H-[2,4'-biimidazole]-4-carboxamido)-3-fluoropyridine 1-oxide (Compound C-1);

3'-(tert-butyl)-N-(2-chloro-4-(2-hydroxyethyl)phenyl)-5'-(4-fluorophenyl)-1H,3'H-[2,4'-biimidazole]-5-carboxamide (Compound C-2);

4-(3'-(tert-butyl)-5'-(4-fluorophenyl)-1H,3'H-[2,4'-biimidazole]-5-carboxamido)-3-methoxybenzoic acid (Compound C-3);

3-(4-(3'-(tert-butyl)-5'-(4-fluorophenyl)-1H,3'H-[2,4'-biimidazole]-5-carboxamido)-3-fluorophenyl)propanoic acid (Compound C-4);

3'-(tert-butyl)-N-(2-chloro-4-(piperazin-1-yl)phenyl)-5'-(4-fluorophenyl)-1H,3'H-[2,4'-biimidazole]-5-carboxamide (Compound C-5);

3'-(tert-butyl)-5'-(4-fluorophenyl)-N-(4-(4-(2-hydroxyethyl)piperazin-1-yl)-2-methoxyphenyl)-1H,3'H-[2,4'-biimidazole]-5-carboxamide (Compound C-6);

N-(4-(bis(2-hydroxyethyl)amino)-2-fluorophenyl)-3'-(tert-butyl)-5'-(4-fluorophenyl)-1H,3'H-[2,4'-biimidazole]-5-carboxamide (Compound C-7);

4-(5-(1-cyclopentyl-4-(4-fluorophenyl)-1H-imidazol-5-yl)furan-2-carboxamido)-3-fluoropyridine 1-oxide (Compound C-30);

5-(1-(tert-butyl)-4-(4-fluorophenyl)-1H-imidazol-5-yl)-N-(3-fluoropyridin-4-yl)furan-2-carboxamide (Compound C-32);

5-(4-(4-fluorophenyl)-1-neopentyl-1H-imidazol-5-yl)-N-(3-fluoropyridin-4-yl)furan-2-carboxamide (Compound C-33);

5-(4-(4-fluorophenyl)-1-(1-methylcyclopentyl)-1H-imidazol-5-yl)-N-(3-fluoropyridin-4-yl)furan-2-carboxamide (Compound C-34);

5-(4-(4-chlorophenyl)-1-cyclopentyl-1H-imidazol-5-yl)-N-(3-fluoropyridin-4-yl)furan-2-carboxamide (Compound C-44);

5-(1-cyclopentyl-4-(p-tolyl)-1H-imidazol-5-yl)-N-(3-fluoropyridin-4-yl)furan-2-carboxamide (Compound C-45);

5-(1-cyclopentyl-4-(2,4-difluorophenyl)-1H-imidazol-5-yl)-N-(3-fluoropyridin-4-yl)furan-2-carboxamide (Compound C-46);

5-(1-cyclopentyl-4-(4-isopropylphenyl)-1H-imidazol-5-yl)-N-(3-fluoropyridin-4-yl)furan-2-carboxamide (Compound C-47); or 5-(1-cyclopentyl-4-(4-methoxyphenyl)-1H-imidazol-5-yl)-N-(3-fluoropyridin-4-yl)furan-2-carboxamide (Compound C-48).

* * * * *